US010183066B2

(12) United States Patent
Boes et al.

(10) Patent No.: US 10,183,066 B2
(45) Date of Patent: Jan. 22, 2019

(54) MULTI-COMPONENT-MULTISTAGE MALARIA VACCINES

(71) Applicant: Fraunhofer-Gesellschaft zur Foerderung der angewandten Forschung e.V., Munich (DE)

(72) Inventors: Alexander Boes, Cologne (DE); Holger Spiegel, Aachen (DE); Gueven Edgue, Aachen (DE); Veronique Beiss, Aachen (DE); Markus Sack, Alsdorf (DE); Andreas Reimann, Krefeld (DE); Rainer Fischer, Aachen (DE)

(73) Assignee: Fraunhofer-Gesellschaft zur Foerderung der angewandten Forschung e.V, Munich (DE)

( * ) Notice: Subject to any disclaimer, the term of this patent is extended or adjusted under 35 U.S.C. 154(b) by 0 days.

(21) Appl. No.: 15/129,230

(22) PCT Filed: Mar. 27, 2015

(86) PCT No.: PCT/EP2015/056693
§ 371 (c)(1),
(2) Date: Sep. 26, 2016

(87) PCT Pub. No.: WO2015/144874
PCT Pub. Date: Oct. 1, 2015

(65) Prior Publication Data
US 2017/0106071 A1 Apr. 20, 2017

Related U.S. Application Data

(60) Provisional application No. 61/972,002, filed on Mar. 28, 2014.

(30) Foreign Application Priority Data

Mar. 28, 2014 (EP) ..................... 14001155

(51) Int. Cl.
*A61K 39/015* (2006.01)
*C07K 14/445* (2006.01)
*C07K 16/20* (2006.01)
*G01N 33/569* (2006.01)
*A61K 39/00* (2006.01)

(52) U.S. Cl.
CPC .......... *A61K 39/015* (2013.01); *C07K 14/445* (2013.01); *C07K 16/205* (2013.01); *G01N 33/56905* (2013.01); *A61K 2039/575* (2013.01); *A61K 2039/70* (2013.01); *C07K 2319/00* (2013.01); *C07K 2319/21* (2013.01); *G01N 2333/445* (2013.01); *Y02A 50/412* (2018.01)

(58) Field of Classification Search
None
See application file for complete search history.

(56) References Cited

U.S. PATENT DOCUMENTS

| 3,791,932 A | 2/1974 | Schuurs et al. |
| 3,839,153 A | 10/1974 | Wilhelmus et al. |
| 3,850,578 A | 11/1974 | McConnell |
| 3,850,752 A | 11/1974 | Wilhelmus et al. |
| 3,853,987 A | 12/1974 | Dreyer |
| 3,867,517 A | 2/1975 | Ling |
| 3,879,262 A | 4/1975 | Wilhelmus et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,666,828 A | 5/1987 | Gusella |
| 4,683,202 A | 7/1987 | Mullis |

(Continued)

FOREIGN PATENT DOCUMENTS

| CN | 102559613 A | 7/2012 |
| DE | 102012013860 A1 | 1/2014 |

(Continued)

OTHER PUBLICATIONS

Tsuboi et al. Infection and Immunity, Apr. 2008, vol. 76, No. 4, p. 1702-1708.*
Crompton et al. The Journal of Clinical Investigation. vol. 120, No. 12 p. 4168-4178, Dec. 2010.*
Imam et al. Clinical and Vaccine Immunology, Aug. 2011, 18(8): 1221-1228.*
Anderson, Laura Fay. PhD Thesis, University of Edinburgh 2006.*
Chen et al. PLOS Pathogen, Sep. 2011, 7(9):e1002199.*
Reiling et al. The Journal of Immunology, 2010, 185:6157-6167.*
Casilda et al. Molecular and Biochemical Parasitology 114 (2001) 217-226.*
Boes A, Spiegel H, Voepel N, Edgue G, Beiss V, Kapelski S, et al. (2015) Analysis of a Multi-component Multi-stage Malaria Vaccine Candidate—Tackling the Cocktail Challenge. PLoS ONE 10(7): e0131456. https://doi.org/10.1371/journal.pone.0131456).*

(Continued)

*Primary Examiner* — Oluwatosin A Ogunbiyi
(74) *Attorney, Agent, or Firm* — Wagenknecht IP Law Group PC

(57) ABSTRACT

The present disclosure relates to novel malaria vaccines composed of different recombinant proteins, in particular recombinant fusion proteins comprising several different *Plasmodium falciparum* antigens from the pre-erythrocytic the blood, and the sexual parasite stages. The proteins and/or fusion proteins will be used in a mixture vaccine formulation to elicit protective immune responses in humans. Nucleic acid molecules encoding said recombinant proteins, vectors, host cells containing the nucleic acids and methods for preparation and producing such proteins; Antibodies induced or generated by the use of said malaria vaccines or said nucleic acid molecules encoding said proteins and/or fusion proteins and the use of such antibodies or recombinant derivatives for passive immunotherapy.

14 Claims, 6 Drawing Sheets

Specification includes a Sequence Listing.

(56) References Cited

U.S. PATENT DOCUMENTS

| | | | |
|---|---|---|---|
| 4,801,531 | A | 1/1989 | Frossard |
| 4,879,219 | A | 11/1989 | Wands et al. |
| 5,011,771 | A | 4/1991 | Bellet et al. |
| 5,192,659 | A | 3/1993 | Simons |
| 5,272,057 | A | 12/1993 | Smulson et al. |
| 5,281,521 | A | 1/1994 | Trojanowski et al. |
| 2013/0216570 | A1 | 8/2013 | Schneerson et al. |

FOREIGN PATENT DOCUMENTS

| | | | |
|---|---|---|---|
| WO | 2007/027860 | A2 | 3/2007 |
| WO | 2007/041216 | A2 | 4/2007 |
| WO | 2010/037063 | A2 | 9/2009 |
| WO | 2012/047679 | A2 | 4/2012 |

OTHER PUBLICATIONS

Baum et al. Journal of Biological Chemistry vol. 281, No. 8, pp. 5197-5208 , 2006.*
Altschul et al. "Basic Local Alignment Search Tool," Journal of Molecular Biology, 1990, 215:403-410.
Ausubel et al. "Current Protocols in Molecular Biology," Molecular Reproduction and Development, 1989, 1:146.
Beier et al. "Effects of Para-aminobenzoic Acid, Insulin, and Gentamicin on Plasmodium Falciparum Development in Anopheline Mosquitoes (Diptera: Culicidae)," Journal of Medical Entomology, 1994, 31(4)561-565.
Bishop et al. "Experiments Upon the Feeding of Aedes Aegypti Through Animal Membranes with a View to Applying the Method to the Chemotherapy of Malaria," Parasitology, 1946, 37:85-100.
Black et al. "Apical Location of a Novel EGF-like Domain-Containing Protein of Plasmodium Falciparum," Molecular & Biochemical Parasitology, 2003, 127(1)59-68.
Black et al. "Merozoite Surface Protein 8 of Plasmodium Falcipuarum Contains Two Epidermal Growth Factor-Like Domains," Molecular & Biochemical Parasitology, 2001, 114:217-226.
Blackman et al. "Proteolytic Processing of the Plasmodium Falciparum Merozoite Surface Protein-1 Produces a Membrane-Bound Fragment Containing Two Epidermal Growth Factor-Like Domains," Molecular & Biochemical Parasitology, 1991, 49(1)29-34.
Boes et al. "Affinity Purification of a Framework 1 Engineered Mouse/Human Chimeric IgA2 Antibody From Tobacco," Biotechnology and Bioengineering, 2011, 108(12)2804-14.
Chothia et al. "Conformations of Immunoglobulin Hypervariable Regions," Nature, 1989, 342:877-883.
Schwartz et al. "Atlas of Protein Sequence and Structure," 1978, National Biomedical Research, 5(Supp 3)353-358.
Epping et al. "An Epitope Recognised by Inhibitory Monoclonal Antibodies that React with a 51 Kilodalton Merozoite Surface Antigen in Plasmodium Falciparum," Molecular & Biochemical Parasitology, 1988, 28(1)1-10.
Furie et al. "The Molecular Basis of Blood Coagulation," Cell, 1988, 53(4)505-518.
Bisaro et al. "Communications in Molecular Biology Viral Vectors," Cold Spring Harbor Laboratory, 1988, pp. 172-189, Cold Spring Harbor, NY.
Gosselin et al. "Enhanced Antigen Presentation Using Human Fc Gamma Receptor (Monocyte/Macrophage)-Specific Immunogens," Journal of Immunology, 1992, 149(11)3477-3481.
Grierson et al. "Plant Viruses," Plant Molecular Biology, 1988, pp. 126-146, Blackie, London.
Hugel et al. "Release of Malaria Circumsporozoite Protein into the Host Cell Cytoplasm and Interaction with Ribosomes," Molecular & Biochemical Parasitology, 1996, 81(2)151-170.
Ifediba et al. "Complete in Vitro Maturation of Plasmodium Falciparum Gametocytes," Nature, 1981, 294(5839)364-366.
Kaslow et al. "A Vaccine Candidate from the Sexual Stage of Human Malaria that Contains EGF-Like Domains," Nature, 1988, 333(6168)74-76.

Makler et al. "Parasite Lactate Dehydrogenase as an Assay for Plasmodium Falciparum Drug Sensitivity," The American Journal of Tropical Medicine and Hygiene, 1993, 48(6)739-741.
Marshall et al. "Close Linkage of Three Merozoite Surface Protein Genes on Chromosome 2 of Plasmodium Falciparum," Molecular & Biochemical Parasitology, 1998, 94(1)13-25.
McCormick et al. "Sporozoite Invasion Assay," Methods in Malaria Research, 5th Edition, Moll et al., Eds, 2008, MR4/ATCC Manassas, Virginia. BioMalPar Paris, France, pp. 138-140.
Pachebat et al. "The 22 kDa Component of the Protein Complex on the Surface of Plasmodium Falciparum Merozoites is Derived from a Larger Precursor, Merozoite Surface Protein 7," Molecular & Biochemical Parasitology, 2001, 117:83-89.
Patarroyo et al. "A Synthetic Vaccine Protects Humans Against Challenge with Asexual Blood Stages of Plasmodium Falciparum Malaria," Nature, 1988, 332(6160)158-161.
Rao et al. "Plant Cell Cultures: Chemical Factories of Secondary Metabolites." Biotechnology Advances 2002, 20(2)101-153.
Rothberg et al. "Slit: An EGF-Homologous Locus of D. Melanogaster Involved in the Development of the Embryonic Central Nervous System," Cell, 1988, 55(6)1047-1059.
Taylor, W.R. "The Classification of Amino Acid Conservation," Journal of Theoretical Biology, 1986, 119:205-218.
Trucco et al. "The Merozoite Surface Protein 6 Gene Codes for a 36 kDa Protein Associated with the Plasmodium Falciparum Merozoite Surface Protein-1 Complex," Molecular & Biochemical Parasitology, 2001,112:91-101.
Tucker, R.P. "The Thrombospondim Type 1 Repeat Family," International Journal of Biochemistry & Cell Biology, 2004,36:969-974.
Wong et al. "Heating Greatly Speeds Coomassie Blue Staining and Destaining," Biotechniques, 2000, 28(3)426-432.
PCT/EP2015/070044 International Search Report dated Apr. 11, 2015.
Faber et al. "Diversity Covering AMA1-MSP119 Fusion Proteins as Malaria Vaccines," Infection and Immunity, May 2013, 81(5)1479-1490.
Barry et al. "Strategies for Designing and Monitoring Malaria Vaccines Targeting Diverse Antigens," Frontiers in Immunology, Jul. 28, 2014, 5(359)1-16.
Arama et al. "The Path of Malaria Vaccine Development: Challenges and Perspectives," Journal of Internal Medicine, May 18, 2014, 275(5)456-466.
Srinivasan et al. "Immunization with a Functional Protein Complex Required for Erythrocyte Invasion Protects Against Lethal Malaria," Proceedings of the National Academy of Sciences, Jul. 15, 2014, 111(28)10311-10316.
Kumar et al. "Potent Malaria Transmission-Blocking Antibody Responses Elicited by Plasmodium falciparum Pfs25 Expressed in *Escherichia coli* after Successful Protein Refolding," Infection and Immunity, Apr. 1, 2014, 82(4)1453-1459.
Jones et al. "A Plant-Produced Pfs25 VLP Malaria Vaccine Candidate Induces Persistent Transmission Blocking Antibodies against Plasmodium falciparum in Immunized Mice," Plos One, 2013, 8(11)e79538(1-10).
Tamminga et al. "Human Adenovirus 5-vectored Plasmodium falciparum NMRC-M3V-Ad-PfCA Vaccine Encoding CSP and AMA1 is Safe, Well-Tolerated and Immunogenic But Does Not Protect Against Controlled Human Malaria Infection," Human Vaccines & Immunotherapeutics, Oct. 4, 2013, 9(10)2165-2177.
Appella et al. "The Receptor-Binding Sequence of Urokinase. A Biological Function for the Growth-Factor Module of Proteases," The Journal of Biological Chemistry, 1987, 262(10)4437-4440.
Bergmann-Leitner et al. "Immunization with Pre-erythrocytic Antigen CelTOS from Plasmodium Falciparum Elicits Cross-Species Protection Against Heterologous Challenge with Plasmodium Berghei," PLoS One, 2010, 5(8)e12294.
Knust et al. "EGF Homologous Sequences Encoded in the Genome of Drosophila Melanogaster, and their Relation to Neurogenic Genes," The EMBO Journal, 1987, 6(3)761-766.
Kurosawa et al. "A 10-kDa Cyanogen Bromide Fragment from the Epidermal Growth Factor Homology Domain of Rabbit Thrombomodulin Contains the Primary Thrombin Binding Site," The Journal of Biological Chemistry, 1988, 263(13)5993-5996.

(56) References Cited

OTHER PUBLICATIONS

Rees et al. "The Role of Beta-Hydroxyaspartate and Adjacent Carboxylate Residues in the First EGF Domain of Human Factor IX," The EMBO Journal, 1988, 7(7)2053-2061.
Sudhof et al. "The LDL Receptor Gene: A Mosaic of Exons Shared with Different Proteins," Science, 1985, 228(4701)815-822.
Suzuki et al. "Structure and Expression of Human Thrombomodulin, a Thrombin Receptor on Endothelium Acting as a Cofactor for Protein C Activation," The EMBO Journal, 1987, 6(7)1891-1897.
Brochet et al. "IMGT/V-QUEST: The Highly Customized and Integrated System for IG and TR Standardized V-J and V-D-J Sequence Analysis," Nucleic Acids Research, 2008, 36:W503-508.
Chen et al. "An EGF-Like Protein Forms a Complex with PfRh5 and is Required for Invasion of Human Erythrocytes by Plasmodium Falciparum," PLoS Pathogens, 2011, 7(9)e1102199.
Garcia-Basteiro et al. "Approaching the Target: the Path Towards an Effective Malaria Vaccine," Mediterranean Journal of Hematology and Infectious Diseases, 2012, 4(1)e2012015.
Geysen et al. "Use of Peptide Synthesis to Probe Viral Antigens for Epitopes to a Resolution of a Single Amino Acid," Proceedings of the National Academy of Sciences of the United States of America, 1984, 81:3998-4002.
Kariuki et al. "Plasmodium Falciparum: Purification of the Various Gametocyte Developmental Stages from In Vitro-Cultivated Parasites," The American Society of Tropical Medicine and Hygiene, 1998, 59(4)505-508.
Kusi et al. "Immunization with Different PfAMA1 Alleles in Sequence Induces Clonal Imprint Humoral Responses that are Similar to Responses Induced by the Same Alleles as a Vaccine Cocktail in Rabbits," Malaria Journal, 2011, 10(40)1-11.
Mahajan et al. "Multiple Antigen Peptide Vaccines Against Plasmodium Falciparum Malaria," Infection and Immunity, 2010, 78(11)4613-4624.
Marshall et al. "A Second Merozoite Surface Protein (MSP-4) of Plasmodium Falciparum that Contains an Epidermal Growth Factor-Like Domain," Infection and Immunity, 1997, 65(11)4460-4467.
Pradel et al. "A Multidomain Adhesion Protein Family Expressed in Plasmodium Falciparum is Essential for Transmission to the Mosquito," The Journal of Experimental Medicine, 2004, 199(11)1533-1544.
Pradel et al. "Malaria Sporozoites Actively Enter and Pass Through Rat Kupffer Cells Prior to Hepatocyte Invasion," Hepatology, 2001, 33(5)1154-1165.
Plassmeyer et al. "Structure of the Plasmodium Falciparum Circumsporozoite Protein, A Leading Malaria Vaccine Candidate." The Journal of Biological Chemistry, 2009, 284(39)26951-26963.
Rathore et al. "Molecular Mechanism of Host Specificity in Plasmodium Falciparum Infection: Role of Circumsporozoite Protein," The Journal of Biological Chemistry, 2003, 278(42)40905-40910.
Richards et al. "The Future for Blood-Stage Vaccines Against Malaria," Immunology and Cell Biology, 2009, 87(5) 377-390.
Roestenberg et al. "Safety and Immunogenicity of a Recombinant Plasmodium Falciparum AMA1 Malaria Vaccine Adjuvanted with Alhydrogel, Montanide ISA 720 or AS02," PloS one, 2008, 3(12)e3960.
Sack et al. "Functional Analysis of the Broadly Neutralizing Human Anti-HIV-1 Antibody 2F5 Produced in Transgenic BY-2 Suspension Cultures," The FASEB Journal, 2007, 21(8)1655-1664.
Schwartz et al. "A Review of Malaria Vaccine Clinical Projects Based on the WHO Rainbow Table," Malaria Journal, 2012, 11(11)1-22.
Smith et al. "Comparison of Biosequences," Advances in Applied Mathematics, 1981, 2:482-489.
Srinivasan et al. "Binding of Plasmodium Merozoite Proteins RON2 and AMA1 Triggers Commitment to Invasion," Proceedings of the National Academy of Sciences of the United States of America, 2011, 108(32):13275-13280.
Tachibana et al. "N-terminal Prodomain of Pfs230 Synthesized Using a Cell-Free System is Sufficient to Induce Complement-Dependent Malaria Transmission-Blocking Activity," Clinical and Vaccine Immunology, Aug. 2011, 18(8)1343-50.
Tan et al. "Crystal Structure of the TSP-1 Type 1 Repeats: A Novel Layered Fold and Its Biological Implication," The Journal of Cell Biology, 2002, 159(2)373-382.
Tossavainen et al. "The Layered Fold of the TSR Domain of P. Falciparum TRAP Contains a Heparin Binding Site," Protein Science, 2006, 15(7)1760-1768.
Uchime et al. "Analysis of the Conformation and Function of the Plasmodium falciparum Merozoite Proteins MTRAP and PTRAMP," Eukaryotic Cell, 2012, 11(5)615-625.
Vaquero et al. "Transient Expression of a Tumor-Specific Single-Chain Fragment and a Chimeric Antibody in Tobacco Leaves," Proceedings of the National Academy of Sciences of the United States of America, 1999, 96(20)11128-11133.
Wasmuth et al. "The Origins of Apicomplexan Sequence Innovation," Genome Research, 2009, 19(7)1202-1213.
PCT/EP2015/056693 International Search Report dated Jul. 27, 2015.

* cited by examiner

FIGURE 6
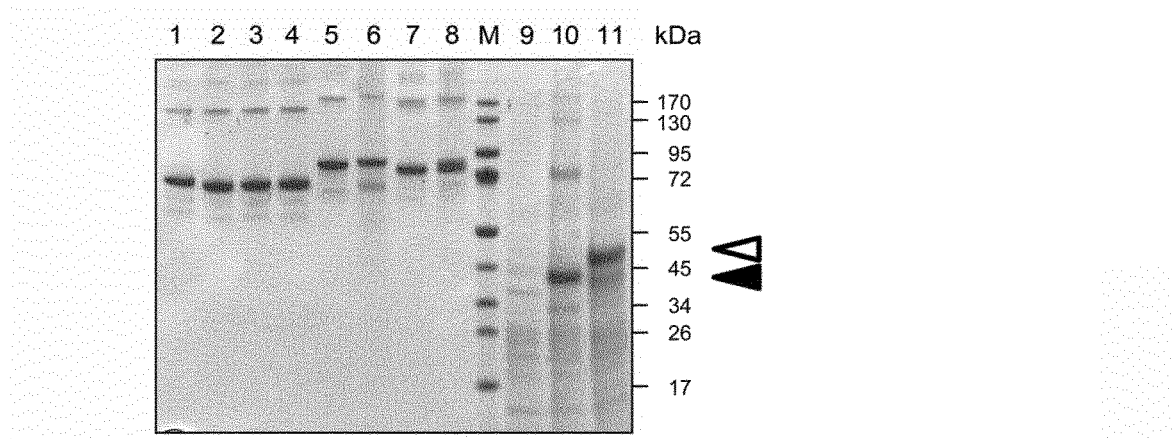
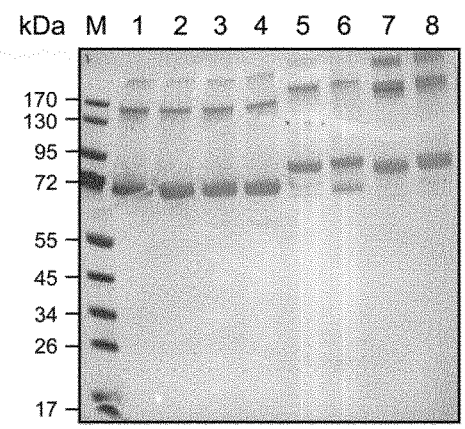

SEQUENCE LISTING

```
<160> NUMBER OF SEQ ID NOS: 45

<210> SEQ ID NO 1
<211> LENGTH: 308
<212> TYPE: PRT
<213> ORGANISM: Plasmodium falciparum

<400> SEQUENCE: 1

Met Ala Phe Arg Gly Asn Asn Gly His Asp Ser Ser Ser Leu Tyr
1               5                   10                  15

Gly Gly Ser Gln Phe Ile Glu Gln Leu Asp Asn Ser Phe Thr Ser Ala
            20                  25                  30
```

-continued

```
Phe Leu Glu Ser Gln Ser Met Asn Lys Ile Gly Asp Asp Leu Ala Glu
            35                  40                  45
Thr Ile Ser Asn Glu Leu Val Ser Val Leu Gln Lys Asn Ser Pro Thr
        50                  55                  60
Phe Leu Glu Ser Ser Phe Asp Ile Lys Ser Glu Val Lys Lys His Ala
65                  70                  75                  80
Lys Ser Met Leu Lys Glu Leu Ile Lys Val Gly Leu Pro Ser Phe Glu
                85                  90                  95
Asn Leu Val Ala Glu Asn Val Lys Pro Lys Val Asp Pro Ala Thr
            100                 105                 110
Tyr Gly Ile Ile Val Pro Val Leu Thr Ser Leu Phe Asn Lys Val Glu
            115                 120                 125
Thr Ala Val Gly Ala Lys Val Ser Asp Glu Ile Trp Asn Tyr Asn Ser
    130                 135                 140
Pro Asp Val Ser Glu Ser Glu Ser Leu Ser Asp Asp Phe Phe Asp
145                 150                 155                 160
Ala Ala Gly Pro Ser Asp Lys His Ile Glu Gln Tyr Leu Lys Lys Ile
                165                 170                 175
Gln Asn Ser Leu Ser Thr Glu Trp Ser Pro Cys Ser Val Thr Cys Gly
            180                 185                 190
Asn Gly Ile Gln Val Arg Ile Lys Pro Gly Ser Ala Asn Lys Pro Lys
        195                 200                 205
Asp Glu Leu Asp Tyr Glu Asn Asp Ile Glu Lys Lys Ile Cys Lys Met
    210                 215                 220
Glu Lys Cys Ser Ser Val Phe Asn Val Val Asn Ser Ala Ala Val Ala
225                 230                 235                 240
Met Ala Glu Lys Thr Ala Ser Cys Gly Val Trp Asp Glu Trp Ser Pro
                245                 250                 255
Cys Ser Val Thr Cys Gly Lys Gly Thr Arg Ser Arg Lys Arg Glu Ile
            260                 265                 270
Leu His Glu Gly Cys Thr Ser Glu Leu Gln Glu Gln Cys Glu Glu Glu
        275                 280                 285
Arg Cys Leu Pro Lys Ala Ala Ala His His His His His His Ser Glu
    290                 295                 300
Lys Asp Glu Leu
305

<210> SEQ ID NO 2
<211> LENGTH: 467
<212> TYPE: PRT
<213> ORGANISM: Plasmodium falciparum

<400> SEQUENCE: 2

Met Ala Ile Glu Ile Val Glu Arg Ser Asn Tyr Met Gly Asn Pro Trp
1               5                   10                  15
Thr Glu Tyr Met Ala Lys Tyr Asp Ile Glu Glu Val His Gly Ser Gly
                20                  25                  30
Ile Arg Val Asp Leu Gly Glu Asp Ala Glu Val Ala Gly Thr Gln Tyr
            35                  40                  45
Arg Leu Pro Ser Gly Lys Cys Pro Val Phe Gly Lys Gly Ile Ile Ile
        50                  55                  60
Glu Asn Ser Asn Thr Thr Phe Leu Thr Pro Val Ala Thr Gly Asn Gln
65                  70                  75                  80
Tyr Leu Lys Asp Gly Gly Phe Ala Phe Pro Pro Thr Glu Pro Leu Met
                85                  90                  95
```

-continued

Ser Pro Met Thr Leu Asp Glu Met Arg His Phe Tyr Lys Asp Asn Lys
            100                 105                 110

Tyr Val Lys Asn Leu Asp Glu Leu Thr Leu Cys Ser Arg His Ala Gly
        115                 120                 125

Asn Met Ile Pro Asp Asn Asp Lys Asn Ser Asn Tyr Lys Tyr Pro Ala
    130                 135                 140

Val Tyr Asp Asp Lys Asp Lys Lys Cys His Ile Leu Tyr Ile Ala Ala
145                 150                 155                 160

Gln Glu Asn Asn Gly Pro Arg Tyr Cys Asn Lys Asp Glu Ser Lys Arg
                165                 170                 175

Asn Ser Met Phe Cys Phe Arg Pro Ala Lys Asp Ile Ser Phe Gln Asn
            180                 185                 190

Tyr Thr Tyr Leu Ser Lys Asn Val Val Asp Asn Trp Glu Lys Val Cys
        195                 200                 205

Pro Arg Lys Asn Leu Gln Asn Ala Lys Phe Gly Leu Trp Val Asp Gly
    210                 215                 220

Asn Cys Glu Asp Ile Pro His Val Asn Glu Phe Pro Ala Ile Asp Leu
225                 230                 235                 240

Phe Glu Cys Asn Lys Leu Val Phe Glu Leu Ser Ala Ser Asp Gln Pro
                245                 250                 255

Lys Gln Tyr Glu Gln His Leu Thr Asp Tyr Glu Lys Ile Lys Glu Gly
            260                 265                 270

Phe Lys Asn Lys Asn Ala Ser Met Ile Lys Ser Ala Phe Leu Pro Thr
        275                 280                 285

Gly Ala Phe Lys Ala Asp Arg Tyr Lys Ser His Gly Lys Gly Tyr Asn
    290                 295                 300

Trp Gly Asn Tyr Asn Thr Glu Thr Gln Lys Cys Glu Ile Phe Asn Val
305                 310                 315                 320

Lys Pro Thr Cys Leu Ile Asn Asn Ser Ser Tyr Ile Ala Thr Thr Ala
                325                 330                 335

Leu Ser His Pro Ile Glu Val Glu Asn Asn Phe Pro Cys Ser Leu Tyr
            340                 345                 350

Lys Asp Glu Ile Met Lys Glu Ile Glu Arg Ser Lys Arg Ile Lys
        355                 360                 365

Leu Asn Asp Asn Asp Asp Glu Gly Asn Lys Lys Ile Ile Ala Pro Arg
    370                 375                 380

Ile Phe Ile Ser Asp Asp Lys Asp Ser Leu Lys Cys Pro Cys Asp Pro
385                 390                 395                 400

Glu Met Val Ser Asn Ser Thr Cys Arg Phe Phe Val Cys Lys Cys Val
                405                 410                 415

Glu Arg Arg Ala Glu Val Thr Ser Asn Asn Glu Val Val Lys Glu
            420                 425                 430

Glu Tyr Lys Asp Glu Tyr Ala Asp Ile Pro Glu His Lys Pro Thr Tyr
        435                 440                 445

Asp Lys Met Lys Ala Ala Ala His His His His His Ser Glu Lys
    450                 455                 460

Asp Glu Leu
465

<210> SEQ ID NO 3
<211> LENGTH: 337
<212> TYPE: PRT
<213> ORGANISM: Plasmodium falciparum

<400> SEQUENCE: 3

Met Ala Ile Ser Gln His Gln Cys Val Lys Lys Gln Cys Pro Glu Asn
1               5                   10                  15

Ser Gly Cys Phe Arg His Leu Asp Glu Arg Glu Cys Lys Cys Leu
            20                  25                  30

Leu Asn Tyr Lys Gln Glu Gly Asp Lys Cys Val Ala Gly Leu Glu
        35                  40                  45

Asp Glu Asp Leu Cys Lys His Asn Asn Gly Cys Gly Asp Asp Lys
50                  55                  60

Leu Cys Glu Tyr Val Gly Asn Arg Arg Val Lys Cys Cys Lys Glu
65                  70                  75                  80

Gly Tyr Lys Leu Glu Gly Ile Glu Cys Val Glu Leu Leu Ala Ala Gly
                85                  90                  95

Asn Asn Lys Val Cys Glu Asn Thr Lys Cys Pro Leu Asn Ser Asn Cys
                100                 105                 110

Tyr Val Ile Asp Asp Glu Glu Thr Cys Arg Cys Leu Pro Gly Phe Asn
                115                 120                 125

Asn Ile Lys Ile Asp Asp Glu Met Asn Cys Val Arg Asp Ala Ala Gly
                130                 135                 140

Asp Thr Leu Asp Cys Ser Arg Asn Asn Gly Gly Cys Asp Ile His Ala
145                 150                 155                 160

Lys Cys Ser Phe Ile Asn Lys Gln Ile Val Cys Glu Cys Lys Asp Lys
                165                 170                 175

Phe Glu Gly Asp Gly Ile Tyr Cys Ser Tyr Ser Ala Ala Gly Lys Glu
                180                 185                 190

Ile Val Lys Lys Tyr Asn Leu Asn Leu Arg Asn Ala Ile Leu Asn Asn
                195                 200                 205

Asn Ser Gln Ile Glu Asn Glu Glu Asn Val Asn Thr Thr Ile Thr Gly
        210                 215                 220

Asn Asp Phe Ser Gly Gly Glu Phe Leu Trp Pro Gly Tyr Thr Glu Glu
225                 230                 235                 240

Leu Lys Ala Lys Lys Ala Ser Glu Asp Ala Glu Lys Ala Ala Asn Asp
                245                 250                 255

Ala Glu Asn Ala Ser Lys Glu Ala Glu Glu Ala Ala Lys Glu Ala Val
                260                 265                 270

Asn Leu Lys Glu Ser Asp Lys Ser Tyr Thr Lys Ala Lys Glu Ala Ala
                275                 280                 285

Thr Ala Ala Ser Lys Ala Lys Lys Ala Val Glu Thr Ala Leu Lys Ala
                290                 295                 300

Lys Asp Asp Ala Glu Lys Ser Ser Lys Ala Asp Ser Ile Ser Thr Lys
305                 310                 315                 320

Thr Lys Ala Ala Ala His His His His His Ser Glu Lys Asp Glu
                325                 330                 335

Leu

<210> SEQ ID NO 4
<211> LENGTH: 332
<212> TYPE: PRT
<213> ORGANISM: Plasmodium falciparum

<400> SEQUENCE: 4

Met Val Thr Val Asp Thr Val Cys Lys Arg Gly Phe Leu Ile Gln Met
1               5                   10                  15

Ser Gly His Leu Glu Cys Lys Cys Glu Asn Asp Leu Val Leu Val Asn

```
                   20                  25                  30
Glu Glu Thr Cys Glu Glu Lys Val Leu Lys Cys Asp Glu Lys Thr Val
               35                  40                  45
Asn Lys Pro Cys Gly Asp Phe Ser Lys Cys Ile Lys Ile Asp Gly Asn
 50                  55                  60
Pro Val Ser Tyr Ala Cys Lys Cys Asn Leu Gly Tyr Asp Met Val Asn
 65                  70                  75                  80
Asn Val Cys Ile Pro Asn Glu Cys Lys Asn Val Ala Cys Gly Asn Gly
                 85                  90                  95
Lys Cys Ile Leu Asp Thr Ser Asn Pro Val Lys Thr Gly Val Cys Ser
                100                 105                 110
Cys Asn Ile Gly Lys Val Pro Asn Val Gln Asp Gln Lys Cys Ser Lys
                115                 120                 125
Asp Gly Glu Thr Lys Cys Ser Leu Lys Cys Leu Lys Glu Asn Glu Ala
                130                 135                 140
Cys Lys Ala Val Asp Gly Ile Tyr Lys Cys Asp Cys Lys Asp Gly Phe
145                 150                 155                 160
Ile Ile Asp Asn Glu Ala Ser Ile Cys Thr Ala Ala Val Glu Tyr Val
                165                 170                 175
Asp Glu Lys Glu Arg Gln Gly Glu Ile Tyr Pro Phe Gly Asp Glu Glu
                180                 185                 190
Glu Lys Asp Glu Gly Gly Glu Ser Phe Thr Tyr Glu Lys Ser Glu Val
                195                 200                 205
Asp Lys Thr Asp Leu Phe Lys Phe Ile Glu Gly Gly Glu Gly Asp Asp
                210                 215                 220
Val Tyr Lys Val Asp Gly Ser Lys Val Leu Leu Asp Asp Thr Ile
225                 230                 235                 240
Ser Arg Val Ser Lys Lys His Thr Ala Arg Asp Gly Glu Tyr Gly Glu
                245                 250                 255
Tyr Gly Glu Ala Val Glu Asp Gly Glu Asn Val Ile Lys Ile Ile Arg
                260                 265                 270
Ser Val Leu Gln Ser Gly Ala Leu Pro Ser Val Gly Val Asp Glu Leu
                275                 280                 285
Asp Lys Ile Asp Leu Ser Tyr Glu Thr Thr Glu Ser Gly Asp Thr Ala
                290                 295                 300
Val Ser Glu Asp Ser Tyr Asp Lys Tyr Ala Ser Asn Asn Ala Ala Ala
305                 310                 315                 320
His His His His His His Ser Glu Lys Asp Glu Leu
                325                 330

<210> SEQ ID NO 5
<211> LENGTH: 365
<212> TYPE: PRT
<213> ORGANISM: Plasmodium falciparum

<400> SEQUENCE: 5

Gln Asn Tyr Trp Glu His Pro Tyr Gln Lys Ser Asp Val Tyr His Pro
1               5                  10                  15
Ile Asn Glu His Arg Glu His Pro Lys Glu Tyr Glu Tyr Pro Leu His
                20                  25                  30
Gln Glu His Thr Tyr Gln Gln Glu Asp Ser Gly Glu Asp Glu Asn Thr
                35                  40                  45
Leu Gln His Ala Tyr Pro Ile Asp His Glu Gly Ala Glu Pro Ala Pro
 50                  55                  60
```

```
Gln Glu Gln Asn Leu Phe Ser Ser Met Ala Phe Arg Gly Asn Asn Gly
 65                  70                  75                  80

His Asp Ser Ser Ser Leu Tyr Gly Gly Ser Gln Phe Ile Glu Gln
                 85                  90                  95

Leu Asp Asn Ser Phe Thr Ser Ala Phe Leu Glu Ser Gln Ser Met Asn
                100                 105                 110

Lys Ile Gly Asp Asp Leu Ala Glu Thr Ile Ser Asn Glu Leu Val Ser
            115                 120                 125

Val Leu Gln Lys Asn Ser Pro Thr Phe Leu Glu Ser Ser Phe Asp Ile
        130                 135                 140

Lys Ser Glu Val Lys Lys His Ala Lys Ser Met Leu Lys Glu Leu Ile
145                 150                 155                 160

Lys Val Gly Leu Pro Ser Phe Glu Asn Leu Val Ala Glu Asn Val Lys
                165                 170                 175

Pro Pro Lys Val Asp Pro Ala Thr Tyr Gly Ile Ile Val Pro Val Leu
            180                 185                 190

Thr Ser Leu Phe Asn Lys Val Glu Thr Ala Val Gly Ala Lys Val Ser
        195                 200                 205

Asp Glu Ile Trp Asn Tyr Asn Ser Pro Asp Val Ser Glu Ser Glu Glu
    210                 215                 220

Ser Leu Ser Asp Asp Phe Phe Asp Ala Ala Gly Pro Ser Asp Lys His
225                 230                 235                 240

Ile Glu Gln Tyr Leu Lys Lys Ile Gln Asn Ser Leu Ser Thr Glu Trp
                245                 250                 255

Ser Pro Cys Ser Val Thr Cys Gly Asn Gly Ile Gln Val Arg Ile Lys
            260                 265                 270

Pro Gly Ser Ala Asn Lys Pro Lys Asp Glu Leu Asp Tyr Glu Asn Asp
        275                 280                 285

Ile Glu Lys Lys Ile Cys Lys Met Glu Lys Cys Ser Ser Val Phe Asn
    290                 295                 300

Val Val Asn Ser Ala Ala Val Ala Met Ala Glu Lys Thr Ala Ser Cys
305                 310                 315                 320

Gly Val Trp Asp Glu Trp Ser Pro Cys Ser Val Thr Cys Gly Lys Gly
                325                 330                 335

Thr Arg Ser Arg Lys Arg Glu Ile Leu His Glu Gly Cys Thr Ser Glu
            340                 345                 350

Leu Gln Glu Gln Cys Glu Glu Arg Cys Leu Pro Lys
        355                 360                 365

<210> SEQ ID NO 6
<211> LENGTH: 378
<212> TYPE: PRT
<213> ORGANISM: Plasmodium falciparum

<400> SEQUENCE: 6

Gln Asn Tyr Trp Glu His Pro Tyr Gln Lys Ser Asp Val Tyr His Pro
  1               5                  10                  15

Ile Asn Glu His Arg Glu His Pro Lys Glu Tyr Glu Tyr Pro Leu His
                 20                  25                  30

Gln Glu His Thr Tyr Gln Gln Glu Asp Ser Gly Glu Asp Glu Asn Thr
             35                  40                  45

Leu Gln His Ala Tyr Pro Ile Asp His Glu Gly Ala Glu Pro Ala Pro
         50                  55                  60

Gln Glu Gln Asn Leu Phe Ser Ser Met Ala Phe Arg Gly Asn Asn Gly
 65                  70                  75                  80
```

His Asp Ser Ser Ser Leu Tyr Gly Gly Ser Gln Phe Ile Glu Gln
                85                  90                  95

Leu Asp Asn Ser Phe Thr Ser Ala Phe Leu Glu Ser Gln Ser Met Asn
            100                 105                 110

Lys Ile Gly Asp Asp Leu Ala Glu Thr Ile Ser Asn Glu Leu Val Ser
        115                 120                 125

Val Leu Gln Lys Asn Ser Pro Thr Phe Leu Glu Ser Ser Phe Asp Ile
    130                 135                 140

Lys Ser Glu Val Lys Lys His Ala Lys Ser Met Leu Lys Glu Leu Ile
145                 150                 155                 160

Lys Val Gly Leu Pro Ser Phe Glu Asn Leu Val Ala Glu Asn Val Lys
                165                 170                 175

Pro Pro Lys Val Asp Pro Ala Thr Tyr Gly Ile Ile Val Pro Val Leu
            180                 185                 190

Thr Ser Leu Phe Asn Lys Val Glu Thr Ala Val Gly Ala Lys Val Ser
        195                 200                 205

Asp Glu Ile Trp Asn Tyr Asn Ser Pro Asp Val Ser Glu Ser Glu Glu
    210                 215                 220

Ser Leu Ser Asp Asp Phe Phe Asp Ala Ala Gly Pro Ser Asp Lys His
225                 230                 235                 240

Ile Glu Gln Tyr Leu Lys Lys Ile Gln Asn Ser Leu Ser Thr Glu Trp
                245                 250                 255

Ser Pro Cys Ser Val Thr Cys Gly Asn Gly Ile Gln Val Arg Ile Lys
            260                 265                 270

Pro Gly Ser Ala Asn Lys Pro Lys Asp Glu Leu Asp Tyr Glu Asn Asp
        275                 280                 285

Ile Glu Lys Lys Ile Cys Lys Met Glu Lys Cys Ser Ser Val Phe Asn
    290                 295                 300

Val Val Asn Ser Ala Ala Val Ala Met Ala Glu Lys Thr Ala Ser Cys
305                 310                 315                 320

Gly Val Trp Asp Glu Trp Ser Pro Cys Ser Val Thr Cys Gly Lys Gly
                325                 330                 335

Thr Arg Ser Arg Lys Arg Glu Ile Leu His Gly Cys Thr Ser Glu
            340                 345                 350

Leu Gln Glu Gln Cys Glu Glu Glu Arg Cys Leu Pro Lys Thr Asn Gly
        355                 360                 365

Ile Arg Tyr His Tyr Asp Glu Tyr Ile His
    370                 375

<210> SEQ ID NO 7
<211> LENGTH: 379
<212> TYPE: PRT
<213> ORGANISM: Plasmodium falciparum

<400> SEQUENCE: 7

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
            20                  25                  30

Gln Glu His Thr Tyr Gln Gln Glu Asp Ser Gly Glu Asp Glu Asn Thr
        35                  40                  45

Leu Gln His Ala Tyr Pro Ile Asp His Glu Gly Ala Glu Pro Ala Pro
    50                  55                  60

Gln Glu Gln Asn Leu Phe Ser Ser Met Ala Phe Arg Gly Asn Asn Gly

```
                65                  70                  75                  80
            His Asp Ser Ser Ser Leu Tyr Gly Gly Ser Gln Phe Ile Glu Gln
                                85                  90                  95

Leu Asp Asn Ser Phe Thr Ser Ala Phe Leu Glu Ser Gln Ser Met Asn
                            100                 105                 110

Lys Ile Gly Asp Asp Leu Ala Glu Thr Ile Ser Asn Glu Leu Val Ser
                        115                 120                 125

Val Leu Gln Lys Asn Ser Pro Thr Phe Leu Glu Ser Ser Phe Asp Ile
            130                 135                 140

Lys Ser Glu Val Lys Lys His Ala Lys Ser Met Leu Lys Glu Leu Ile
            145                 150                 155                 160

Lys Val Gly Leu Pro Ser Phe Glu Asn Leu Val Ala Glu Asn Val Lys
                            165                 170                 175

Pro Pro Lys Val Asp Pro Ala Thr Tyr Gly Ile Ile Val Pro Val Leu
                        180                 185                 190

Thr Ser Leu Phe Asn Lys Val Glu Thr Ala Val Gly Ala Lys Val Ser
                    195                 200                 205

Asp Glu Ile Trp Asn Tyr Asn Ser Pro Asp Val Ser Glu Ser Glu Glu
                210                 215                 220

Ser Leu Ser Asp Asp Phe Phe Asp Ala Ala Gly Pro Ser Asp Lys His
            225                 230                 235                 240

Ile Glu Gln Tyr Leu Lys Lys Ile Gln Asn Ser Leu Ser Thr Glu Trp
                            245                 250                 255

Ser Pro Cys Ser Val Thr Cys Gly Asn Gly Ile Gln Val Arg Ile Lys
                        260                 265                 270

Pro Gly Ser Ala Asn Lys Pro Lys Asp Glu Leu Asp Tyr Glu Asn Asp
                    275                 280                 285

Ile Glu Lys Lys Ile Cys Lys Met Glu Lys Cys Ser Ser Val Phe Asn
                290                 295                 300

Val Val Asn Ser Ala Ala Val Ala Met Ala Glu Lys Thr Ala Ser Cys
            305                 310                 315                 320

Gly Val Trp Asp Glu Trp Ser Pro Cys Ser Val Thr Cys Gly Lys Gly
                            325                 330                 335

Thr Arg Ser Arg Lys Arg Glu Ile Leu His Glu Gly Cys Thr Ser Glu
                        340                 345                 350

Leu Gln Glu Gln Cys Glu Glu Glu Arg Cys Leu Pro Lys Tyr Gly Lys
                    355                 360                 365

Tyr Ile Ala Val Asp Ala Phe Ile Lys Lys Ile
                370                 375

<210> SEQ ID NO 8
<211> LENGTH: 291
<212> TYPE: PRT
<213> ORGANISM: Plasmodium falciparum

<400> SEQUENCE: 8

Phe Arg Gly Asn Asn Gly His Asp Ser Ser Ser Leu Tyr Gly Gly
1               5                   10                  15

Ser Gln Phe Ile Glu Gln Leu Asp Asn Ser Phe Thr Ser Ala Phe Leu
            20                  25                  30

Glu Ser Gln Ser Met Asn Lys Ile Gly Asp Asp Leu Ala Glu Thr Ile
        35                  40                  45

Ser Asn Glu Leu Val Ser Val Leu Gln Lys Asn Ser Pro Thr Phe Leu
    50                  55                  60
```

Glu Ser Ser Phe Asp Ile Lys Ser Glu Val Lys Lys His Ala Lys Ser
65                  70                  75                  80

Met Leu Lys Glu Leu Ile Lys Val Gly Leu Pro Ser Phe Glu Asn Leu
                85                  90                  95

Val Ala Glu Asn Val Lys Pro Pro Lys Val Asp Pro Ala Thr Tyr Gly
            100                 105                 110

Ile Ile Val Pro Val Leu Thr Ser Leu Phe Asn Lys Val Glu Thr Ala
        115                 120                 125

Val Gly Ala Lys Val Ser Asp Glu Ile Trp Asn Tyr Asn Ser Pro Asp
130                 135                 140

Val Ser Glu Ser Glu Ser Leu Ser Asp Asp Phe Phe Asp Ala Ala
145                 150                 155                 160

Gly Pro Ser Asp Lys His Ile Glu Gln Tyr Leu Lys Lys Ile Gln Asn
                165                 170                 175

Ser Leu Ser Thr Glu Trp Ser Pro Cys Ser Val Thr Cys Gly Asn Gly
            180                 185                 190

Ile Gln Val Arg Ile Lys Pro Gly Ser Ala Asn Lys Pro Lys Asp Glu
        195                 200                 205

Leu Asp Tyr Glu Asn Asp Ile Glu Lys Lys Ile Cys Lys Met Glu Lys
210                 215                 220

Cys Ser Ser Val Phe Asn Val Asn Ser Ala Ala Val Ala Met Ala
225                 230                 235                 240

Glu Lys Thr Ala Ser Cys Gly Val Trp Asp Glu Trp Ser Pro Cys Ser
                245                 250                 255

Val Thr Cys Gly Lys Gly Thr Arg Ser Arg Lys Arg Glu Ile Leu His
            260                 265                 270

Glu Gly Cys Thr Ser Glu Leu Gln Glu Gln Cys Glu Glu Arg Cys
        275                 280                 285

Leu Pro Lys
290

<210> SEQ ID NO 9
<211> LENGTH: 304
<212> TYPE: PRT
<213> ORGANISM: Plasmodium falciparum

<400> SEQUENCE: 9

Phe Arg Gly Asn Asn Gly His Asp Ser Ser Ser Ser Leu Tyr Gly Gly
1               5                   10                  15

Ser Gln Phe Ile Glu Gln Leu Asp Asn Ser Phe Thr Ser Ala Phe Leu
                20                  25                  30

Glu Ser Gln Ser Met Asn Lys Ile Gly Asp Asp Leu Ala Glu Thr Ile
            35                  40                  45

Ser Asn Glu Leu Val Ser Leu Gln Lys Asn Ser Pro Thr Phe Leu
        50                  55                  60

Glu Ser Ser Phe Asp Ile Lys Ser Glu Val Lys Lys His Ala Lys Ser
65                  70                  75                  80

Met Leu Lys Glu Leu Ile Lys Val Gly Leu Pro Ser Phe Glu Asn Leu
                85                  90                  95

Val Ala Glu Asn Val Lys Pro Pro Lys Val Asp Pro Ala Thr Tyr Gly
            100                 105                 110

Ile Ile Val Pro Val Leu Thr Ser Leu Phe Asn Lys Val Glu Thr Ala
        115                 120                 125

Val Gly Ala Lys Val Ser Asp Glu Ile Trp Asn Tyr Asn Ser Pro Asp
130                 135                 140

```
Val Ser Glu Ser Glu Glu Ser Leu Ser Asp Asp Phe Phe Asp Ala Ala
145                 150                 155                 160

Gly Pro Ser Asp Lys His Ile Glu Gln Tyr Leu Lys Lys Ile Gln Asn
            165                 170                 175

Ser Leu Ser Thr Glu Trp Ser Pro Cys Ser Val Thr Cys Gly Asn Gly
            180                 185                 190

Ile Gln Val Arg Ile Lys Pro Gly Ser Ala Asn Lys Pro Lys Asp Glu
            195                 200                 205

Leu Asp Tyr Glu Asn Asp Ile Glu Lys Lys Ile Cys Lys Met Glu Lys
            210                 215                 220

Cys Ser Ser Val Phe Asn Val Val Asn Ser Ala Ala Val Ala Met Ala
225                 230                 235                 240

Glu Lys Thr Ala Ser Cys Gly Val Trp Asp Glu Trp Ser Pro Cys Ser
            245                 250                 255

Val Thr Cys Gly Lys Gly Thr Arg Ser Arg Lys Arg Glu Ile Leu His
            260                 265                 270

Glu Gly Cys Thr Ser Glu Leu Gln Glu Gln Cys Glu Glu Glu Arg Cys
            275                 280                 285

Leu Pro Lys Thr Asn Gly Ile Arg Tyr His Tyr Asp Glu Tyr Ile His
            290                 295                 300

<210> SEQ ID NO 10
<211> LENGTH: 305
<212> TYPE: PRT
<213> ORGANISM: Plasmodium falciparum

<400> SEQUENCE: 10

Phe Arg Gly Asn Asn Gly His Asp Ser Ser Ser Leu Tyr Gly Gly
1               5                   10                  15

Ser Gln Phe Ile Glu Gln Leu Asp Asn Ser Phe Thr Ser Ala Phe Leu
            20                  25                  30

Glu Ser Gln Ser Met Asn Lys Ile Gly Asp Asp Leu Ala Glu Thr Ile
            35                  40                  45

Ser Asn Glu Leu Val Ser Val Leu Gln Lys Asn Ser Pro Thr Phe Leu
50                  55                  60

Glu Ser Ser Phe Asp Ile Lys Ser Glu Val Lys Lys His Ala Lys Ser
65                  70                  75                  80

Met Leu Lys Glu Leu Ile Lys Val Gly Leu Pro Ser Phe Glu Asn Leu
            85                  90                  95

Val Ala Glu Asn Val Lys Pro Pro Lys Val Asp Pro Thr Tyr Gly
            100                 105                 110

Ile Ile Val Pro Val Leu Thr Ser Leu Phe Asn Lys Val Glu Thr Ala
            115                 120                 125

Val Gly Ala Lys Val Ser Asp Glu Ile Trp Asn Tyr Asn Ser Pro Asp
            130                 135                 140

Val Ser Glu Ser Glu Glu Ser Leu Ser Asp Asp Phe Phe Asp Ala Ala
145                 150                 155                 160

Gly Pro Ser Asp Lys His Ile Glu Gln Tyr Leu Lys Lys Ile Gln Asn
            165                 170                 175

Ser Leu Ser Thr Glu Trp Ser Pro Cys Ser Val Thr Cys Gly Asn Gly
            180                 185                 190

Ile Gln Val Arg Ile Lys Pro Gly Ser Ala Asn Lys Pro Lys Asp Glu
            195                 200                 205

Leu Asp Tyr Glu Asn Asp Ile Glu Lys Lys Ile Cys Lys Met Glu Lys
```

```
            210                 215                 220
Cys Ser Ser Val Phe Asn Val Asn Ser Ala Ala Val Ala Met Ala
225                 230                 235                 240

Glu Lys Thr Ala Ser Cys Gly Val Trp Asp Glu Trp Ser Pro Cys Ser
                245                 250                 255

Val Thr Cys Gly Lys Gly Thr Arg Ser Arg Lys Arg Glu Ile Leu His
                260                 265                 270

Glu Gly Cys Thr Ser Glu Leu Gln Glu Gln Cys Glu Glu Glu Arg Cys
                275                 280                 285

Leu Pro Lys Tyr Gly Lys Tyr Ile Ala Val Asp Ala Phe Ile Lys Lys
                290                 295                 300

Ile
305

<210> SEQ ID NO 11
<211> LENGTH: 520
<212> TYPE: PRT
<213> ORGANISM: Plasmodium falciparum

<400> SEQUENCE: 11

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
                20                  25                  30

Gln Glu His Thr Tyr Gln Gln Glu Asp Ser Gly Glu Asp Glu Asn Thr
            35                  40                  45

Leu Gln His Ala Tyr Pro Ile Asp His Glu Gly Ala Glu Pro Ala Pro
50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
                100                 105                 110

Val Ala Gly Thr Gln Tyr Arg Leu Pro Ser Gly Lys Cys Pro Val Phe
            115                 120                 125

Gly Lys Gly Ile Ile Ile Glu Asn Ser Gln Thr Thr Phe Leu Thr Pro
130                 135                 140

Val Ala Thr Glu Asn Gln Asp Leu Lys Asp Gly Gly Phe Ala Phe Pro
145                 150                 155                 160

Pro Thr Lys Pro Leu Met Ser Pro Met Thr Leu Asp Gln Met Arg His
                165                 170                 175

Phe Tyr Lys Asp Asn Glu Tyr Val Lys Asn Leu Asp Glu Leu Thr Leu
                180                 185                 190

Cys Ser Arg His Ala Gly Asn Met Asn Pro Asp Asn Asp Lys Asn Ser
            195                 200                 205

Asn Tyr Lys Tyr Pro Ala Val Tyr Asp Asp Lys Asp Lys Lys Cys His
210                 215                 220

Ile Leu Tyr Ile Ala Ala Gln Glu Asn Asn Gly Pro Arg Tyr Cys Asn
225                 230                 235                 240

Lys Asp Glu Ser Lys Arg Asn Ser Met Phe Cys Phe Arg Pro Ala Lys
                245                 250                 255

Asp Lys Ser Phe Gln Asn Tyr Val Tyr Leu Ser Lys Asn Val Val Asp
                260                 265                 270
```

Asn Trp Glu Lys Val Cys Pro Arg Lys Asn Leu Glu Asn Ala Lys Phe
            275                 280                 285

Gly Leu Trp Val Asp Gly Asn Cys Glu Asp Ile Pro His Val Asn Glu
290                 295                 300

Phe Ser Ala Asn Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Lys Asn Ala Asp Met Ile Arg
            340                 345                 350

Ser Ala Phe Leu Pro Thr Gly Ala Phe Lys Ala Asp Arg Tyr Lys Ser
            355                 360                 365

His Gly Lys Gly Tyr Asn Trp Gly Asn Tyr Asn Arg Lys Thr Gln Lys
            370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Ile Glu Val Glu His Asn
                405                 410                 415

Phe Pro Cys Ser Leu Tyr Lys Asp Glu Ile Lys Lys Glu Ile Glu Arg
                420                 425                 430

Glu Ser Lys Arg Ile Lys Leu Asn Asp Asn Asp Glu Gly Asn Lys
            435                 440                 445

Lys Ile Ile Ala Pro Arg Ile Phe Ile Ser Asp Asp Lys Asp Ser Leu
465                 450                 455                 460

Lys Cys Pro Cys Asp Pro Glu Ile Val Ser Gln Ser Thr Cys Asn Phe
465                 470                 475                 480

Phe Val Cys Lys Cys Val Glu Lys Arg Ala Glu Val Thr Ser Asn Asn
            485                 490                 495

Glu Val Val Lys Glu Glu Tyr Lys Asp Glu Tyr Ala Asp Ile Pro
            500                 505                 510

Glu His Lys Pro Thr Tyr Asp Lys
            515                 520

<210> SEQ ID NO 12
<211> LENGTH: 520
<212> TYPE: PRT
<213> ORGANISM: Plasmodium falciparum

<400> SEQUENCE: 12

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
                20                  25                  30

Gln Glu His Thr Tyr Gln Gln Asp Ser Gly Glu Asp Glu Asn Thr
            35                  40                  45

Leu Gln His Ala Tyr Pro Ile Asp His Glu Gly Ala Glu Pro Ala Pro
50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
                100                 105                 110

Val Ala Gly Thr Gln Tyr Arg Leu Pro Ser Gly Lys Cys Pro Val Phe
            115                 120                 125

Gly Lys Gly Ile Ile Glu Asn Ser Gln Thr Thr Phe Leu Lys Pro
130                 135                 140

Val Ala Thr Gly Asn Gln Asp Leu Lys Asp Gly Phe Ala Phe Pro
145                 150                 155                 160

Pro Thr Asn Pro Leu Ile Ser Pro Met Thr Leu Asn Gly Met Arg Asp
                165                 170                 175

Phe Tyr Lys Asn Asn Glu Tyr Val Lys Asn Leu Asp Glu Leu Thr Leu
                180                 185                 190

Cys Ser Arg His Ala Gly Asn Met Asn Pro Asp Asn Asp Glu Asn Ser
        195                 200                 205

Asn Tyr Lys Tyr Pro Ala Val Tyr Asp Tyr Asn Asp Lys Lys Cys His
210                 215                 220

Ile Leu Tyr Ile Ala Ala Gln Glu Asn Asn Gly Pro Arg Tyr Cys Asn
225                 230                 235                 240

Lys Asp Glu Ser Lys Arg Asn Ser Met Phe Cys Phe Arg Pro Ala Lys
                245                 250                 255

Asp Lys Leu Phe Glu Asn Tyr Val Tyr Leu Ser Lys Asn Val Val His
                260                 265                 270

Asn Trp Glu Glu Val Cys Pro Arg Lys Asn Leu Glu Asn Ala Lys Phe
        275                 280                 285

Gly Leu Trp Val Asp Gly Asn Cys Glu Asp Ile Pro His Val Asn Glu
290                 295                 300

Phe Ser Ala Asn Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Asn Lys Asn Ala Asp Met Ile Arg
                340                 345                 350

Ser Ala Phe Leu Pro Thr Gly Ala Phe Lys Ala Asp Arg Tyr Lys Ser
        355                 360                 365

Arg Gly Lys Gly Tyr Asn Trp Gly Asn Tyr Asn Arg Lys Thr Gln Lys
370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Ile Glu Val Glu Asn Asn
                405                 410                 415

Phe Pro Cys Ser Leu Tyr Lys Asn Glu Ile Met Lys Glu Ile Glu Arg
                420                 425                 430

Glu Ser Lys Arg Ile Lys Leu Asn Asp Asn Asp Glu Gly Asn Lys
        435                 440                 445

Lys Ile Ile Ala Pro Arg Ile Phe Ile Ser Asp Asp Lys Asp Ser Leu
450                 455                 460

Lys Cys Pro Cys Asp Pro Glu Met Val Ser Gln Ser Thr Cys Arg Phe
465                 470                 475                 480

Phe Val Cys Lys Cys Val Glu Arg Arg Ala Glu Val Thr Ser Asn Asn
                485                 490                 495

Glu Val Val Lys Glu Glu Tyr Lys Asp Glu Tyr Ala Asp Ile Pro
        500                 505                 510

Glu His Lys Pro Thr Tyr Asp Asn
        515                 520

<210> SEQ ID NO 13
<211> LENGTH: 520

<212> TYPE: PRT
<213> ORGANISM: Plasmodium falciparum

<400> SEQUENCE: 13

```
Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
            20                  25                  30

Gln Glu His Thr Tyr Gln Gln Glu Asp Ser Gly Glu Asp Glu Asn Thr
        35                  40                  45

Leu Gln His Ala Tyr Pro Ile Asp His Glu Gly Ala Glu Pro Ala Pro
    50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
            100                 105                 110

Val Ala Gly Thr Gln Tyr Arg Leu Pro Ser Gly Lys Cys Pro Val Phe
        115                 120                 125

Gly Lys Gly Ile Ile Ile Glu Asn Ser Lys Thr Thr Phe Leu Thr Pro
    130                 135                 140

Val Ala Thr Glu Asn Gln Asp Leu Lys Asp Gly Gly Phe Ala Phe Pro
145                 150                 155                 160

Pro Thr Glu Pro Leu Met Ser Pro Met Thr Leu Asp Asp Met Arg Asp
                165                 170                 175

Leu Tyr Lys Asp Asn Lys Tyr Val Lys Asn Leu Asp Glu Leu Thr Leu
            180                 185                 190

Cys Ser Arg His Ala Gly Asn Met Ile Pro Asp Asn Asp Lys Asn Ser
        195                 200                 205

Asn Tyr Lys Tyr Pro Ala Val Tyr Asp Tyr Glu Asp Lys Lys Cys His
    210                 215                 220

Ile Leu Tyr Ile Ala Ala Gln Glu Asn Asn Gly Pro Arg Tyr Cys Asn
225                 230                 235                 240

Lys Asp Gln Ser Lys Arg Asn Ser Met Phe Cys Phe Arg Pro Ala Lys
                245                 250                 255

Asp Ile Ser Phe Gln Asn Tyr Val Tyr Leu Ser Lys Asn Val Val Asp
            260                 265                 270

Asn Trp Glu Lys Val Cys Pro Arg Lys Asn Leu Gln Asn Ala Lys Phe
        275                 280                 285

Gly Leu Trp Val Asp Gly Asn Cys Glu Asp Ile Pro His Val Asn Glu
    290                 295                 300

Phe Ser Ala Ile Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
                325                 330                 335

Glu Lys Ile Lys Glu Gly Phe Lys Asn Lys Asn Ala Asp Met Ile Arg
            340                 345                 350

Ser Ala Phe Leu Pro Thr Gly Ala Phe Lys Ala Asp Arg Tyr Lys Ser
        355                 360                 365

His Gly Lys Gly Tyr Asn Trp Gly Asn Tyr Asn Thr Glu Thr Gln Lys
    370                 375                 380

Cys Glu Ile Phe Asn Val Lys Pro Thr Cys Leu Ile Asn Asp Lys Ser
385                 390                 395                 400
```

```
Tyr Ile Ala Thr Thr Ala Leu Ser His Pro Asn Glu Val Glu His Asn
                405                 410                 415

Phe Pro Cys Ser Leu Tyr Lys Asp Glu Ile Lys Lys Glu Ile Glu Arg
            420                 425                 430

Glu Ser Lys Arg Ile Lys Leu Asn Asp Asn Asp Glu Gly Asn Lys
        435                 440                 445

Lys Ile Ile Ala Pro Arg Ile Phe Ile Ser Asp Asp Ile Asp Ser Leu
450                 455                 460

Lys Cys Pro Cys Ala Pro Glu Ile Val Ser Gln Ser Thr Cys Asn Phe
465                 470                 475                 480

Phe Val Cys Lys Cys Val Glu Lys Arg Ala Glu Val Thr Ser Asn Asn
                485                 490                 495

Glu Val Val Val Lys Glu Glu Tyr Lys Asp Glu Tyr Ala Asp Ile Pro
                500                 505                 510

Glu His Lys Pro Thr Tyr Asp Lys
            515                 520

<210> SEQ ID NO 14
<211> LENGTH: 622
<212> TYPE: PRT
<213> ORGANISM: Plasmodium falciparum

<400> SEQUENCE: 14

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
                20                  25                  30

Gln Glu His Thr Tyr Gln Gln Glu Asp Ser Gly Glu Asp Glu Asn Thr
            35                  40                  45

Leu Gln His Ala Tyr Pro Ile Asp His Glu Gly Ala Glu Pro Ala Pro
    50                  55                  60

Gln Glu Gln Asn Leu Phe Ser Ser Ile Glu Ile Val Glu Arg Ser Asn
65                  70                  75                  80

Tyr Met Gly Asn Pro Trp Thr Glu Tyr Met Ala Lys Tyr Asp Ile Glu
                85                  90                  95

Glu Val His Gly Ser Gly Ile Arg Val Asp Leu Gly Glu Asp Ala Glu
                100                 105                 110

Val Ala Gly Thr Gln Tyr Arg Leu Pro Ser Gly Lys Cys Pro Val Phe
            115                 120                 125

Gly Lys Gly Ile Ile Ile Glu Asn Ser Gln Thr Thr Phe Leu Thr Pro
130                 135                 140

Val Ala Thr Glu Asn Gln Asp Leu Lys Asp Gly Gly Phe Ala Phe Pro
145                 150                 155                 160

Pro Thr Lys Pro Leu Met Ser Pro Met Thr Leu Asp Gln Met Arg His
                165                 170                 175

Phe Tyr Lys Asp Asn Glu Tyr Val Lys Asn Leu Asp Glu Leu Thr Leu
            180                 185                 190

Cys Ser Arg His Ala Gly Asn Met Asn Pro Asp Asn Asp Lys Asn Ser
        195                 200                 205

Asn Tyr Lys Tyr Pro Ala Val Tyr Asp Asp Lys Asp Lys Lys Cys His
    210                 215                 220

Ile Leu Tyr Ile Ala Ala Gln Glu Asn Asn Gly Pro Arg Tyr Cys Asn
225                 230                 235                 240

Lys Asp Glu Ser Lys Arg Asn Ser Met Phe Cys Phe Arg Pro Ala Lys
```

```
                    245                 250                 255
Asp Lys Ser Phe Gln Asn Tyr Val Tyr Leu Ser Lys Asn Val Val Asp
            260                 265                 270

Asn Trp Glu Lys Val Cys Pro Arg Lys Asn Leu Glu Asn Ala Lys Phe
        275                 280                 285

Gly Leu Trp Val Asp Gly Asn Cys Glu Asp Ile Pro His Val Asn Glu
    290                 295                 300

Phe Ser Ala Asn Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
            325                 330                 335

Glu Lys Ile Lys Glu Gly Phe Lys Asn Lys Asn Ala Asp Met Ile Arg
        340                 345                 350

Ser Ala Phe Leu Pro Thr Gly Ala Phe Lys Ala Asp Arg Tyr Lys Ser
    355                 360                 365

His Gly Lys Gly Tyr Asn Trp Gly Asn Tyr Asn Arg Lys Thr Gln Lys
370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Ile Glu Val Glu His Asn
            405                 410                 415

Phe Pro Cys Ser Leu Tyr Lys Asp Glu Ile Lys Lys Glu Ile Glu Arg
        420                 425                 430

Glu Ser Lys Arg Ile Lys Leu Asn Asp Asn Asp Glu Gly Asn Lys
    435                 440                 445

Lys Ile Ile Ala Pro Arg Ile Phe Ile Ser Asp Asp Lys Asp Ser Leu
450                 455                 460

Lys Cys Pro Cys Asp Pro Glu Ile Val Ser Gln Ser Thr Cys Asn Phe
465                 470                 475                 480

Phe Val Cys Lys Cys Val Glu Lys Arg Ala Glu Val Thr Ser Asn Asn
            485                 490                 495

Glu Val Val Val Lys Glu Glu Tyr Lys Asp Glu Tyr Ala Asp Ile Pro
        500                 505                 510

Glu His Lys Pro Thr Tyr Asp Lys Met Ala Ala Val Ala Met Ala Ile
    515                 520                 525

Ser Gln His Gln Cys Val Lys Lys Gln Cys Pro Glu Asn Ser Gly Cys
530                 535                 540

Phe Arg His Leu Asp Glu Arg Glu Cys Lys Cys Leu Leu Asn Tyr
545                 550                 555                 560

Lys Gln Glu Gly Asp Lys Cys Val Glu Asn Pro Asn Pro Thr Cys Asn
            565                 570                 575

Glu Asn Asn Gly Gly Cys Asp Ala Asp Ala Lys Cys Thr Glu Glu Asp
        580                 585                 590

Ser Gly Ser Asn Gly Lys Lys Ile Thr Cys Glu Cys Thr Lys Pro Asp
    595                 600                 605

Ser Tyr Pro Leu Phe Asp Gly Ile Phe Cys Ser Ser Asn
610                 615                 620
```

<210> SEQ ID NO 15
<211> LENGTH: 640
<212> TYPE: PRT
<213> ORGANISM: Plasmodium falciparum

<400> SEQUENCE: 15

-continued

```
Gln Asn Tyr Trp Glu His Pro Tyr Gln Lys Ser Asp Val Tyr His Pro
1               5                   10                  15
Ile Asn Glu His Arg Glu His Pro Lys Glu Tyr Glu Tyr Pro Leu His
            20                  25                  30
Gln Glu His Thr Tyr Gln Gln Glu Asp Ser Gly Glu Asp Glu Asn Thr
        35                  40                  45
Leu Gln His Ala Tyr Pro Ile Asp His Glu Gly Ala Glu Pro Ala Pro
    50                  55                  60
Gln Glu Gln Asn Leu Phe Ser Ser Ile Glu Ile Val Glu Arg Ser Asn
65                  70                  75                  80
Tyr Met Gly Asn Pro Trp Thr Glu Tyr Met Ala Lys Tyr Asp Ile Glu
                85                  90                  95
Glu Val His Gly Ser Gly Ile Arg Val Asp Leu Gly Glu Asp Ala Glu
            100                 105                 110
Val Ala Gly Thr Gln Tyr Arg Leu Pro Ser Gly Lys Cys Pro Val Phe
        115                 120                 125
Gly Lys Gly Ile Ile Glu Asn Ser Gln Thr Thr Phe Leu Lys Pro
    130                 135                 140
Val Ala Thr Gly Asn Gln Asp Leu Lys Asp Gly Gly Phe Ala Phe Pro
145                 150                 155                 160
Pro Thr Asn Pro Leu Ile Ser Pro Met Thr Leu Asn Gly Met Arg Asp
                165                 170                 175
Phe Tyr Lys Asn Asn Glu Tyr Val Lys Asn Leu Asp Glu Leu Thr Leu
            180                 185                 190
Cys Ser Arg His Ala Gly Asn Met Asn Pro Asp Asn Asp Glu Asn Ser
        195                 200                 205
Asn Tyr Lys Tyr Pro Ala Val Tyr Asp Tyr Asn Asp Lys Lys Cys His
    210                 215                 220
Ile Leu Tyr Ile Ala Ala Gln Glu Asn Asn Gly Pro Arg Tyr Cys Asn
225                 230                 235                 240
Lys Asp Glu Ser Lys Arg Asn Ser Met Phe Cys Phe Arg Pro Ala Lys
                245                 250                 255
Asp Lys Leu Phe Glu Asn Tyr Val Tyr Leu Ser Lys Asn Val Val His
            260                 265                 270
Asn Trp Glu Glu Val Cys Pro Arg Lys Asn Leu Glu Asn Ala Lys Phe
        275                 280                 285
Gly Leu Trp Val Asp Gly Asn Cys Glu Asp Ile Pro His Val Asn Glu
    290                 295                 300
Phe Ser Ala Asn Asp Leu Phe Glu Cys Asn Lys Leu Val Phe Glu Leu
305                 310                 315                 320
Ser Ala Ser Asp Gln Pro Lys Gln Tyr Glu Gln His Leu Thr Asp Tyr
                325                 330                 335
Glu Lys Ile Lys Glu Gly Phe Lys Asn Lys Asn Ala Asp Met Ile Arg
            340                 345                 350
Ser Ala Phe Leu Pro Thr Gly Ala Phe Lys Ala Asp Arg Tyr Lys Ser
        355                 360                 365
Arg Gly Lys Gly Tyr Asn Trp Gly Asn Tyr Asn Arg Lys Thr Gln Lys
    370                 375                 380
Cys Glu Ile Phe Asn Val Lys Pro Thr Cys Leu Ile Asn Asp Lys Ser
385                 390                 395                 400
Tyr Ile Ala Thr Thr Ala Leu Ser His Pro Ile Glu Val Glu Asn Asn
                405                 410                 415
Phe Pro Cys Ser Leu Tyr Lys Asn Glu Ile Met Lys Glu Ile Glu Arg
```

```
                420                 425                 430
Glu Ser Lys Arg Ile Lys Leu Asn Asp Asn Asp Glu Gly Asn Lys
            435                 440                 445
Lys Ile Ile Ala Pro Arg Ile Phe Ile Ser Asp Lys Asp Ser Leu
450                 455                 460
Lys Cys Pro Cys Asp Pro Glu Met Val Ser Gln Ser Thr Cys Arg Phe
465                 470                 475                 480
Phe Val Cys Lys Cys Val Glu Arg Arg Ala Glu Val Thr Ser Asn Asn
                485                 490                 495
Glu Val Val Val Lys Glu Glu Tyr Lys Asp Glu Tyr Ala Asp Ile Pro
            500                 505                 510
Glu His Lys Pro Thr Tyr Asp Asn Met Ala Ala Val Ala Met Ala Lys
            515                 520                 525
Lys Tyr Glu Thr Tyr Val Asp Met Lys Thr Ile Glu Ser Lys Tyr Thr
            530                 535                 540
Thr Val Met Thr Leu Ser Glu His Leu Leu Glu Tyr Ala Met Asp Val
545                 550                 555                 560
Leu Lys Ala Asn Pro Gln Lys Pro Ile Asp Pro Lys Ala Asn Leu Asp
                565                 570                 575
Ser Glu Val Val Lys Leu Gln Ile Lys Ile Asn Glu Lys Ser Asn Glu
            580                 585                 590
Leu Asp Asn Ala Ala Ser Gln Val Lys Thr Leu Ile Ile Ile Met Lys
            595                 600                 605
Ser Phe Tyr Asp Ile Ile Ile Ser Glu Lys Ala Ser Met Asp Glu Met
            610                 615                 620
Glu Lys Lys Glu Leu Ser Leu Asn Asn Tyr Ile Glu Lys Thr Asp Tyr
625                 630                 635                 640

<210> SEQ ID NO 16
<211> LENGTH: 603
<212> TYPE: PRT
<213> ORGANISM: Plasmodium falciparum

<400> SEQUENCE: 16

Gln Asn Tyr Trp Glu His Pro Tyr Gln Lys Ser Asp Val Tyr His Pro
1               5                   10                  15
Ile Asn Glu His Arg Glu His Pro Lys Glu Tyr Glu Tyr Pro Leu His
            20                  25                  30
Gln Glu His Thr Tyr Gln Gln Glu Asp Ser Gly Glu Asp Glu Asn Thr
        35                  40                  45
Leu Gln His Ala Tyr Pro Ile Asp His Glu Gly Ala Glu Pro Ala Pro
    50                  55                  60
Gln Glu Gln Asn Leu Phe Ser Ser Ile Glu Ile Val Glu Arg Ser Asn
65                  70                  75                  80
Tyr Met Gly Asn Pro Trp Thr Glu Tyr Met Ala Lys Tyr Asp Ile Glu
                85                  90                  95
Glu Val His Gly Ser Gly Ile Arg Val Asp Leu Gly Glu Asp Ala Glu
            100                 105                 110
Val Ala Gly Thr Gln Tyr Arg Leu Pro Ser Gly Lys Cys Pro Val Phe
        115                 120                 125
Gly Lys Gly Ile Ile Ile Glu Asn Ser Lys Thr Thr Phe Leu Thr Pro
    130                 135                 140
Val Ala Thr Glu Asn Gln Asp Leu Lys Asp Gly Gly Phe Ala Phe Pro
145                 150                 155                 160
```

-continued

Pro Thr Glu Pro Leu Met Ser Pro Met Thr Leu Asp Asp Met Arg Asp
            165                 170                 175

Leu Tyr Lys Asp Asn Lys Tyr Val Lys Asn Leu Asp Glu Leu Thr Leu
            180                 185                 190

Cys Ser Arg His Ala Gly Asn Met Ile Pro Asp Asn Asp Lys Asn Ser
            195                 200                 205

Asn Tyr Lys Tyr Pro Ala Val Tyr Asp Tyr Glu Asp Lys Lys Cys His
            210                 215                 220

Ile Leu Tyr Ile Ala Ala Gln Glu Asn Asn Gly Pro Arg Tyr Cys Asn
225                 230                 235                 240

Lys Asp Gln Ser Lys Arg Asn Ser Met Phe Cys Phe Arg Pro Ala Lys
            245                 250                 255

Asp Ile Ser Phe Gln Asn Tyr Val Tyr Leu Ser Lys Asn Val Val Asp
            260                 265                 270

Asn Trp Glu Lys Val Cys Pro Arg Lys Asn Leu Gln Asn Ala Lys Phe
            275                 280                 285

Gly Leu Trp Val Asp Gly Asn Cys Glu Asp Ile Pro His Val Asn Glu
            290                 295                 300

Phe Ser Ala Ile Asp Leu Phe Glu Cys Asn Lys Leu Val Phe Glu Leu
305                 310                 315                 320

Ser Ala Ser Asp Gln Pro Lys Gln Tyr Glu Gln His Leu Thr Asp Tyr
            325                 330                 335

Glu Lys Ile Lys Glu Gly Phe Lys Asn Lys Asn Ala Asp Met Ile Arg
            340                 345                 350

Ser Ala Phe Leu Pro Thr Gly Ala Phe Lys Ala Asp Arg Tyr Lys Ser
            355                 360                 365

His Gly Lys Gly Tyr Asn Trp Gly Asn Tyr Asn Thr Glu Thr Gln Lys
            370                 375                 380

Cys Glu Ile Phe Asn Val Lys Pro Thr Cys Leu Ile Asn Asp Lys Ser
385                 390                 395                 400

Tyr Ile Ala Thr Thr Ala Leu Ser His Pro Asn Glu Val Glu His Asn
            405                 410                 415

Phe Pro Cys Ser Leu Tyr Lys Asp Glu Ile Lys Lys Glu Ile Glu Arg
            420                 425                 430

Glu Ser Lys Arg Ile Lys Leu Asn Asp Asn Asp Glu Gly Asn Lys
            435                 440                 445

Lys Ile Ile Ala Pro Arg Ile Phe Ile Ser Asp Asp Ile Asp Ser Leu
            450                 455                 460

Lys Cys Pro Cys Ala Pro Glu Ile Val Ser Gln Ser Thr Cys Asn Phe
465                 470                 475                 480

Phe Val Cys Lys Cys Val Glu Lys Arg Ala Glu Val Thr Ser Asn Asn
            485                 490                 495

Glu Val Val Lys Glu Glu Tyr Lys Asp Glu Tyr Ala Asp Ile Pro
            500                 505                 510

Glu His Lys Pro Thr Tyr Asp Lys Met Ala Ala Gly Tyr Cys Lys Asp
            515                 520                 525

Ile Asn Cys Lys Glu Asn Glu Glu Cys Ser Ile Val Asn Phe Lys Pro
            530                 535                 540

Glu Cys Val Cys Lys Glu Asn Leu Lys Lys Asn Asn Lys Gly Glu Cys
545                 550                 555                 560

Ile Ala Ala Ser Cys Leu Ile Asn Glu Gly Asn Cys Pro Lys Asp Ser
            565                 570                 575

Lys Cys Ile Tyr Arg Glu Tyr Lys Pro His Glu Cys Val Cys Asn Lys

-continued

```
                580                 585                 590
        Gln Gly His Val Ala Val Asn Gly Lys Cys Val
                    595                 600

<210> SEQ ID NO 17
<211> LENGTH: 448
<212> TYPE: PRT
<213> ORGANISM: Plasmodium falciparum

<400> SEQUENCE: 17

Ile Glu Ile Val Glu Arg Ser Asn Tyr Met Gly Asn Pro Trp Thr Glu
1               5                   10                  15

Tyr Met Ala Lys Tyr Asp Ile Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Glu Asn
    50                  55                  60

Ser Gln Thr Thr Phe Leu Thr Pro Val Ala Thr Glu Asn Gln Asp Leu
65                  70                  75                  80

Lys Asp Gly Gly Phe Ala Phe Pro Pro Thr Lys Pro Leu Met Ser Pro
                85                  90                  95

Met Thr Leu Asp Gln Met Arg His Phe Tyr Lys Asp Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Lys Asn Ser Asn Tyr Lys Tyr Pro Ala Val Tyr
    130                 135                 140

Asp Asp Lys Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Ser Phe Gln Asn Tyr Val
            180                 185                 190

Tyr Leu Ser Lys Asn Val Val Asp Asn Trp Glu Lys Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Arg Ser Ala Phe Leu Pro Thr Gly Ala
        275                 280                 285

Phe Lys Ala Asp Arg Tyr Lys Ser His Gly Lys Gly Tyr Asn Trp Gly
    290                 295                 300

Asn Tyr Asn Arg Lys Thr Gln Lys Cys Glu Ile Phe Asn Val Lys Pro
305                 310                 315                 320

Thr Cys Leu Ile Asn Asp Lys Ser Tyr Ile Ala Thr Ala Leu Ser
                325                 330                 335

His Pro Ile Glu Val Glu His Asn Phe Pro Cys Ser Leu Tyr Lys Asp
            340                 345                 350
```

-continued

```
Glu Ile Lys Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
        370                 375                 380

Ile Ser Asp Asp Lys Asp Ser Leu Lys Cys Pro Cys Asp Pro Glu Ile
385                 390                 395                 400

Val Ser Gln Ser Thr Cys Asn Phe Phe Val Cys Lys Cys Val Glu Lys
                405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
        435                 440                 445
```

<210> SEQ ID NO 18
<211> LENGTH: 448
<212> TYPE: PRT
<213> ORGANISM: Plasmodium falciparum

<400> SEQUENCE: 18

```
Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Gln Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Ile Ser Pro
                85                  90                  95

Met Thr Leu Asn Gly Met Arg Asp Phe Tyr Lys Asn Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Glu Asn Ser Asn Tyr Lys Tyr Pro Ala Val Tyr
    130                 135                 140

Asp Tyr Asn Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Leu Phe Glu Asn Tyr Val
            180                 185                 190

Tyr Leu Ser Lys Asn Val Val His Asn Trp Glu Glu Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Arg Ser Ala Phe Leu Pro Thr Gly Ala
        275                 280                 285
```

```
Phe Lys Ala Asp Arg Tyr Lys Ser Arg Gly Lys Gly Tyr Asn Trp Gly
        290                 295                 300

Asn Tyr Asn Arg Lys Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Ile Glu Val Glu Asn Asn Phe Pro Cys Ser Leu Tyr Lys Asn
            340                 345                 350

Glu Ile Met Lys Glu Ile Glu Arg Glu Ser Lys Arg Ile Lys Leu Asn
        355                 360                 365

Asp Asn Asp Asp Glu Gly Asn Lys Lys Ile Ile Ala Pro Arg Ile Phe
    370                 375                 380

Ile Ser Asp Asp Lys Asp Ser Leu Lys Cys Pro Cys Asp Pro Glu Met
385                 390                 395                 400

Val Ser Gln Ser Thr Cys Arg Phe Phe Val Cys Lys Cys Val Glu Arg
                405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Asn
        435                 440                 445

<210> SEQ ID NO 19
<211> LENGTH: 448
<212> TYPE: PRT
<213> ORGANISM: Plasmodium falciparum

<400> SEQUENCE: 19

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Lys Thr Thr Phe Leu Thr Pro Val Ala Thr Glu Asn Gln Asp Leu
65              70                  75                  80

Lys Asp Gly Gly Phe Ala Phe Pro Pro Thr Glu Pro Leu Met Ser Pro
            85                  90                  95

Met Thr Leu Asp Asp Met Arg Asp Leu Tyr Lys Asp Asn Lys Tyr Val
            100                 105                 110

Lys Asn Leu Asp Glu Leu Thr Leu Cys Ser Arg His Ala Gly Asn Met
        115                 120                 125

Ile Pro Asp Asn Asp Lys Asn Ser Asn Tyr Lys Tyr Pro Ala Val Tyr
    130                 135                 140

Asp Tyr Glu Asp Lys Lys Cys His Ile Leu Tyr Ile Ala Ala Gln Glu
145                 150                 155                 160

Asn Asn Gly Pro Arg Tyr Cys Asn Lys Asp Gln Ser Lys Arg Asn Ser
                165                 170                 175

Met Phe Cys Phe Arg Pro Ala Lys Asp Ile Ser Phe Gln Asn Tyr Val
            180                 185                 190

Tyr Leu Ser Lys Asn Val Val Asp Asn Trp Glu Lys Val Cys Pro Arg
        195                 200                 205

Lys Asn Leu Gln Asn Ala Lys Phe Gly Leu Trp Val Asp Gly Asn Cys
```

```
            210                 215                 220
Glu Asp Ile Pro His Val Asn Glu Phe Ser Ala Ile Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
                    260                 265                 270

Asn Lys Asn Ala Asp Met Ile Arg Ser Ala Phe Leu Pro Thr Gly Ala
                275                 280                 285

Phe Lys Ala Asp Arg Tyr Lys Ser His Gly Lys Gly Tyr Asn Trp Gly
                290                 295                 300

Asn Tyr Asn Thr Glu Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                    325                 330                 335

His Pro Asn Glu Val Glu His Asn Phe Pro Cys Ser Leu Tyr Lys Asp
                340                 345                 350

Glu Ile Lys Lys Glu Ile Glu Arg Glu Ser Lys Arg Ile Lys Leu Asn
                355                 360                 365

Asp Asn Asp Asp Glu Gly Asn Lys Lys Ile Ile Ala Pro Arg Ile Phe
370                 375                 380

Ile Ser Asp Asp Ile Asp Ser Leu Lys Cys Pro Cys Ala Pro Glu Ile
385                 390                 395                 400

Val Ser Gln Ser Thr Cys Asn Phe Phe Val Cys Lys Cys Val Glu Lys
                405                 410                 415

Arg Ala Glu Val Thr Ser Asn Asn Glu Val Val Lys Glu Glu Tyr
                420                 425                 430

Lys Asp Glu Tyr Ala Asp Ile Pro Glu His Lys Pro Thr Tyr Asp Lys
                435                 440                 445

<210> SEQ ID NO 20
<211> LENGTH: 550
<212> TYPE: PRT
<213> ORGANISM: Plasmodium falciparum

<400> SEQUENCE: 20

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
                20                  25                  30

Val Asp Leu Gly Glu Asp Ala Glu Val Ala Gly Thr Gln Tyr Arg Leu
            35                  40                  45

Pro Ser Gly Lys Cys Pro Val Phe Gly Lys Gly Ile Ile Ile Glu Asn
        50                  55                  60

Ser Gln Thr Thr Phe Leu Thr Pro Val Ala Thr Glu Asn Gln Asp Leu
65              70                  75                  80

Lys Asp Gly Gly Phe Ala Phe Pro Pro Thr Lys Pro Leu Met Ser Pro
                85                  90                  95

Met Thr Leu Asp Gln Met Arg His Phe Tyr Lys Asp Asn Glu Tyr Val
                100                 105                 110

Lys Asn Leu Asp Glu Leu Thr Leu Cys Ser Arg His Ala Gly Asn Met
            115                 120                 125

Asn Pro Asp Asn Asp Lys Asn Ser Asn Tyr Lys Tyr Pro Ala Val Tyr
        130                 135                 140
```

```
Asp Asp Lys Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
            165                 170                 175

Met Phe Cys Phe Arg Pro Ala Lys Asp Lys Ser Phe Gln Asn Tyr Val
            180                 185                 190

Tyr Leu Ser Lys Asn Val Val Asp Asn Trp Glu Lys Val Cys Pro Arg
            195                 200                 205

Lys Asn Leu Glu Asn Ala Lys Phe Gly Leu Trp Val Asp Gly Asn Cys
            210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
            245                 250                 255

Tyr Glu Gln His Leu Thr Asp Tyr Glu Lys Ile Lys Glu Gly Phe Lys
            260                 265                 270

Asn Lys Asn Ala Asp Met Ile Arg Ser Ala Phe Leu Pro Thr Gly Ala
            275                 280                 285

Phe Lys Ala Asp Arg Tyr Lys Ser His Gly Lys Gly Tyr Asn Trp Gly
290                 295                 300

Asn Tyr Asn Arg Lys Thr Gln Lys Cys Glu Ile Phe Asn Val Lys Pro
305                 310                 315                 320

Thr Cys Leu Ile Asn Asp Lys Ser Tyr Ile Ala Thr Ala Leu Ser
            325                 330                 335

His Pro Ile Glu Val Glu His Asn Phe Pro Cys Ser Leu Tyr Lys Asp
            340                 345                 350

Glu Ile Lys Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
            370                 375                 380

Ile Ser Asp Asp Lys Asp Ser Leu Lys Cys Pro Cys Asp Pro Glu Ile
385                 390                 395                 400

Val Ser Gln Ser Thr Cys Asn Phe Phe Val Cys Lys Cys Val Glu Lys
            405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
            435                 440                 445

Met Ala Ala Val Ala Met Ala Ile Ser Gln His Gln Cys Val Lys Lys
            450                 455                 460

Gln Cys Pro Glu Asn Ser Gly Cys Phe Arg His Leu Asp Glu Arg Glu
465                 470                 475                 480

Glu Cys Lys Cys Leu Leu Asn Tyr Lys Gln Glu Gly Asp Lys Cys Val
            485                 490                 495

Glu Asn Pro Asn Pro Thr Cys Asn Glu Asn Gly Gly Cys Asp Ala
            500                 505                 510

Asp Ala Lys Cys Thr Glu Glu Asp Ser Gly Ser Asn Gly Lys Lys Ile
            515                 520                 525

Thr Cys Glu Cys Thr Lys Pro Asp Ser Tyr Pro Leu Phe Asp Gly Ile
            530                 535                 540

Phe Cys Ser Ser Ser Asn
545                 550
```

<210> SEQ ID NO 21
<211> LENGTH: 568
<212> TYPE: PRT
<213> ORGANISM: Plasmodium falciparum

<400> SEQUENCE: 21

```
Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Gln Thr Thr Phe Leu Lys Pro Val Ala Thr Gly Asn Gln Asp Leu
65                  70                  75                  80

Lys Asp Gly Gly Phe Ala Phe Pro Pro Thr Asn Pro Leu Ile Ser Pro
                85                  90                  95

Met Thr Leu Asn Gly Met Arg Asp Phe Tyr Lys Asn Asn Glu Tyr Val
            100                 105                 110

Lys Asn Leu Asp Glu Leu Thr Leu Cys Ser Arg His Ala Gly Asn Met
        115                 120                 125

Asn Pro Asp Asn Asp Glu Asn Ser Asn Tyr Lys Tyr Pro Ala Val Tyr
    130                 135                 140

Asp Tyr Asn Asp Lys Lys Cys His Ile Leu Tyr Ile Ala Ala Gln Glu
145                 150                 155                 160

Asn Asn Gly Pro Arg Tyr Cys Asn Lys Asp Glu Ser Lys Arg Asn Ser
                165                 170                 175

Met Phe Cys Phe Arg Pro Ala Lys Asp Lys Leu Phe Glu Asn Tyr Val
            180                 185                 190

Tyr Leu Ser Lys Asn Val Val His Asn Trp Glu Glu Val Cys Pro Arg
        195                 200                 205

Lys Asn Leu Glu Asn Ala Lys Phe Gly Leu Trp Val Asp Gly Asn Cys
    210                 215                 220

Glu Asp Ile Pro His Val Asn Glu Phe Ser Ala Asn Asp Leu Phe Glu
225                 230                 235                 240

Cys Asn Lys Leu Val Phe Glu Leu Ser Ala Ser Asp Gln Pro Lys Gln
                245                 250                 255

Tyr Glu Gln His Leu Thr Asp Tyr Glu Lys Ile Lys Glu Gly Phe Lys
            260                 265                 270

Asn Lys Asn Ala Asp Met Ile Arg Ser Ala Phe Leu Pro Thr Gly Ala
        275                 280                 285

Phe Lys Ala Asp Arg Tyr Lys Ser Arg Gly Lys Gly Tyr Asn Trp Gly
    290                 295                 300

Asn Tyr Asn Arg Lys Thr Gln Lys Cys Glu Ile Phe Asn Val Lys Pro
305                 310                 315                 320

Thr Cys Leu Ile Asn Asp Lys Ser Tyr Ile Ala Thr Thr Ala Leu Ser
                325                 330                 335

His Pro Ile Glu Val Glu Asn Asn Phe Pro Cys Ser Leu Tyr Lys Asn
            340                 345                 350

Glu Ile Met Lys Glu Ile Glu Arg Glu Ser Lys Arg Ile Lys Leu Asn
        355                 360                 365

Asp Asn Asp Asp Glu Gly Asn Lys Lys Ile Ile Ala Pro Arg Ile Phe
    370                 375                 380
```

```
Ile Ser Asp Asp Lys Asp Ser Leu Lys Cys Pro Cys Asp Pro Glu Met
385                 390                 395                 400

Val Ser Gln Ser Thr Cys Arg Phe Phe Val Cys Lys Cys Val Glu Arg
                405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Asn
                435                 440                 445

Met Ala Val Ala Met Ala Lys Lys Tyr Glu Thr Tyr Val Asp Met
            450                 455                 460

Lys Thr Ile Glu Ser Lys Tyr Thr Thr Val Met Thr Leu Ser Glu His
465                 470                 475                 480

Leu Leu Glu Tyr Ala Met Asp Val Leu Lys Ala Asn Pro Gln Lys Pro
                485                 490                 495

Ile Asp Pro Lys Ala Asn Leu Asp Ser Glu Val Val Lys Leu Gln Ile
                500                 505                 510

Lys Ile Asn Glu Lys Ser Asn Glu Leu Asp Asn Ala Ala Ser Gln Val
                515                 520                 525

Lys Thr Leu Ile Ile Ile Met Lys Ser Phe Tyr Asp Ile Ile Ile Ser
530                 535                 540

Glu Lys Ala Ser Met Asp Glu Met Gly Lys Lys Glu Leu Ser Leu Asn
545                 550                 555                 560

Asn Tyr Ile Glu Lys Thr Asp Tyr
                565

<210> SEQ ID NO 22
<211> LENGTH: 531
<212> TYPE: PRT
<213> ORGANISM: Plasmodium falciparum

<400> SEQUENCE: 22

Ile Glu Ile Val Glu Arg Ser Asn Tyr Met Gly Asn Pro Trp Thr Glu
1               5                   10                  15

Tyr Met Ala Lys Tyr Asp Ile Glu Glu Val His Gly Ser Gly Ile Arg
            20                  25                  30

Val Asp Leu Gly Glu Asp Ala Glu Val Ala Gly Thr Gln Tyr Arg Leu
        35                  40                  45

Pro Ser Gly Lys Cys Pro Val Phe Gly Lys Gly Ile Ile Ile Glu Asn
    50                  55                  60

Ser Lys Thr Thr Phe Leu Thr Pro Val Ala Thr Glu Asn Gln Asp Leu
65              70                  75                  80

Lys Asp Gly Gly Phe Ala Phe Pro Pro Thr Glu Pro Leu Met Ser Pro
            85                  90                  95

Met Thr Leu Asp Asp Met Arg Asp Leu Tyr Lys Asp Asn Lys Tyr Val
                100                 105                 110

Lys Asn Leu Asp Glu Leu Thr Leu Cys Ser Arg His Ala Gly Asn Met
            115                 120                 125

Ile Pro Asp Asn Asp Lys Asn Ser Asn Tyr Lys Tyr Pro Ala Val Tyr
                130                 135                 140

Asp Tyr Glu Asp Lys Lys Cys His Ile Leu Tyr Ile Ala Ala Gln Glu
145                 150                 155                 160

Asn Asn Gly Pro Arg Tyr Cys Asn Lys Asp Gln Ser Lys Arg Asn Ser
                165                 170                 175

Met Phe Cys Phe Arg Pro Ala Lys Asp Ile Ser Phe Gln Asn Tyr Val
                180                 185                 190
```

Tyr Leu Ser Lys Asn Val Val Asp Asn Trp Glu Lys Val Cys Pro Arg
            195                 200                 205

Lys Asn Leu Gln Asn Ala Lys Phe Gly Leu Trp Val Asp Gly Asn Cys
            210                 215                 220

Glu Asp Ile Pro His Val Asn Glu Phe Ser Ala Ile Asp Leu Phe Glu
225                 230                 235                 240

Cys Asn Lys Leu Val Phe Glu Leu Ser Ala Ser Asp Gln Pro Lys Gln
            245                 250                 255

Tyr Glu Gln His Leu Thr Asp Tyr Glu Lys Ile Lys Glu Gly Phe Lys
            260                 265                 270

Asn Lys Asn Ala Asp Met Ile Arg Ser Ala Phe Leu Pro Thr Gly Ala
            275                 280                 285

Phe Lys Ala Asp Arg Tyr Lys Ser His Gly Lys Gly Tyr Asn Trp Gly
            290                 295                 300

Asn Tyr Asn Thr Glu Thr Gln Lys Cys Glu Ile Phe Asn Val Lys Pro
305                 310                 315                 320

Thr Cys Leu Ile Asn Asp Lys Ser Tyr Ile Ala Thr Ala Leu Ser
            325                 330                 335

His Pro Asn Glu Val Glu His Asn Phe Pro Cys Ser Leu Tyr Lys Asp
            340                 345                 350

Glu Ile Lys Lys Glu Ile Glu Arg Glu Ser Lys Arg Ile Lys Leu Asn
            355                 360                 365

Asp Asn Asp Asp Glu Gly Asn Lys Lys Ile Ile Ala Pro Arg Ile Phe
            370                 375                 380

Ile Ser Asp Asp Ile Asp Ser Leu Lys Cys Pro Cys Ala Pro Glu Ile
385                 390                 395                 400

Val Ser Gln Ser Thr Cys Asn Phe Phe Val Cys Lys Cys Val Glu Lys
            405                 410                 415

Arg Ala Glu Val Thr Ser Asn Asn Glu Val Val Lys Glu Glu Tyr
            420                 425                 430

Lys Asp Glu Tyr Ala Asp Ile Pro Glu His Lys Pro Thr Tyr Asp Lys
            435                 440                 445

Met Ala Ala Gly Tyr Cys Lys Asp Ile Asn Cys Lys Glu Asn Glu Glu
            450                 455                 460

Cys Ser Ile Val Asn Phe Lys Pro Glu Cys Val Cys Lys Glu Asn Leu
465                 470                 475                 480

Lys Lys Asn Asn Lys Gly Glu Cys Ile Ala Ala Ser Cys Leu Ile Asn
            485                 490                 495

Glu Gly Asn Cys Pro Lys Asp Ser Lys Cys Ile Tyr Arg Glu Tyr Lys
            500                 505                 510

Pro His Glu Cys Val Cys Asn Lys Gln Gly His Val Ala Val Asn Gly
            515                 520                 525

Lys Cys Val
            530

<210> SEQ ID NO 23
<211> LENGTH: 389
<212> TYPE: PRT
<213> ORGANISM: Plasmodium falciparum

<400> SEQUENCE: 23

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His

```
            20                  25                  30
Gln Glu His Thr Tyr Gln Gln Glu Asp Ser Gly Glu Asp Glu Asn Thr
         35                  40                  45

Leu Gln His Ala Tyr Pro Ile Asp His Glu Gly Ala Glu Pro Ala Pro
 50                  55                  60

Gln Glu Gln Asn Leu Phe Ser Ser Met Val Thr Val Asp Thr Val Cys
 65                  70                  75                  80

Lys Arg Gly Phe Leu Ile Gln Met Ser Gly His Leu Glu Cys Lys Cys
                 85                  90                  95

Glu Asn Asp Leu Val Leu Val Asn Glu Glu Thr Cys Glu Glu Lys Val
                100                 105                 110

Leu Lys Cys Asp Glu Lys Thr Val Asn Lys Pro Cys Gly Asp Phe Ser
                115                 120                 125

Lys Cys Ile Lys Ile Asp Gly Asn Pro Val Ser Tyr Ala Cys Lys Cys
                130                 135                 140

Asn Leu Gly Tyr Asp Met Val Asn Asn Val Cys Ile Pro Asn Glu Cys
145                 150                 155                 160

Lys Asn Val Ala Cys Gly Asn Gly Lys Cys Ile Leu Asp Thr Ser Asn
                165                 170                 175

Pro Val Lys Thr Gly Val Cys Ser Cys Asn Ile Gly Lys Val Pro Asn
                180                 185                 190

Val Gln Asp Gln Lys Cys Ser Lys Asp Gly Glu Thr Lys Cys Ser Leu
                195                 200                 205

Lys Cys Leu Lys Glu Asn Glu Ala Cys Lys Ala Val Asp Gly Ile Tyr
                210                 215                 220

Lys Cys Asp Cys Lys Asp Gly Phe Ile Ile Asp Asn Glu Ala Ser Ile
225                 230                 235                 240

Cys Thr Ala Ala Val Glu Tyr Val Asp Glu Lys Glu Arg Gln Gly Glu
                245                 250                 255

Ile Tyr Pro Phe Gly Asp Glu Glu Lys Asp Glu Gly Gly Glu Ser
                260                 265                 270

Phe Thr Tyr Glu Lys Ser Glu Val Asp Lys Thr Asp Leu Phe Lys Phe
                275                 280                 285

Ile Glu Gly Gly Glu Gly Asp Asp Val Tyr Lys Val Asp Gly Ser Lys
                290                 295                 300

Val Leu Leu Asp Asp Thr Ile Ser Arg Val Ser Lys Lys His Thr
305                 310                 315                 320

Ala Arg Asp Gly Glu Tyr Gly Glu Tyr Gly Glu Ala Val Glu Asp Gly
                325                 330                 335

Glu Asn Val Ile Lys Ile Ile Arg Ser Val Leu Gln Ser Gly Ala Leu
                340                 345                 350

Pro Ser Val Gly Val Asp Glu Leu Asp Lys Ile Asp Leu Ser Tyr Glu
                355                 360                 365

Thr Thr Glu Ser Gly Asp Thr Ala Val Ser Glu Asp Ser Tyr Asp Lys
                370                 375                 380

Tyr Ala Ser Asn Asn
385

<210> SEQ ID NO 24
<211> LENGTH: 401
<212> TYPE: PRT
<213> ORGANISM: Plasmodium falciparum

<400> SEQUENCE: 24
```

```
Gln Asn Tyr Trp Glu His Pro Tyr Gln Lys Ser Asp Val Tyr His Pro
  1               5                  10                  15

Ile Asn Glu His Arg Glu His Pro Lys Glu Tyr Glu Tyr Pro Leu His
                 20                  25                  30

Gln Glu His Thr Tyr Gln Gln Glu Asp Ser Gly Glu Asp Glu Asn Thr
             35                  40                  45

Leu Gln His Ala Tyr Pro Ile Asp His Glu Gly Ala Glu Pro Ala Pro
 50                  55                  60

Gln Glu Gln Asn Leu Phe Ser Ser Met Val Thr Val Asp Thr Val Cys
 65                  70                  75                  80

Lys Arg Gly Phe Leu Ile Gln Met Ser Gly His Leu Glu Cys Lys Cys
                 85                  90                  95

Glu Asn Asp Leu Val Leu Val Asn Glu Glu Thr Cys Glu Glu Lys Val
                100                 105                 110

Leu Lys Cys Asp Glu Lys Thr Val Asn Lys Pro Cys Gly Asp Phe Ser
                115                 120                 125

Lys Cys Ile Lys Ile Asp Gly Asn Pro Val Ser Tyr Ala Cys Lys Cys
130                 135                 140

Asn Leu Gly Tyr Asp Met Val Asn Asn Val Cys Ile Pro Asn Glu Cys
145                 150                 155                 160

Lys Asn Val Ala Cys Gly Asn Gly Lys Cys Ile Leu Asp Thr Ser Asn
                165                 170                 175

Pro Val Lys Thr Gly Val Cys Ser Cys Asn Ile Gly Lys Val Pro Asn
                180                 185                 190

Val Gln Asp Gln Lys Cys Ser Lys Asp Gly Glu Thr Lys Cys Ser Leu
    195                 200                 205

Lys Cys Leu Lys Glu Asn Glu Ala Cys Lys Ala Val Asp Gly Ile Tyr
    210                 215                 220

Lys Cys Asp Cys Lys Asp Gly Phe Ile Ile Asp Asn Glu Ala Ser Ile
225                 230                 235                 240

Cys Thr Ala Ala Val Glu Tyr Val Asp Glu Lys Glu Arg Gln Gly Glu
                245                 250                 255

Ile Tyr Pro Phe Gly Asp Glu Glu Lys Asp Glu Gly Gly Glu Ser
                260                 265                 270

Phe Thr Tyr Glu Lys Ser Glu Val Asp Lys Thr Asp Leu Phe Lys Phe
                275                 280                 285

Ile Glu Gly Gly Glu Gly Asp Asp Val Tyr Lys Val Asp Gly Ser Lys
                290                 295                 300

Val Leu Leu Asp Asp Asp Thr Ile Ser Arg Val Ser Lys Lys His Thr
305                 310                 315                 320

Ala Arg Asp Gly Glu Tyr Gly Glu Tyr Gly Glu Ala Val Glu Asp Gly
                325                 330                 335

Glu Asn Val Ile Lys Ile Ile Arg Ser Val Leu Gln Ser Gly Ala Leu
                340                 345                 350

Pro Ser Val Gly Val Asp Glu Leu Asp Lys Ile Asp Leu Ser Tyr Glu
                355                 360                 365

Thr Thr Glu Ser Gly Asp Thr Ala Val Ser Glu Asp Ser Tyr Asp Lys
370                 375                 380

Tyr Ala Ser Asn Asn Asn Gly Ile Arg Tyr His Tyr Asp Glu Tyr Ile
385                 390                 395                 400

His

<210> SEQ ID NO 25
```

<211> LENGTH: 403
<212> TYPE: PRT
<213> ORGANISM: Plasmodium falciparum

<400> SEQUENCE: 25

Gln Asn Tyr Trp Glu His Pro Tyr Gln Lys Ser Asp Val Tyr His Pro
1               5                   10                  15

Ile Asn Glu His Arg Glu His Pro Lys Glu Tyr Glu Tyr Pro Leu His
            20                  25                  30

Gln Glu His Thr Tyr Gln Gln Glu Asp Ser Gly Glu Asp Glu Asn Thr
        35                  40                  45

Leu Gln His Ala Tyr Pro Ile Asp His Glu Gly Ala Glu Pro Ala Pro
    50                  55                  60

Gln Glu Gln Asn Leu Phe Ser Ser Met Val Thr Val Asp Thr Val Cys
65                  70                  75                  80

Lys Arg Gly Phe Leu Ile Gln Met Ser Gly His Leu Glu Cys Lys Cys
                85                  90                  95

Glu Asn Asp Leu Val Leu Val Asn Glu Glu Thr Cys Glu Glu Lys Val
            100                 105                 110

Leu Lys Cys Asp Glu Lys Thr Val Asn Lys Pro Cys Gly Asp Phe Ser
        115                 120                 125

Lys Cys Ile Lys Ile Asp Gly Asn Pro Val Ser Tyr Ala Cys Lys Cys
    130                 135                 140

Asn Leu Gly Tyr Asp Met Val Asn Asn Val Cys Ile Pro Asn Glu Cys
145                 150                 155                 160

Lys Asn Val Ala Cys Gly Asn Gly Lys Cys Ile Leu Asp Thr Ser Asn
                165                 170                 175

Pro Val Lys Thr Gly Val Cys Ser Cys Asn Ile Gly Lys Val Pro Asn
            180                 185                 190

Val Gln Asp Gln Lys Cys Ser Lys Asp Gly Glu Thr Lys Cys Ser Leu
        195                 200                 205

Lys Cys Leu Lys Glu Asn Glu Ala Cys Lys Ala Val Asp Gly Ile Tyr
    210                 215                 220

Lys Cys Asp Cys Lys Asp Gly Phe Ile Ile Asp Asn Glu Ala Ser Ile
225                 230                 235                 240

Cys Thr Ala Ala Val Glu Tyr Val Asp Glu Lys Glu Arg Gln Gly Glu
                245                 250                 255

Ile Tyr Pro Phe Gly Asp Glu Glu Lys Asp Glu Gly Glu Ser
            260                 265                 270

Phe Thr Tyr Glu Lys Ser Glu Val Asp Lys Thr Asp Leu Phe Lys Phe
        275                 280                 285

Ile Glu Gly Gly Glu Gly Asp Asp Val Tyr Lys Val Asp Gly Ser Lys
    290                 295                 300

Val Leu Leu Asp Asp Asp Thr Ile Ser Arg Val Ser Lys Lys His Thr
305                 310                 315                 320

Ala Arg Asp Gly Glu Tyr Gly Tyr Gly Glu Ala Val Glu Asp Gly
                325                 330                 335

Glu Asn Val Ile Lys Ile Ile Arg Ser Val Leu Gln Ser Gly Ala Leu
            340                 345                 350

Pro Ser Val Gly Val Asp Glu Leu Asp Lys Ile Asp Leu Ser Tyr Glu
        355                 360                 365

Thr Thr Glu Ser Gly Asp Thr Ala Val Ser Glu Asp Ser Tyr Asp Lys
    370                 375                 380

Tyr Ala Ser Asn Asn Tyr Gly Lys Tyr Ile Ala Val Asp Ala Phe Ile

```
                      385                 390                 395                 400

Lys Lys Ile

<210> SEQ ID NO 26
<211> LENGTH: 316
<212> TYPE: PRT
<213> ORGANISM: Plasmodium falciparum

<400> SEQUENCE: 26

Val Thr Val Asp Thr Val Cys Lys Arg Gly Phe Leu Ile Gln Met Ser
1               5                   10                  15

Gly His Leu Glu Cys Lys Cys Glu Asn Asp Leu Val Leu Val Asn Glu
            20                  25                  30

Glu Thr Cys Glu Glu Lys Val Leu Lys Cys Asp Glu Lys Thr Val Asn
        35                  40                  45

Lys Pro Cys Gly Asp Phe Ser Lys Cys Ile Lys Ile Asp Gly Asn Pro
    50                  55                  60

Val Ser Tyr Ala Cys Lys Cys Asn Leu Gly Tyr Asp Met Val Asn Asn
65                  70                  75                  80

Val Cys Ile Pro Asn Glu Cys Lys Asn Val Ala Cys Gly Asn Gly Lys
                85                  90                  95

Cys Ile Leu Asp Thr Ser Asn Pro Val Lys Thr Gly Val Cys Ser Cys
            100                 105                 110

Asn Ile Gly Lys Val Pro Asn Val Gln Asp Gln Lys Cys Ser Lys Asp
        115                 120                 125

Gly Glu Thr Lys Cys Ser Leu Lys Cys Leu Lys Glu Asn Glu Ala Cys
    130                 135                 140

Lys Ala Val Asp Gly Ile Tyr Lys Cys Asp Cys Lys Asp Gly Phe Ile
145                 150                 155                 160

Ile Asp Asn Glu Ala Ser Ile Cys Thr Ala Ala Val Glu Tyr Val Asp
                165                 170                 175

Glu Lys Glu Arg Gln Gly Glu Ile Tyr Pro Phe Gly Asp Glu Glu Glu
            180                 185                 190

Lys Asp Glu Gly Gly Glu Ser Phe Thr Tyr Glu Lys Ser Glu Val Asp
        195                 200                 205

Lys Thr Asp Leu Phe Lys Phe Ile Glu Gly Gly Glu Gly Asp Asp Val
    210                 215                 220

Tyr Lys Val Asp Gly Ser Lys Val Leu Leu Asp Asp Thr Ile Ser
225                 230                 235                 240

Arg Val Ser Lys Lys His Thr Ala Arg Asp Gly Glu Tyr Gly Glu Tyr
                245                 250                 255

Gly Glu Ala Val Glu Asp Gly Glu Asn Val Ile Lys Ile Ile Arg Ser
            260                 265                 270

Val Leu Gln Ser Gly Ala Leu Pro Ser Val Gly Val Asp Glu Leu Asp
        275                 280                 285

Lys Ile Asp Leu Ser Tyr Glu Thr Thr Glu Ser Gly Thr Ala Val
    290                 295                 300

Ser Glu Asp Ser Tyr Asp Lys Tyr Ala Ser Asn Asn
305                 310                 315

<210> SEQ ID NO 27
<211> LENGTH: 328
<212> TYPE: PRT
<213> ORGANISM: Plasmodium falciparum

<400> SEQUENCE: 27
```

```
Val Thr Val Asp Thr Val Cys Lys Arg Gly Phe Leu Ile Gln Met Ser
1               5                   10                  15

Gly His Leu Glu Cys Lys Cys Glu Asn Asp Leu Val Leu Val Asn Glu
            20                  25                  30

Glu Thr Cys Glu Glu Lys Val Leu Lys Cys Asp Glu Lys Thr Val Asn
        35                  40                  45

Lys Pro Cys Gly Asp Phe Ser Lys Cys Ile Lys Ile Asp Gly Asn Pro
50                      55                  60

Val Ser Tyr Ala Cys Lys Cys Asn Leu Gly Tyr Asp Met Val Asn Asn
65                  70                  75                  80

Val Cys Ile Pro Asn Glu Cys Lys Asn Val Ala Cys Gly Asn Gly Lys
                85                  90                  95

Cys Ile Leu Asp Thr Ser Asn Pro Val Lys Thr Gly Val Cys Ser Cys
            100                 105                 110

Asn Ile Gly Lys Val Pro Asn Val Gln Asp Gln Lys Cys Ser Lys Asp
        115                 120                 125

Gly Glu Thr Lys Cys Ser Leu Lys Cys Leu Lys Glu Asn Glu Ala Cys
    130                 135                 140

Lys Ala Val Asp Gly Ile Tyr Lys Cys Asp Cys Lys Asp Gly Phe Ile
145                 150                 155                 160

Ile Asp Asn Glu Ala Ser Ile Cys Thr Ala Ala Val Glu Tyr Val Asp
                165                 170                 175

Glu Lys Glu Arg Gln Gly Ile Tyr Pro Phe Gly Asp Glu Glu Glu
            180                 185                 190

Lys Asp Glu Gly Gly Glu Ser Phe Thr Tyr Glu Lys Ser Glu Val Asp
        195                 200                 205

Lys Thr Asp Leu Phe Lys Phe Ile Glu Gly Gly Glu Gly Asp Asp Val
    210                 215                 220

Tyr Lys Val Asp Gly Ser Lys Val Leu Leu Asp Asp Thr Ile Ser
225                 230                 235                 240

Arg Val Ser Lys Lys His Thr Ala Arg Asp Gly Glu Tyr Gly Glu Tyr
                245                 250                 255

Gly Glu Ala Val Glu Asp Gly Glu Asn Val Ile Lys Ile Ile Arg Ser
            260                 265                 270

Val Leu Gln Ser Gly Ala Leu Pro Ser Val Gly Val Asp Glu Leu Asp
        275                 280                 285

Lys Ile Asp Leu Ser Tyr Glu Thr Thr Glu Ser Gly Asp Thr Ala Val
    290                 295                 300

Ser Glu Asp Ser Tyr Asp Lys Tyr Ala Ser Asn Asn Asn Gly Ile Arg
305                 310                 315                 320

Tyr His Tyr Asp Glu Tyr Ile His
                325

<210> SEQ ID NO 28
<211> LENGTH: 330
<212> TYPE: PRT
<213> ORGANISM: Plasmodium falciparum

<400> SEQUENCE: 28

Val Thr Val Asp Thr Val Cys Lys Arg Gly Phe Leu Ile Gln Met Ser
1               5                   10                  15

Gly His Leu Glu Cys Lys Cys Glu Asn Asp Leu Val Leu Val Asn Glu
            20                  25                  30

Glu Thr Cys Glu Glu Lys Val Leu Lys Cys Asp Glu Lys Thr Val Asn
```

```
                35                  40                  45
Lys Pro Cys Gly Asp Phe Ser Lys Cys Ile Lys Ile Asp Gly Asn Pro
 50                  55                  60

Val Ser Tyr Ala Cys Lys Cys Asn Leu Gly Tyr Asp Met Val Asn Asn
 65                  70                  75                  80

Val Cys Ile Pro Asn Glu Cys Lys Asn Val Ala Cys Gly Asn Gly Lys
                 85                  90                  95

Cys Ile Leu Asp Thr Ser Asn Pro Val Lys Thr Gly Val Cys Ser Cys
                100                 105                 110

Asn Ile Gly Lys Val Pro Asn Val Gln Asp Gln Lys Cys Ser Lys Asp
            115                 120                 125

Gly Glu Thr Lys Cys Ser Leu Lys Cys Leu Lys Glu Asn Glu Ala Cys
        130                 135                 140

Lys Ala Val Asp Gly Ile Tyr Lys Cys Asp Cys Lys Asp Gly Phe Ile
145                 150                 155                 160

Ile Asp Asn Glu Ala Ser Ile Cys Thr Ala Ala Val Glu Tyr Val Asp
                165                 170                 175

Glu Lys Glu Arg Gln Gly Glu Ile Tyr Pro Phe Gly Asp Glu Glu Glu
            180                 185                 190

Lys Asp Glu Gly Gly Glu Ser Phe Thr Tyr Glu Lys Ser Glu Val Asp
        195                 200                 205

Lys Thr Asp Leu Phe Lys Phe Ile Glu Gly Glu Gly Asp Val
    210                 215                 220

Tyr Lys Val Asp Gly Ser Lys Val Leu Leu Asp Asp Thr Ile Ser
225                 230                 235                 240

Arg Val Ser Lys Lys His Thr Ala Arg Asp Gly Glu Tyr Gly Glu Tyr
                245                 250                 255

Gly Glu Ala Val Glu Asp Gly Glu Asn Val Ile Lys Ile Arg Ser
            260                 265                 270

Val Leu Gln Ser Gly Ala Leu Pro Ser Val Gly Val Asp Glu Leu Asp
        275                 280                 285

Lys Ile Asp Leu Ser Tyr Glu Thr Thr Glu Ser Gly Asp Thr Ala Val
    290                 295                 300

Ser Glu Asp Ser Tyr Asp Lys Tyr Ala Ser Asn Asn Tyr Gly Lys Tyr
305                 310                 315                 320

Ile Ala Val Asp Ala Phe Ile Lys Lys Ile
                325                 330

<210> SEQ ID NO 29
<211> LENGTH: 158
<212> TYPE: PRT
<213> ORGANISM: Plasmodium falciparum

<400> SEQUENCE: 29

Phe Arg Gly Asn Asn Gly His Asp Ser Ser Ser Ser Leu Tyr Gly Gly
  1               5                  10                  15

Ser Gln Phe Ile Glu Gln Leu Asp Asn Ser Phe Thr Ser Ala Phe Leu
                 20                  25                  30

Glu Ser Gln Ser Met Asn Lys Ile Gly Asp Asp Leu Ala Glu Thr Ile
             35                  40                  45

Ser Asn Glu Leu Val Ser Val Leu Gln Lys Asn Ser Pro Thr Phe Leu
     50                  55                  60

Glu Ser Ser Phe Asp Ile Lys Ser Glu Val Lys Lys His Ala Lys Ser
 65                  70                  75                  80
```

```
Met Leu Lys Glu Leu Ile Lys Val Gly Leu Pro Ser Phe Glu Asn Leu
                85                  90                  95

Val Ala Glu Asn Val Lys Pro Pro Lys Val Asp Pro Ala Thr Tyr Gly
            100                 105                 110

Ile Ile Val Pro Val Leu Thr Ser Leu Phe Asn Lys Val Glu Thr Ala
        115                 120                 125

Val Gly Ala Lys Val Ser Asp Glu Ile Trp Asn Tyr Asn Ser Pro Asp
130             135                 140

Val Ser Glu Ser Glu Glu Ser Leu Ser Asp Asp Phe Phe Asp
145                 150                 155

<210> SEQ ID NO 30
<211> LENGTH: 74
<212> TYPE: PRT
<213> ORGANISM: Plasmodium falciparum

<400> SEQUENCE: 30

Gly Pro Ser Asp Lys His Ile Glu Gln Tyr Leu Lys Lys Ile Gln Asn
1               5                   10                  15

Ser Leu Ser Thr Glu Trp Ser Pro Cys Ser Val Thr Cys Gly Asn Gly
            20                  25                  30

Ile Gln Val Arg Ile Lys Pro Gly Ser Ala Asn Lys Pro Lys Asp Glu
        35                  40                  45

Leu Asp Tyr Glu Asn Asp Ile Glu Lys Lys Ile Cys Lys Met Glu Lys
    50                  55                  60

Cys Ser Ser Val Phe Asn Val Val Asn Ser
65                  70

<210> SEQ ID NO 31
<211> LENGTH: 51
<212> TYPE: PRT
<213> ORGANISM: Plasmodium falciparum

<400> SEQUENCE: 31

Glu Lys Thr Ala Ser Cys Gly Val Trp Asp Glu Trp Ser Pro Cys Ser
1               5                   10                  15

Val Thr Cys Gly Lys Gly Thr Arg Ser Arg Lys Arg Glu Ile Leu His
            20                  25                  30

Glu Gly Cys Thr Ser Glu Leu Gln Glu Gln Cys Glu Glu Glu Arg Cys
        35                  40                  45

Leu Pro Lys
    50

<210> SEQ ID NO 32
<211> LENGTH: 41
<212> TYPE: PRT
<213> ORGANISM: Plasmodium falciparum

<400> SEQUENCE: 32

Ile Ser Gln His Gln Cys Val Lys Lys Gln Cys Pro Glu Asn Ser Gly
1               5                   10                  15

Cys Phe Arg His Leu Asp Glu Arg Glu Glu Cys Lys Cys Leu Leu Asn
            20                  25                  30

Tyr Lys Gln Glu Gly Asp Lys Cys Val
        35                  40

<210> SEQ ID NO 33
<211> LENGTH: 48
<212> TYPE: PRT
```

<213> ORGANISM: Plasmodium falciparum

<400> SEQUENCE: 33

Gly Leu Glu Asp Glu Asp Leu Cys Lys His Asn Asn Gly Gly Cys Gly
1               5                   10                  15

Asp Asp Lys Leu Cys Glu Tyr Val Gly Asn Arg Arg Val Lys Cys Lys
                20                  25                  30

Cys Lys Glu Gly Tyr Lys Leu Glu Gly Ile Glu Cys Val Glu Leu Leu
        35                  40                  45

<210> SEQ ID NO 34
<211> LENGTH: 46
<212> TYPE: PRT
<213> ORGANISM: Plasmodium falciparum

<400> SEQUENCE: 34

Gly Asn Asn Lys Val Cys Glu Asn Thr Lys Cys Pro Leu Asn Ser Asn
1               5                   10                  15

Cys Tyr Val Ile Asp Asp Glu Thr Cys Arg Cys Leu Pro Gly Phe
                20                  25                  30

Asn Asn Ile Lys Ile Asp Asp Glu Met Asn Cys Val Arg Asp
        35                  40                  45

<210> SEQ ID NO 35
<211> LENGTH: 44
<212> TYPE: PRT
<213> ORGANISM: Plasmodium falciparum

<400> SEQUENCE: 35

Gly Asp Thr Leu Asp Cys Ser Arg Asn Asn Gly Gly Cys Asp Ile His
1               5                   10                  15

Ala Lys Cys Ser Phe Ile Asn Lys Gln Ile Val Cys Glu Cys Lys Asp
                20                  25                  30

Lys Phe Glu Gly Asp Gly Ile Tyr Cys Ser Tyr Ser
        35                  40

<210> SEQ ID NO 36
<211> LENGTH: 133
<212> TYPE: PRT
<213> ORGANISM: Plasmodium falciparum

<400> SEQUENCE: 36

Gly Lys Glu Ile Val Lys Lys Tyr Asn Leu Asn Leu Arg Asn Ala Ile
1               5                   10                  15

Leu Asn Asn Asn Ser Gln Ile Glu Asn Glu Asn Val Asn Thr Thr
                20                  25                  30

Ile Thr Gly Asn Asp Phe Ser Gly Gly Glu Phe Leu Trp Pro Gly Tyr
        35                  40                  45

Thr Glu Glu Leu Lys Ala Lys Lys Ala Ser Glu Asp Ala Glu Lys Ala
50                  55                  60

Ala Asn Asp Ala Glu Asn Ala Ser Lys Glu Ala Glu Ala Ala Lys
65              70                  75                  80

Glu Ala Val Asn Leu Lys Glu Ser Asp Lys Ser Tyr Thr Lys Ala Lys
                85                  90                  95

Glu Ala Ala Thr Ala Ala Ser Lys Ala Lys Lys Ala Val Glu Thr Ala
            100                 105                 110

Leu Lys Ala Lys Asp Asp Ala Glu Lys Ser Ser Lys Ala Asp Ser Ile
        115                 120                 125

```
Ser Thr Lys Thr Lys
    130

<210> SEQ ID NO 37
<211> LENGTH: 95
<212> TYPE: PRT
<213> ORGANISM: Plasmodium falciparum

<400> SEQUENCE: 37

Ile Ser Gln His Gln Cys Val Lys Lys Gln Cys Pro Glu Asn Ser Gly
1               5                   10                  15

Cys Phe Arg His Leu Asp Glu Arg Glu Cys Lys Cys Leu Leu Asn
            20                  25                  30

Tyr Lys Gln Glu Gly Asp Lys Cys Val Glu Asn Pro Asn Pro Thr Cys
        35                  40                  45

Asn Glu Asn Asn Gly Gly Cys Asp Ala Asp Ala Lys Cys Thr Glu Glu
    50                  55                  60

Asp Ser Gly Ser Asn Gly Lys Lys Ile Thr Cys Glu Cys Thr Lys Pro
65                  70                  75                  80

Asp Ser Tyr Pro Leu Phe Asp Gly Ile Phe Cys Ser Ser Asn
            85                  90                  95

<210> SEQ ID NO 38
<211> LENGTH: 113
<212> TYPE: PRT
<213> ORGANISM: Plasmodium falciparum

<400> SEQUENCE: 38

Lys Lys Tyr Glu Thr Tyr Val Asp Met Lys Thr Ile Glu Ser Lys Tyr
1               5                   10                  15

Thr Thr Val Met Thr Leu Ser Glu His Leu Leu Glu Tyr Ala Met Asp
            20                  25                  30

Val Leu Lys Ala Asn Pro Gln Lys Pro Ile Asp Pro Lys Ala Asn Leu
        35                  40                  45

Asp Ser Glu Val Val Lys Leu Gln Ile Lys Ile Asn Glu Lys Ser Asn
    50                  55                  60

Glu Leu Asp Asn Ala Ala Ser Gln Val Lys Thr Leu Ile Ile Ile Met
65                  70                  75                  80

Lys Ser Phe Tyr Asp Ile Ile Ile Ser Glu Lys Ala Ser Met Asp Glu
            85                  90                  95

Met Glu Lys Lys Glu Leu Ser Leu Asn Asn Tyr Ile Glu Lys Thr Asp
                100                 105                 110

Tyr

<210> SEQ ID NO 39
<211> LENGTH: 80
<212> TYPE: PRT
<213> ORGANISM: Plasmodium falciparum

<400> SEQUENCE: 39

Gly Tyr Cys Lys Asp Ile Asn Cys Lys Glu Asn Glu Glu Cys Ser Ile
1               5                   10                  15

Val Asn Phe Lys Pro Glu Cys Val Cys Lys Glu Asn Leu Lys Lys Asn
            20                  25                  30

Asn Lys Gly Glu Cys Ile Ala Ala Ser Cys Leu Ile Asn Glu Gly Asn
        35                  40                  45

Cys Pro Lys Asp Ser Lys Cys Ile Tyr Arg Glu Tyr Lys Pro His Glu
    50                  55                  60
```

-continued

Cys Val Cys Asn Lys Gln Gly His Val Ala Val Asn Gly Lys Cys Val
65                  70                  75                  80

<210> SEQ ID NO 40
<211> LENGTH: 38
<212> TYPE: PRT
<213> ORGANISM: Plasmodium falciparum

<400> SEQUENCE: 40

Gly Tyr Cys Lys Asp Ile Asn Cys Lys Glu Asn Glu Glu Cys Ser Ile
1               5                   10                  15

Val Asn Phe Lys Pro Glu Cys Val Cys Lys Glu Asn Leu Lys Lys Asn
            20                  25                  30

Asn Lys Gly Glu Cys Ile
        35

<210> SEQ ID NO 41
<211> LENGTH: 40
<212> TYPE: PRT
<213> ORGANISM: Plasmodium falciparum

<400> SEQUENCE: 41

Ser Cys Leu Ile Asn Glu Gly Asn Cys Pro Lys Asp Ser Lys Cys Ile
1               5                   10                  15

Tyr Arg Glu Tyr Lys Pro His Glu Cys Val Cys Asn Lys Gln Gly His
            20                  25                  30

Val Ala Val Asn Gly Lys Cys Val
        35                  40

<210> SEQ ID NO 42
<211> LENGTH: 13
<212> TYPE: PRT
<213> ORGANISM: Plasmodium falciparum

<400> SEQUENCE: 42

Thr Asn Gly Ile Arg Tyr His Tyr Asp Glu Tyr Ile His
1               5                   10

<210> SEQ ID NO 43
<211> LENGTH: 14
<212> TYPE: PRT
<213> ORGANISM: Plasmodium falciparum

<400> SEQUENCE: 43

Tyr Gly Lys Tyr Ile Ala Val Asp Ala Phe Ile Lys Lys Ile
1               5                   10

<210> SEQ ID NO 44
<211> LENGTH: 169
<212> TYPE: PRT
<213> ORGANISM: Plasmodium falciparum

<400> SEQUENCE: 44

Val Thr Val Asp Thr Val Cys Lys Arg Gly Phe Leu Ile Gln Met Ser
1               5                   10                  15

Gly His Leu Glu Cys Lys Cys Glu Asn Asp Leu Val Leu Val Asn Glu
            20                  25                  30

Glu Thr Cys Glu Glu Lys Val Leu Lys Cys Asp Glu Lys Thr Val Asn
        35                  40                  45

Lys Pro Cys Gly Asp Phe Ser Lys Cys Ile Lys Ile Asp Gly Asn Pro
    50                  55                  60

```
Val Ser Tyr Ala Cys Lys Cys Asn Leu Gly Tyr Asp Met Val Asn Asn
 65                  70                  75                  80

Val Cys Ile Pro Asn Glu Cys Lys Asn Val Ala Cys Gly Asn Gly Lys
                 85                  90                  95

Cys Ile Leu Asp Thr Ser Asn Pro Val Lys Thr Gly Val Cys Ser Cys
                100                 105                 110

Asn Ile Gly Lys Val Pro Asn Val Gln Asp Gln Lys Cys Ser Lys Asp
                115                 120                 125

Gly Glu Thr Lys Cys Ser Leu Lys Cys Leu Lys Glu Asn Glu Ala Cys
            130                 135                 140

Lys Ala Val Asp Gly Ile Tyr Lys Cys Asp Cys Lys Asp Gly Phe Ile
145                 150                 155                 160

Ile Asp Asn Glu Ala Ser Ile Cys Thr
                165

<210> SEQ ID NO 45
<211> LENGTH: 144
<212> TYPE: PRT
<213> ORGANISM: Plasmodium falciparum

<400> SEQUENCE: 45

Glu Tyr Val Asp Glu Lys Glu Arg Gln Gly Glu Ile Tyr Pro Phe Gly
  1               5                  10                  15

Asp Glu Glu Glu Lys Asp Glu Gly Gly Glu Ser Phe Thr Tyr Glu Lys
                 20                  25                  30

Ser Glu Val Asp Lys Thr Asp Leu Phe Lys Phe Ile Glu Gly Gly Glu
                 35                  40                  45

Gly Asp Asp Val Tyr Lys Val Asp Gly Ser Lys Val Leu Leu Asp Asp
             50                  55                  60

Asp Thr Ile Ser Arg Val Ser Lys Lys His Thr Ala Arg Asp Gly Glu
 65                  70                  75                  80

Tyr Gly Glu Tyr Gly Glu Ala Val Glu Asp Gly Glu Asn Val Ile Lys
                 85                  90                  95

Ile Ile Arg Ser Val Leu Gln Ser Gly Ala Leu Pro Ser Val Gly Val
                100                 105                 110

Asp Glu Leu Asp Lys Ile Asp Leu Ser Tyr Glu Thr Thr Glu Ser Gly
            115                 120                 125

Asp Thr Ala Val Ser Glu Asp Ser Tyr Asp Lys Tyr Ala Ser Asn Asn
130                 135                 140
```

MULTI-COMPONENT-MULTISTAGE MALARIA VACCINES

CROSS REFERENCE TO RELATED APPLICATIONS

This is a US national phase application of PCT/EP2015/056693, filed Mar. 27, 2015, which claims benefit of priority to European patent application no. EP 14001155.2, filed Mar. 28, 2014 and US provisional patent application no. U.S. 61/972,002, filed Mar. 28, 2014; each of which is herein incorporated by reference in its entirety.

FIELD OF THE INVENTION

The present disclosure relates to novel malaria vaccines composed of different recombinant proteins, in particular recombinant fusion proteins comprising several different *Plasmodium falciparum* antigens from the pre-erythrocytic, the blood, and the sexual parasite stages. The proteins and/or fusion proteins will be used in a mixture vaccine formulation to elicit protective immune responses in humans. Nucleic acid molecules encoding said recombinant proteins, vectors, host cells containing the nucleic acids and methods for preparation and producing such proteins; Antibodies induced or generated by the use of said malaria vaccines or said nucleic acid molecules encoding said proteins and/or fusion proteins and the use of such antibodies or recombinant derivatives for passive immunotherapy.

BACKGROUND

Malaria is a disease caused by infection with parasites of the phylum *Apicomplexa* protozoan, namely parasites of the genus *Plasmodium*, globally causing more than 200 million new infections and 700 thousand deaths every year. Malaria is especially a serious problem in Africa, where one in every five (20%) childhood deaths is due to the effects of the disease. An African child has on average between 1.6 and 5.4 episodes of malaria fever each year.

Malarial diseases in humans are caused by five species of the *Plasmodium* parasite: *P. falciparum, P. vivax, P. ovale, P. malariae* and *P. knowlesi*, wherein the most prevalent being *Plasmodium falciparum* and *Plasmodium vivax*. Malaria caused by *Plasmodium falciparum* (also called malignant or malaria, *falciparum* malaria or malaria *tropica*) is the most dangerous form of malaria, with the highest rates of complications and mortality. Almost all malarial deaths are caused by *P. falciparum*.

Briefly, the plasmodial life cycle (FIG. 1) in man starts with the inoculation of a few sporozoites through the bite of an *Anopheles* mosquito. Within minutes, sporozoites invade the hepatocyte and start their development, multiplying by schizogony (liver stage or pre-erythrocytic stage). After a period of 5-14 days—depending on the plasmodial species—schizonts develop into thousands of merozoites that are freed into the bloodstream and invade the red blood cells (RBCs), initiating the blood stage. In the RBC, each merozoite develops into a trophozoite that matures and divides, generating a schizont that, after fully matured, gives rise to up to 32 merozoites within 42-72 h, depending on the plasmodial species. The merozoites, released into the bloodstream, will invade other RBC, maintaining the cycle. Some merozoites, after invading a RBC, develop into sexual forms—the male or female gametocytes which also enter the bloodstream after maturation and erythrocyte rupture. If a female *Anopheles* mosquito takes its blood meal and ingests the gametocytes, it will become infected and initiates the sexual stage of the *Plasmodium* life cycle. In the mosquito gut, the male gametocyte fuses with the female gametocyte, forming the ookinete, which binds to and passes through the gut wall, remains attached to its external face and transforms into the oocyst. The oocyst will divide by sporogony, giving rise to thousands of sporozoites that are released in the body cavity of the mosquito and eventually migrate to its salivary gland, where they will maturate, becoming capable of starting a new infection in humans when the mosquito bites the host for a blood meal.

Resistance of *Plasmodium falciparum* to the existing anti-malarial drug chloroquine emerged in the sixties and has been spreading since then. In addition, the malaria parasite has developed resistance to most other anti-malarial drugs over the past decades. This poses a major threat to public health in tropical countries and to travelers. There is every reason to believe that the prevalence and degree of anti-malarial drug resistance will continue to increase. The growing number of insecticide resistant vectors and drug resistant parasites further increases the demand for an effective malaria vaccine. Malaria vaccines are not limited to a single mode of action and hold the potential to dramatically alleviate the burden of malaria.

Some of the difficulties to develop an efficient malaria vaccine result from the multi-stage life cycle of the parasite. Each stage of the parasite development is characterized by different sets of surface antigens, eliciting different types of immune responses. Despite the large variety of displayed surface antigens, the immune response against them is often ineffective. One of the reasons is the extensive sequence polymorphism of plasmodial antigens, which facilitates the immune evasion of the different isolates.

A pre-erythrocytic vaccine would protect against the infectious form (sporozoite) injected by a mosquito and thereby inhibit parasite development in the liver. In a previously unexposed individual, if a few parasites were to escape the immune defences induced by a pre-erythrocytic vaccine, they would eventually enter the blood-stage, multiply within the erythrocytes and establish a full-blown disease.

An erythrocytic or blood-stage vaccine would inhibit the invasion and multiplication of the parasite in the red blood cells, thus preventing (or diminishing) severe disease symptoms during the blood infection. However, it is unlikely to completely interrupt the *Plasmodium* life cycle and prevent transmission of the parasite by this approach.

A sexual-stage vaccine would not protect the person being vaccinated, but instead interrupt the cycle of transmission by inhibiting the development of parasites once they are ingested by the mosquito along with antibodies produced in response to the vaccine, Transmission-blocking vaccines could be involved as part of a multi-faceted strategy directed towards parasite elimination and at the same time towards prevention of parasite resistance to anti pre-erythrocytic or erythrocytic treatment.

The above-mentioned complex multistage life cycle of malaria parasites presents unique challenges for a synergistic vaccine approach. Immunity against malaria parasites is stage dependent and species dependent. Many malaria researchers and textbook descriptions believe and conclude that a single-antigen vaccine representing only one stage of the life cycle will not be sufficient and that a multiantigen, multistage vaccine that targets different, that is at least two, stages of parasite development is necessary to induce effective immunity (Mahajan, Berzofsky et al. 2010). The construction of a multiantigen vaccine (with the aim of covering different parasite stages and increasing the breadth of the vaccine-induced immune responses to try to circumvent potential *Plasmodium. falciparum* escape mutants) can be achieved by either genetically linking (full-size) antigens together, by a mixture of recombinant proteins or by synthetic-peptide-based (15-25-mer), chemically synthesized vaccines containing several peptides derived from different parasite proteins and stages.

A single fusion protein approach being comprised of several different antigens or several different alleles of a single antigen (to induce antibodies with synergistic activities against the parasite) is hindered by antigenic diversity and the capacity of *P. falciparum* for immune evasion (Richards, Beeson, 2009). A large number of antigens have been evaluated as potential vaccine candidates, but most clinical trials have not shown significant impact on preventing clinical malaria although some of them have shown to reduce parasite growth. The size of the resulting fusion protein/vaccine candidate is another limiting factor allowing only the combination of a few selected antigens, not excluding that the chosen antigens are not targets of natural immunity and/or exhibit significant genetic polymorphism. Highly variable antigens with multiple alleles are obviously targets of the immune response under natural challenge, and vaccine studies of PfAMA1 and PfMSP2 suggest that allele-specific effects can be achieved (Schwartz, 2012). Currently only combination vaccines (being comprised of PfCSP und PfAMA1) are undergoing clinical trials which target the pre-erythrocytic and asexual blood stage of *P. falciparum* (Schwartz, 2012). A multiantigen vaccine candidate, neither a fusion, nor a combination approach, targeting all three life cycle stages of *Plasmodium* (including the sexual stage in *Anopheles* mosquitos and thus blocking parasite transmission) is still not tested in clinical trials.

Therefore the availability of novel and improved multi-component, multi-stage vaccines against *Plasmodium falciparum* would be highly advantageous.

BRIEF SUMMARY OF THE INVENTION

The present disclosure relates to combinations of recombinant proteins and/or recombinant fusion proteins suitable as human vaccines against malaria comprising a plurality of proteins or protein domains derived from proteins preferably, but not necessarily presented on the surface of the *Plasmodium falciparum* parasite during different stages in the life cycle of the parasite.

In a first aspect, the present disclosure pertains to mixtures of recombinant proteins suitable as a human vaccine against the parasite *Plasmodium falciparum* comprising antigens from *Plasmodium falciparum* surface proteins of the pre-erythrocytic, the blood-, and the sexual-stage of the parasite life cycle, wherein
   a) the pre-erythrocytic antigens comprise at least the antigens PfCelTOS, PfCSP and PfTRAP, or domains, variants or fragments thereof, and
   b) the blood stage antigen(s) comprise at least one or more variants of Apical membrane antigen 1 (PfAMA1), or fragments thereof; and
   c) the sexual stage antigen(s) comprise the ookinete antigen Pfs25 and/or the gamete/gametocyte surface protein Pf230C0, or variants or fragments thereof.

In a further aspect, embodiments of this disclosure relate to antibody composition comprising different isolated antibodies or fragments thereof binding to the different recombinant proteins in the mixture according to the present disclosure.

In another aspect, embodiments of this disclosure relate to pharmaceutical and/or diagnostic compositions comprising a mixture of recombinant proteins or antibodies according to the present disclosure.

In a further aspect, embodiments of this disclosure relate to vaccine compositions for immunizing a susceptible mammal against malaria comprising as an active ingredient a mixture of recombinant proteins according to the present disclosure and a carrier in a physiologically acceptable medium.

In still another aspect, embodiments of this disclosure provide nucleic acids encoding said recombinant fusion proteins comprised in a mixture according to the present disclosure, as well as vectors and host cells comprising such nucleic acids.

In other aspects, this disclosure relates to use of a mixture of recombinant proteins according to the present disclosure in the prevention and/or treatment of malaria *tropica*.

Furthermore, methods of immunizing humans against an infection, in particular against *Plasmodium falciparum*, comprising administering an effective amount of recombinant proteins comprised in a mixture of the present disclosure, a composition comprising a mixture of recombinant fusion proteins of the present disclosure or a vaccine composition according to the present disclosure are disclosed.

Further, the present disclosure pertains to diagnostic assays comprising an antibody composition according to the present disclosure and diagnostic kits comprising the antibody composition according to the present disclosure or the diagnostic assay according to the present disclosure.

Before the disclosure is described in detail, it is to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 6 shows a SDS-PAGE and a Western Blot analysis of the different recombinant proteins used to prepare vaccine mixture M1 and M2 according to the present disclosure.

DETAILED DESCRIPTION OF THE INVENTION

Figure 1:
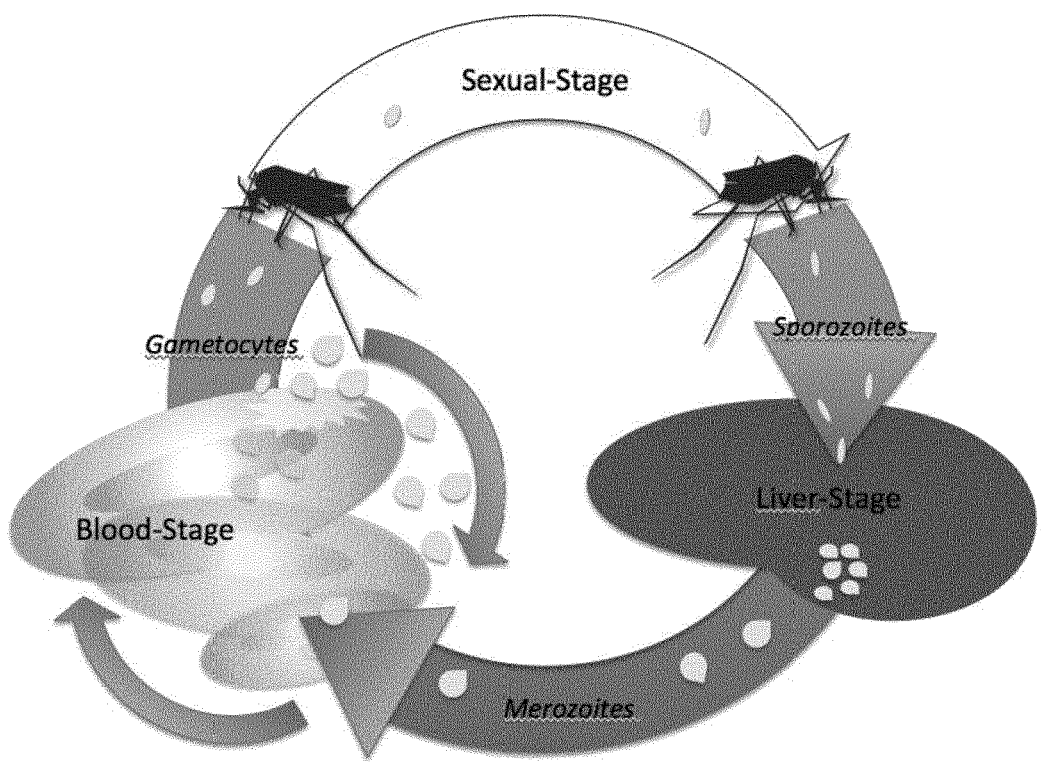
FIG. 1 is a scheme of the life cycle of *Plasmodium falciparum*.

The present disclosure pertains to combinations of recombinant proteins, in particular fusion proteins suitable as human vaccines against *Plasmodium falciparum*. In advantageous embodiments, the recombinant proteins and vaccine compositions according to the present disclosure combine *Plasmodium falciparum* surface proteins and domains from different stages of the parasite development.

The complex multi-stage life cycle and the genetic variability of *Plasmodium falciparum* represent a significant challenge for successful malaria vaccine development. Depending on the developmental stage the parasite displays different sets of surface proteins that need to be targeted by a protective immuneresponse with the goal to reduce or prevent invasion of liver cells (pre-erythrocytic stage), reduce or prevent clinical manifestation of malaria (blood stage) and to reduce or prevent transmission of malaria through the mosquito host. Additionally many important surface proteins are di-, or even polymorphic. Therefore, an efficient, multi stage malaria vaccine has to combine a plurality of relevant antigens from different stages. One approach to address this is the design of fusion proteins that comprise a number of suitable proteins and/or protein domains. Additionally, the desire for such a vaccine candidate composed of a single polypeptide is mainly driven by practical, technical and economical demands for reproducible, robust and cost-efficient production.

However, to those skilled in the Art, it is also clear, that there is a size limitation for recombinant expressed fusion proteins. Although protein specific differences have to be taken into account as well, there is a strong decrease of expression levels and yields with increasing length of the polypeptide. Multiple challenges increase over-proportionally with size and the overall properties of large proteins are significantly less amenable to optimization than those of smaller proteins, domains or fragments. All these problems have so far been significant bottlenecks for the development of efficient vaccines against *Plasmodium falciparum* and have resulted in an overwhelming number of sub-optimal vaccine candidates that comprise only multiple linear epitopes, one or two antigens from a one or two life cycle stages. As alternative, chemically or genetically attenuated or inactivated life-vaccines are proposed (e.g. irradiated sporozoites), but such approaches have to deal with batch-to-batch consistency, scaled-up production and most importantly product safety.

The use of mixtures of recombinant proteins to cover both, the parasite life cycles relevant for spread and clinical manifestation of malaria, as well as the allelic variations of immunologically relevant *Plasmodium falciparum* surface proteins has several advantages. Allelic variants or even artificial, diversity covering versions can be combined with conserved antigens from different stages by genetic fusion as well as by mixing them in a formulation. The approach is not hampered by the need to combine relevant antigens from all stages into one large fusion protein since polypetide size as well as yield and stability in the respective production systems can be considered in the design of suitable fusion proteins in such multicomponent vaccines. Another advantage of such antigen mixtures is higher flexibility to match the geographical distribution as well as the evolution of the pathogen by adapting components of the mixture according to the given needs, and the broad multistage-specific immune response that can be elicited with such antigen cocktails that feature a number of immunorelevant antigens (and their B- and T-cell epitopes that cannot be easily realized within the context of a single fusion protein.

The recombinant proteins and fusion proteins comprised in the mixtures described in the present disclosure are designed and optimized for optimal yield and stability in the chosen production host *N. benthamiana*. The fusion proteins have been designed to address distinct stages of the *Plasmodium falciparum* lifecycle and feature the most essential antigens or antigendomains required to elicit the desired immune responses. Combining antigens into fusion proteins is useful to reduce the number of proteins used in a vaccine mixture and reduce upstream, downstream and quality control costs during production, combining stage specific antigens into fusion proteins is a favourable concept to finetune the efficacy and the specificity of a multi-stage, multi-component vaccine composition by implementing different ratios of the stage-specific functionalities in the composition.

Furthermore, due to the specific combination of the antigens, the vaccine mixtures according to the present disclosure can be well expressed and the expression level is high and therefore not only suitable for lab-scale but also for large-scale/industrial-scale production. Furthermore, the selection of the antigens comprised in the vaccine mixtures according to the present disclosure the titers against all antigen domains are high. Due to the induced titers, the parasite inhibition in all available assays for every *Plasmodium* main-stage is improved. Furthermore, the free miscibility allows a balanced immune response and a balanced inhibitory activity of the vaccine mixtures according to the present disclosure.

Importantly, the fusion proteins comprised in the mixtures according to the present disclosure (i) comprise domains derived from different *Plasmodium falciparum* surface proteins and (ii) were designed using building blocks (domains) that have been experimentally identified and verified as well expressing and immunologically relevant.

In some cases, for example PfCelTos the genetic fusion to two other pre-erythrocytic antigens surprisingly leads to significantly higher expression levels compared to its separate expression in plants, enabling the relevant antigen PfCelTos to be efficiently expressed and used as an antigen in a multi-stage, multi-component vaccine.

Another extremely important aspect of the present disclosure is the unexpected finding that strong immuneresponses against the different components from the three parasite stages could be elicited by injection of an antigen mixture comprising antigens from *Plasmodium falciparum* surface proteins of the pre-erythrocytic, the blood-, and the sexual-stage of the parasite life cycle, wherein
  a) the pre-erythrocytic antigens comprise at least the antigens PfCelTOS, PfCSP and PfTRAP, or domains, variants or fragments thereof, and
  b) the blood stage antigen(s) comprise at least one or more variants of Apical membrane antigen 1 (PfAMA1), or fragments thereof; and
  c) the sexual stage antigen(s) comprise the ookinete antigen Pfs25 and/or the gamete/gametocyte surface protein Pf230C0, or variants or fragments thereof.

In an advantageous embodiment, the domain of PfCSP is the TSR-domain of PfCSP. In another advantageous embodiment the domain of PfTRAP is the TSR-domain of PfTRAP.

In an advantageous embodiment, the mixture according to the present disclosure the blood stage antigens comprise at least a further *Plasmodium falciparum* blood stage antigen.

In summary, the described combinations of the recombinant proteins and fusion proteins of the present disclosure can be well expressed have a high immunological relevance and have an improved immunogenicity. In advantageous embodiments, the combinations of recombinant proteins and fusion proteins of the present disclosure used as vaccines have the ability to elicit protective immunity that blocks infection as well as prevents pathology and interrupts transmission of parasites, and would most likely be a combination vaccine composed of subunits from different parasite stages.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E, ed. (1994); "Culture of Animal Cells—A Manual of Basic Technique" by Freshney, Wiley-Liss, N.Y. (1994), Third Edition; "Current Protocols in Immunology" Volumes I-III Coligan J. E, ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

The phrase "recombinant protein" includes proteins, in particular recombinant fusion proteins that are prepared, expressed, created or isolated by recombinant means, such as proteins expressed using a recombinant expression vector transfected into a host cell.

The term "recombinant fusion protein" refers to a protein produced by recombinant technology which comprises segments i.e. amino acid sequences, from heterologous sources, such as different proteins or different organisms. The segments are joined either directly or indirectly to each other via peptide bonds. By indirect joining it is meant that an intervening amino acid sequence, such as a peptide linker is juxtaposed between segments forming the fusion protein. A recombinant fusion protein is encoded by a nucleotide sequence, which is obtained by genetically joining nucleotide sequences derived from different regions of one gene and/or by joining nucleotide sequences derived from two or more separate genes. These nucleotide sequences can be derived from *P. falciparum*, but they may also be derived from other organisms, the plasmids used for the cloning procedures or from other nucleotide sequences.

Furthermore, the encoding nucleotide sequences may be synthesized in vitro without the need for initial template DNA samples e.g. by oligonucleotide synthesis from digital genetic sequences and subsequent annealing of the resultant fragments. Desired protein sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops, . . . ), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

A recombinant fusion protein comprising *Plasmodium* surface proteins or domains thereof can be a recombinant product prepared using recombinant DNA methodology and expression in a suitable host cell, as is known in the art (see for example Sambrook et al., (2001) Molecular Cloning, Cold Spring Harbor Laboratory Press, Cold Spring Harbor, N. Y). Nucleotide sequences encoding specific isolated protein domain may be conveniently prepared, for example by polymerase chain reaction using appropriate oligonucleotide primers corresponding to the 5' and 3' regions of the domain required for isolation, and a full length coding of the isolated protein domain sequence as template. The source of the full length coding protein sequence may be for example, DNA extracted from parasite cells or a plasmid vector containing a cloned full length gene. Alternatively, the protein coding sequence may partially or completely be synthesized in vitro or a combination of different approaches may be used. Non-limiting examples of properties of the fusion proteins according to the present are thermostability and pH-stability.

In an advantageous embodiment, the vaccine compositions or mixture of recombinant proteins according to the present disclosure comprise antigens from *Plasmodium falciparum* surface proteins of the pre-erythrocytic, the blood-, and the sexual-stage of the parasite life cycle, wherein a) the pre-erytrocytic antigens comprise at least PfCelTOS, the TSR-domain of PfCSP and the TSR-domain of PfTRAP, b) the blood stage antigens comprise one or more variants of Apical membrane antigen (PfAMA1) and c) the sexual stage antigen(s) comprise the ookinete antigen Pfs25 and/or the gamete/gametocyte surface protein Pf230C0, or variants thereof.

As mentioned above, in advantageous embodiments, the mixture according to the present disclosure the blood stage antigens comprise at least a further *Plasmodium falciparum* blood stage antigen.

As used herein, the pre-erytrocytic antigen "PfCelTos" refers to the *Plasmodium falciparum* Cell traversal protein for ookinetes and sporozoites (CelTos), the pre-erytrocytic antigen "PfCSP_TSR" refers to the TSR-domain from Circum Sporozoite Protein (CSP) of *P. falciparum* and "PfTRAP_TSR" refers to the TSR-domain from Thrombospondin-related adhesive proten (TRAP) of *P. falciparum*.

A "TSR domain" is a small about 60-residue domain found in extracellular proteins or in the extracellular part of transmembrane proteins that are involved in immunity, cell adhesion, cell-cell-interactions and neuronal development (Tucker, 2004). Structures of TSR domains from thrombospondin-1 (TSP-1; Tan et al. 2002) and F-spondin (PDB codes 1SZL and 1VEX) have been solved. These show that a TSR domain has an elongated structure consisting of an antiparallel three-stranded β-sheet. The domain core is formed by a stacked array of side chains of conserved tryptophans, arginines, and cysteines. TSRs of several proteins have been reported to mediate glycosaminoglycan (GAG) binding. For example, the *plasmodium* surface proteins *plasmodium* CS and TRAP both contain an adhesive thrombospondin type 1 domain, TSR.

In one embodiment, the PfCelTOS antigen comprises a polypeptide having SEQ ID NO. 29. In a further embodiment the TSR-domain of PfCSP comprises a polypeptide having SEQ ID NO. 30. In another embodiment the TSR-domain of PfTRAP comprises a polypeptide having SEQ ID NO. 31. In another embodiment the pre-erytrocytic antigens comprises polypeptides having SEQ ID NO. 29, SEQ ID NO. 30 and/or SEQ ID NO. 31.

In an advantageous embodiment the pre-erytrocytic antigens are comprised in a recombinant fusion protein. In one embodiment recombinant fusion protein comprises SEQ ID NO. 1, SEQ ID NO. 5, SEQ ID NO. 6, SEQ ID NO. 7, SEQ ID NO. 8, SEQ ID NO. 9, or SEQ ID NO. 10, or homologous polypeptides thereof, which are produced by recombinant or synthetic methods by substitution, insertion, addition or deletion of one or more amino acid residues.

In another advantageous embodiment, the blood stage antigens comprise one or more variants of Apical membrane antigen (PfAMA1) and at least a further *Plasmodium falciparum* blood stage antigen.

As used herein, the antigen "PfgAMA1" refers to the *Plasmodium falciparum* Apical membrane antigen (AMA1) extracellular domains 1-3. Recombinant proteins representing the whole ectodomain (Domains I-III) of *Plasmodium falciparum*. AMA-1 can induce antibodies that recognise native parasites and inhibit merozoite invasion of erythrocytes in vitro. The limited polymorphism of PfAMA1 enabled the rational design of three artificial PfAMA1 sequences with a very high coverage of naturally occurring alleles (on average >97%). This Diversity Covering approach (DiCo) is expected to overcome the polymorphism found in nature and to allow a broad response to all naturally occurring AMA1 alleles.

Therefore, the variant of the Apical membrane antigen (PfAMA1) may be any wild-type PfAMA1, PfAMA1-DICO1, PfAMA1-DICO2 and/or PfAMA1-DICO3, and also variants thereof with removed or additional potential N-Glycosylation sites, with or without its native propeptide sequence.

In an advantageous embodiment, the variant of the Apical membrane antigen (PfAMA1) in the vaccine mixture is a wild-type PfAMA1. In one embodiment, the PfAMA1 variant comprise a polypeptide having the amino acid sequence of SEQ ID NO. 2, SEQ ID NO. 11, SEQ ID NO. 12, SEQ ID NO. 13, SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, or SEQ ID NO. 22, or homologous polypeptides thereof, which are produced by recombinant or synthetic methods by substitution, insertion, addition or deletion of one or more amino acid residues. In another embodiments, the PfAMA1 variant carries expression host specific N-Glycans, for example if expressed in a plant.

In another advantageous embodiment, the mixture or vaccine composition according to the present disclosure comprises one or more further *Plasmodium falciparum* blood stage antigen in addition to the PfAMA1 variant. In one advantageous embodiment, this further *Plasmodium falciparum* blood stage antigen is selected from the group consisting of PfMsp1-19_EGF1 (SEQ ID NO. 37), PfRIPR_EGF7/8 (SEQ ID NO. 39), PfRh2 (SEQ ID NO. 38), PfRh5 ((SEQ ID NO. 42 and 43), PfMsp4_EGF (SEQ ID NO. 33), PfMsp8_EGF1 (SEQ ID NO. 34), PfMsp8_EGF2 (SEQ ID NO. 35), and N-terminal fragment of PfMsp3 (SEQ ID NO. 36), or fragments or peptides thereof.

The several merozoite surface proteins (MSPs) have been identified, but for most of them their function still has to be further elucidated. In the case of the major MSP, named MSP-1, a role has been postulated in merozoite binding to the RBC and in the subsequent biochemical mechanisms involved in invasion. This protein is synthesized as a precursor of 185-210 kDa in the late schizont stage and is processed to generate several polypeptides of varied molecular weights. A 42 kDa polypeptide (MSP1-42) is kept attached to the merozoite membrane, and it is further processed to generate a 19 kDa polypeptide (MSP1-19), which goes into the host cell. Besides MSP-1, at least eight other MSPs have been described in *P. falciparum*: MSP-2, MSP-3, MSP-4, MSP-5, MSP-6, MSP-7, MSP-8 and MSP-10. Another merozoite surface-associated antigen is the acidic-basic repeat antigen (ABRA). Proteins located in merozoite apical organelles have also been identified like the rhoptry-associated protein-1 (RAP-1) and RAP-2).

As used herein, "EGF" refers to "EGF-like domain" which is an EGF-like motif that may be found in a variety of proteins, as well as EGF and Notch and Notch ligands, including those involved in the blood clotting cascade (Furie and Furie, 1988, Cell 53: 505-518). For example, this motif has been found in extracellular proteins such as the blood clotting factors IX and X (Rees et al, 1988, EMBO J. 7:2053-2061; Furie and Furie, 1988, Cell 53: 505-518), in other *Drosophila* genes (Knust et al., 1987 EMBO J. 761-766; Rothberg et al, 1988, Cell 55:1047-1059), and in some cell-surface receptor proteins, such as thrombomodulin (Suzuki et al., 1987, EMBO J. 6:1891-1897) and LDL receptor (Sudhof et al, 1985, Science 228:815-822). A protein binding site has been mapped to the EGF repeat domain in thrombomodulin and urokinase (Kurosawa et al., 1988, J. Biol. Chem 263:5993-5996; Appella et al., 1987, J. Biol. Chem. 262:4437-4440).

The term "fragment" as used herein refers to a continuous part of a natural full-length protein, with or without mutations, which is separate from and not in the context of a full length *Plasmodium falciparum* surface protein. It may be a structural/topographical or functional subunit of a full length or complete protein.

In some embodiments, the further *Plasmodium falciparum* blood stage antigen is selected from the group consisting of PfMsp1-19_EGF1 (SEQ ID NO. 37), PfRIPR_EGF7/8 (SEQ ID NO. 39), and PfRh2 (SEQ ID NO. 38). In an advantageous embodiment, the mixture or vaccine composition according to the present disclosure comprises as further *Plasmodium falciparum* blood stage antigens PfMsp1-19_EGF1 (SEQ ID NO. 37), PfMsp4_EGF (SEQ ID NO. 33), PfMsp8_EGF1 (SEQ ID NO. 34), PfMsp8_EGF2 (SEQ ID NO. 35), and an N-terminal fragment of PfMsp3 (SEQ ID NO. 36).

In another embodiments, the further *Plasmodium falciparum* blood stage antigen is a peptide selected from the group consisting of PfRh5 (GenBank: ACB87908.1: AA353-365, SEQ ID NO. 42 and GenBank: ACB87908.1: AA199-213, SEQ ID NO. 43).

In an advantageous embodiment, the further *Plasmodium falciparum* blood stage antigens are comprised in a recombinant fusion protein, for example in a recombinant fusion protein comprising SEQ ID NO. 3, or a homologous polypeptide thereof, which are produced by recombinant or synthetic methods by substitution, insertion, addition or deletion of one or more amino acid residues.

In further advantageous embodiments, the blood stage antigens of the mixture or vaccine compositions according to the present disclosure comprise PfAMA1-DICO1 and PfMsp1-19, preferably as recombinant fusion protein.

In further advantageous embodiments, the blood stage antigens of the mixture or vaccine compositions according to the present disclosure comprise PfAMA1-DICO2 and PfRh2, preferably as recombinant fusion protein.

In further advantageous embodiments, the blood stage antigens of the mixture or vaccine compositions according to the present disclosure comprise PfAMA1-DICO3, PfRIPR_EGF7/8, preferably as recombinant fusion protein.

In another advantageous embodiment, the blood stage antigens of the mixture or vaccine compositions according to the present disclosure comprise.
  i) PfAMA1-DICO1 and PfMsp1-19
  ii) PfAMA1-DICO2 and PfRh2, and
  iii) PfAMA1-DICO3, PfRIPR_EGF7/8

In one embodiment, the PfAMA1-DICO1 and PfMsp1-19 antigens are comprised in a first recombinant fusion protein, the PfAMA1-DICO2 and PfRh2 antigens are comprised in a second recombinant fusion protein, and the PfAMA1-DICO3, PfRIPR_EGF7/8 antigens are comprised in a third recombinant fusion protein.

In another embodiment, the above mentioned first recombinant fusion protein comprises SEQ ID NO. 14 or 20, or a homologous polypeptide thereof, which are produced by recombinant or synthetic methods by substitution, insertion, addition or deletion of one or more amino acid residues.

In another embodiment, the above mentioned second recombinant fusion protein comprises SEQ ID NO. 15 or 21, or a homologous polypeptide thereof, which are produced by recombinant or synthetic methods by substitution, insertion, addition or deletion of one or more amino acid residues.

In another embodiment, the above mentioned the third recombinant fusion protein comprises SEQ ID NO. 16 or 22, or a homologous polypeptide thereof, which are produced by recombinant or synthetic methods by substitution, insertion, addition or deletion of one or more amino acid residues.

The mixture of recombinant proteins and the vaccine compositions according to the present disclosure comprises at least a sexual stage antigen, in particular the ookinete antigen Pfs25 (SEQ ID NO. 44) and/or the gamete/gametocyte surface protein Pfs230C0 (SEQ ID NO. 45), or variants thereof.

In one embodiment, the variants of the sexual stage antigens Pfs25 and Pfs230C0 are wild type or variants with removed or additional potential N-Glycan recognition sites.

In an advantageous embodiment, the mixture of recombinant proteins and the vaccine compositions comprises the sexual stage antigens Pfs25 and Pfs230C0, in particular in a recombinant fusion protein. The recombinant fusion protein comprises for example SEQ ID NO. 4, 26, 27 or SEQ ID NO. 28, or homologous polypeptides thereof, which are produced by recombinant or synthetic methods by substitution, insertion, addition or deletion of one or more amino acid residues.

In an advantageous embodiment, the mixture according to the present disclosure comprises four (4) recombinant polypeptides, wherein the different recombinant polypeptides comprises the following antigens:
  a) Polypeptide 1: PfCelTOS, the TSR-domain of PfCSP and the TSR-domain of PfTRAP
  b) Polypeptide 2: PfgAMA1
  c) Polypeptide 3: PfMsp1-19_EGF1, PfMsp4_EGF, PfMsp8_EGF1, PfMsp8_EGF2, and an N-terminal fragment of PfMsp3
  d) Polypeptide 4: Pfs25 and Pfs230C0.

In an advantageous embodiment, the mixture according to the present disclosure comprises four (4) recombinant polypeptides having the amino acid sequences of
  a) Polypeptide 1: SEQ ID NO. 1,
  b) Polypeptide 2: SEQ ID NO. 2
  c) Polypeptide 3: SEQ ID NO. 3, and
  d) Polypeptide 4: SEQ ID NO. 4,
or homologous polypeptides thereof, which are produced by recombinant or synthetic methods by substitution, insertion, addition or deletion of one or more amino acid residues.

The mixture can be a vaccine comprising five (5) different recombinant polypeptides.

In another advantageous embodiment, the mixture according to the present disclosure comprises five (5) recombinant polypeptides, wherein the different recombinant polypeptides comprises the following antigens:
  a) Polypeptide 10: PfAMA1-DICO1
  b) Polypeptide 11: PfAMA1-DICO2
  c) Polypeptide 12: PfAMA1-DICO3
  d) Polypeptide 8: Pfs25 and Pfs230C0 and
  e) Polypeptide 9: PfCelTOS, the TSR-domain of PfCSP and the TSR-domain of PfTRAP.

In an advantageous embodiment, the mixture according to the present disclosure comprises five (5) recombinant polypeptides having the amino acid sequences of
  a) Polypeptide 10: SEQ ID NO. 11
  b) Polypeptide 11: SEQ ID NO. 12
  c) Polypeptide 12: SEQ ID NO. 13
  d) Polypeptide 8: SEQ ID NO. 8
  a) Polypeptide 9: SEQ ID NO. 26.
or homologous polypeptides thereof, which are produced by recombinant or synthetic methods by substitution, insertion, addition or deletion of one or more amino acid residues.

In further advantageous embodiment, the mixture according to the present disclosure comprises five (5) recombinant polypeptides, wherein the different recombinant polypeptides comprises the following antigens:
  f) Polypeptide 10: PfAMA1-DICO1
  g) Polypeptide 11: PfAMA1-DICO2
  h) Polypeptide 12: PfAMA1-DICO3
  i) Polypeptide 13: Pfs25, Pfs230C0 and a PfRh5b and
  j) Polypeptide 14: PfCelTOS, the TSR-domain of PfCSP and the TSR-domain of PfTRAP a PfRh5a.

In a further advantageous embodiment, the mixture according to the present disclosure comprises five (5) recombinant polypeptides having the amino acid sequences of e) Polypeptide 10: SEQ ID NO. 11
f) Polypeptide 11: SEQ ID NO. 12
g) Polypeptide 12: SEQ ID NO. 13
h) Polypeptide 13: SEQ ID NO. 28
i) Polypeptide 14: SEQ ID NO. 9 or homologous polypeptides thereof, which are produced by recombinant or synthetic methods by substitution, insertion, addition or deletion of one or more amino acid residues.

The vaccine can comprise five (5) recombinant polypeptides, wherein the different recombinant polypeptides comprise the following antigens:
a) Polypeptide 1: PfAMA1-DICO1 and PfMsp1-19
b) Polypeptide 2: PfAMA1-DICO2 and PfRh2
c) Polypeptide 3: PfAMA1-DICO3, PfRIPR_EGF7/8
d) Polypeptide 4: PfCelTOS, the TSR-domain of PfCSP and the TSR-domain of PfTRAP and
e) Polypeptide 5: Pfs25 and Pfs230C0

In an advantageous embodiment, the mixture according to the present disclosure comprises five (5) recombinant polypeptides having the amino acid sequences of
a) Polypeptide 1: SEQ ID NO. 14
b) Polypeptide 2: SEQ ID NO. 15
c) Polypeptide 3: SEQ ID NO. 16
j) Polypeptide 4: SEQ ID NO. 8
d) Polypeptide 5: SEQ ID NO. 26.

or homologous polypeptides thereof, which are produced by recombinant or synthetic methods by substitution, insertion, addition or deletion of one or more amino acid residues.

In further advantageous embodiment, the mixture according to the present disclosure comprises five (5) recombinant polypeptides, wherein the different recombinant polypeptides comprises the following antigens:
a) Polypeptide 1: PfAMA1-DICO1
b) Polypeptide 2: PfAMA1-DICO2
c) Polypeptide 3: PfAMA1-DICO3
d) Polypeptide 4: Pfs25, Pfs230C0 and a PfRh5 peptide and
e) Polypeptide 5: PfCelTOS, the TSR-domain of PfCSP and the TSR-domain of PfTRAP a PfRh5 peptide.

In a further advantageous embodiment, the mixture according to the present disclosure comprises five (5) recombinant polypeptides having the amino acid sequences of
a) Polypeptide 1: SEQ ID NO. 11
b) Polypeptide 2: SEQ ID NO. 12
c) Polypeptide 3: SEQ ID NO. 13
d) Polypeptide 4: SEQ ID NO. 28
e) Polypeptide 5: SEQ ID NO. 9 or homologous polypeptides thereof, which are produced by recombinant or synthetic methods by substitution, insertion, addition or deletion of one or more amino acid residues.

For example, the recombinant polypeptides are comprised in the mixture in equimolar or any other ratios. In an advantageous embodiment, the recombinant polypeptides and/or antigens are comprised in the mixture in equimolar ratios.

In a further advantageous embodiment, the mixture according to the present disclosure comprises at least five (5) recombinant polypeptides selected from the groups 1, 2 and 3 (at least 3 proteins from group 2) having the amino acid sequences of
a) Group 1 (pre-erythrocyticstage): SEQ ID NO. 1 and 5-10
b) Group 1 (pre-erythrocyticstage): SEQ ID NO. 2, 3 and 11-22
c) Group 1 (pre-erythrocyticstage): SEQ ID NO. 4 and 23-28 or homologous polypeptides thereof, which are produced by recombinant or synthetic methods by substitution, insertion, addition or deletion of one or more amino acid residues.

Advantageous recombinant proteins, in particular recombinant fusion proteins comprised in the mixture suitable as human vaccines against *Plasmodium falciparum*: are listed in the following Table 1.

TABLE 1

Single-stage single or multi-domain proteins for *P. falciparum* vaccines

| SEQ ID | Domain(s) | Sequence |
|---|---|---|
| 1 | PfCelTOS,_PfCSP_TSR, PfTRAP_TSR (CCT-ERH) | MAFRGNNGHDSSSSLYGGSQFIEQLDNSFTSAFLESQSMNKIGDDLAETISN ELVSVLQKNSPTFLESSFDIKSEVKKHAKSMLKELIKVGLPSFENLVAENVKP PKVDPATYGIIVPVLTSLFNKVETAVGAINSDEIWNYNSPDVSESEESLSDD FFDAAGPSDKHIEQYLKKIQNSLSTEWSPCSVTCGNGIQVRIKPGSANKPKD ELDYENDIEKKICKMEKCSSVFNVVNSAAVAMAEKTASCGVWDEWSPCSV TCGKGTRSRKREILHEGCTSELQEQCEEERCLPKAAAHHHHHHSEKDEL |
| 2 | PfΔPropeptide gAMA1 (gAMA1-ERH) | MAIEIVERSNYMGNPWTEYMAKYDIEEVHGSGIRVDLGEDAEVAGTQYRLP SGKCPVFGKGIIIENSNTTFLTPVATGNQYLKDGGFAFPPTEPLMSPMTLDE MRHFYKDNKYVKNLDELTLCSRHAGNMIPDNDKNSNYKYPAVYDDKDKK CHILYIAAQENNGPRYCNKDESKRNSMFCFRPAKDISFQNYTYLSKNVVDN WEINCPRKNLQNAKFGLWVDGNCEDIPHVNEFPAIDLFECNKLVFELSASD QPKQYEQHLTDYEKIKEGFKNKNASMIKSAFLPTGAFKADRYKSHGKGYN WGNYNTETQKCEIFNVKPTCLINNSSYIATTALSHPIEVENNFPCSLYKDEI MKEIERESKRIKLNDNDDEGNKKIIAPRIFISDDKDSLKCPCDPEMVSNSTCR FFVCKCVERRAEVTSNNEVVVKEEYKDEYADIPEHKPTYDKMKAAAHHHH HHSEKDEL |
| 3 | PfMsp1-19_EGF1, PfMsp4_EGF, PfMsp8_EGF1, PfMsp8_EGF2, PlMSP3_N-Fragment (NME-ERH) | MAISQHQCVKKQCPENSGCFRHLDEREECKCLLNYKQEGDKCVAAGLEDE DLCKHNNGGCGDDKLCEYVGNRRVKCKCKEGYKLEGIECVELLAAGNNKVC ENTKCPLNSNCYVIDDEETCRCLPGFNNIKIDDEMNCVRDAAGDTLDCSRN NGGCDIHAKCSFINKQIVCECKDKFEGDGIYCSYSAAGKEIVKKYNLNLRNAI LNNNSQIENEENVNTTITGNDFSGGEFLWPGYTEELKAKKASEDAEKAAND AENASKEAEEAAKEAVNLKESDKSYTKAKEAATAASKAKKAVETALKAKD DAEKSSKADSISTKTKAAAHHHHHHSEKDEL |

TABLE 1-continued

Single-stage single or multi-domain proteins for *P. falciparum* vaccines

| SEQ ID | Domain(s) | Sequence |
|---|---|---|
| 4 | Pfs25, Pfs230_C0 (F0-ERH) | MVTVDTVCKRGFLIQMSGHLECKCENDLVLVNEETCEEKVLKCDEKTVNK PCGDFSKCIKIDGNPVSYACKCNLGYDMVNNVCIPNECKNVACGNGKCILDT SNPVKTGVCSCNIGINPNVQDQKCSKDGETKCSLKCLKENEACKAVDGIYK CDCKDGFIIDNEASICTAAVEYVDEKERQGEIYPFGDEEEKDEGGESFTYEKS EVDKTDLFKFIEGGEGDDVYKVDGSKVLLDDDTISRVSKKHTARDGEYGEY GEAVEDGENVIKIIRSVLQSGALPSVGVDELDKIDLSYETTES GDTAVSEDSYDKYASNNAAAHHHHHHSEKDEL |
| 5 | Propeptide-PfCelTOS,_PfCSP_TSR,PfTRAP_TSR (Propeptide-CCT) | QNYWEHPYQKSDVYHPINEHREHPKEYEYPLHQEHTYQQEDSGEDENTLQ HAYPIDHEGAEPAPQEQNLFSSMAFRGNNGHDSSSSLYGGSQFIEQLDNSFT SAFLESQSMNKIGDDLAETISNELVSVLQKNSPTFLESSFDIKSEVKKHAKSM LKELIKVGLPSFENLVAENVKPPKVDPATYGIIVPVLTSLFNKVETAVGAKVS DEIWNYNSPDVSESEEESLSDDFFDAAGPSDKHIEQYLKKIQNSLSTEWSPCS VTCGNGIQVRIKPGSANKPKDELDYENDIEKKICKMEKCSSVFNVVNSAAVA MAEKTASCGVWDEWSPCSVTCGKGTRSRKREILHEGCTSELQEQCEEERCL PK |
| 6 | Propeptide-PfCelTOS,_PfCSP_TSR,PfTRAP_TSR-Rh5a (Propeptide-CCT-Rh5a) | QNYWEHPYQKSDVYHPINEHREHPKEYEYPLHQEHTYQQEDSGEDENTLQ HAYPIDHEGAEPAPQEQNLFSSMAFRGNNGHDSSSSLYGGSQFIEQLDNSFT SAFLESQSMNKIGDDLAETISNELVSVLQKNSPTFLESSFDIKSEVKKHAKSM LKELIKVGLPSFENLVAENVKPPKVDPATYGIIVPVLTSLFNKVETAVGAINS DEIWNYNSPDVSESEEESLSDDFFDAAGPSDKHIEQYLKKIQNSLSTEWSPCS VTCGNGIQVRIKPGSANKPKDELDYENDIEKKICKMEKCSSVFNVVNSAAVA MAEKTASCGVWDEWSPCSVTCGKGTRSRKREILHEGCTSELQEQCEEERCL PKTNGIRYHYDEYIH |
| 7 | Propeptide-PfCelTOS,_PfCSP_TSR,PfTRAP_TSR-Rh5b (Propeptide-CCT-Rh5b) | QNYWEHPYQKSDVYHPINEHREHPKEYEYPLHQEHTYQQEDSGEDENTLQ HAYPIDHEGAEPAPQEQNLFSSMAFRGNNGHDSSSSLYGGSQFIEQLDNSFT SAFLESQSMNKIGDDLAETISNELVSVLQKNSPTFLESSFDIKSEVKKHAKSM LKELIKVGLPSFENLVAENVKPPKVDPATYGIIVPVLTSLFNKVETAVGAINS DEIWNYNSPDVSESEEESLSDDFFDAAGPSDKHIEQYLKKIQNSLSTEWSPCS VTCGNGIQVRIKPGSANKPKDELDYENDIEKKICKMEKCSSVFNVVNSAAVA MAEKTASCGVWDEWSPCSVTCGKGTRSRKREILHEGCTSELQEQCEEERCL PKYGKYIAVDAFIKKI |
| 8 | PfCelTOS,_PfCSP_TSR,PfTRAP_TSR (CCT) | FRGNNGHDSSSSLYGGSQFIEQLDNSFTSAFLESQSMNKIGDDLAETISNELV SVLQKNSPTFLESSFDIKSEVKKHAKSMLKELIKVGLPSFENLVAENVKPPK VDPATYGIIVPVLTSLFNKVETAVGAINSDEIWNYNSPDVSESEEESLSDDFF DAAGPSDKHIEQYLKKIQNSLSTEWSPCSVTCGNGIQVRIKPGSANKPKDEL DYENDIEKKICKMEKCSSVFNVVNSAAVAMAEKTASCGVVVDEWSPCSVTC GKGTRSRKREILHEGCTSELQEQCEEERCLPK |
| 9 | PfCelTOS,_PfCSP_TSR,PfTRAP_TSR_PfRh5a (CCT-Rh5a) | FRGNNGHDSSSSLYGGSQFIEQLDNSFTSAFLESQSMNKIGDDLAETISNELV SVLQKNSPTFLESSFDIKSEVKKHAKSMLKELIKVGLPSFENLVAENVKPPK VDPATYGIIVPVLTSLFNKVETAVGAKVSDEIWNYNSPDVSESEEESLSDDFF DAAGPSDKHIEQYLKKIQNSLSTEWSPCSVTCGNGIQVRIKPGSANKPKDEL DYENDIEKKICKMEKCSSVFNVVNSAAVAMAEKTASCGVVVDEWSPCSVTC GKGTRSRKREILHEGCTSELQEQCEEERCLPKTNGIRYHYDEYIH |
| 10 | PfCelTOS,_PfCSP_TSR,PfTRAP_TSR_PfRh5b (CCT-Rh5b) | FRGNNGHDSSSSLYGGSQFIEQLDNSFTSAFLESQSMNKIGDDLAETISNELV SVLQKNSPTFLESSFDIKSEVKKHAKSMLKELIKVGLPSFENLVAENVKPPK VDPATYGIIVPVLTSLFNKVETAVGAKVSDEIWNYNSPDVSESEEESLSDDFF DAAGPSDKHIEQYLKKIQNSLSTEWSPCSVTCGNGIQVRIKPGSANKPKDEL DYENDIEKKICKMEKCSSVFNVVNSAAVAMAEKTASCGVVVDEWSPCSVTC GKGTRSRKREILHEGCTSELQEQCEEERCLPKYGKYIAVDAFIKKI |
| 11 | PfAMA1-DIC01 | QNYVVEHPYQKSDVYHPINEHREHPKEYEYPLHQEHTYQQEDSGEDENTLQ HAYPIDHEGAEPAPQEQNLFSSIEIVERSNYMGNPWTEYMAKYDIEEVHGS GIRVDLGEDAEVAGTQYRLPSGKCPVFGKGIIIENSQTTFLTPVATENQDLK DGGFAFPPTKPLMSPMTLDQMRHFYKDNEYVKNLDELTLCSRHAGNMNP DNDKNSNYKYPAVYDDKDKKCHILYIAAQENNGPRYCNKDESKRNSMFCF RPAKDKSFQNYVYLSKNVVDNWEKVCPRKNLENAKFGLWVDGNCEDIPH VNEFSANDLFECNKLVFELSASDQPKQYEQHLTDYEKIKEGFKNKNADMIR SAFLPTGAFKADRYKSHGKGYNWGNYNRKTQKCEIFNVKPTCLINDKSYIA TTALSHPIEVEHNFPCSLYKDEIKKEIERESKRIKLNDNDDEGNKKIIAPRIFI SDDKDSLKCPCDPEIVSQSTCNFFVCKCVEKRAEVTSNNEVVVKEEYKDEYA DIPEHKPTYDK |
| 12 | PfAMA1-DIC02 | QNYVVEHPYQKSDVYHPINEHREHPKEYEYPLHQEHTYQQEDSGEDENTLQ HAYPIDHEGAEPAPQEQNLFSSIEIVERSNYMGNPWTEYMAKYDIEEVHGS GIRVDLGEDAEVAGTQYRLPSGKCPVFGKGIIIENSQTTFLKPVATGNQDLK DGGFAFPPTNPLISPMTLNGMRDFYKNNEYVKNLDELTLCSRHAGNMNPD NDENSNYKYPAVYDYNDKKCHILYIAAQENNGPRYCNKDESKRNSMFCFRP AKDKLFENYVYLSKNVVHNWEEVCPRKNLENAKFGLWVDGNCEDIPHVN EFSANDLFECNKLVFELSASDQPKQYEQHLTDYEKIKEGFKNKNADMIRSA FLPTGAFKADRYKSRGKGYNWGNYNRKTQKCEIFNVKPTCLINDKSYIATT |

TABLE 1-continued

Single-stage single or multi-domain proteins for *P. falciparum* vaccines

| SEQ ID | Domain(s) | Sequence |
|---|---|---|
| | | ALSHPIEVENNFPCSLYKNEIMKEIERESKRIKLNDNDDEGNKKIIAPRIFISD<br>DKDSLKCPCDPEMVSQSTCRFFVCKCVERRAEVTSNNEVVVKEEYKDEYAD<br>IPEHKPTYDN |
| 13 | PfAMA1-DIC03 | QNYVVEHPYQKSDVYHPINEHREHPKEYEYPLHQEHTYQQEDSGEDENTLQ<br>HAYPIDHEGAEPAPQEQNLFSSIEIVERSNYMGNPWTEYMAKYDIEEVHGS<br>GIRVDLGEDAEVAGTQYRLPSGKCPVFGKGIIIENSKTTFLTPVATENQDLKD<br>GGFAFPPTEPLMSPMTLDDMRDLYKDNKYVKNLDELTLCSRHAGNMIPDN<br>DKNSNYKYPAVYDYEDKKCHILYIAAQENNGPRYCNKDQSKRNSMFCFRPA<br>KDISFQNYVYLSKNVVDNWEINCPRKNLQNAKFGLWVDGNCEDIPHVNEF<br>SAIDLFECNKLVFELSASDQPKQYEQHLTDYEKIKEGFKNKNADMIRSAFLP<br>TGAFKADRYKSHGKGYNWGNYNTETQKCEIFNVKPTCLINDKSYIATTALS<br>HPNEVEHNFPCSLYKDEIKKEIERESKRIKLNDNDDEGNKKIIAPRIFISDDID<br>SLKCPCAPEIVSQSTCNFFVCKCVEKRAEVTSNNEVVVKEEYKDEYADIPEH<br>KPTYDK |
| 14 | PfAMA1-<br>DIC01_Msp1-<br>19FUP | QNYVVEHPYQKSDVYHPINEHREHPKEYEYPLHQEHTYQQEDSGEDENTLQ<br>HAYPIDHEGAEPAPQEQNLFSSIEIVERSNYMGNPWTEYMAKYDIEEVHGS<br>GIRVDLGEDAEVAGTQYRLPSGKCPVFGKGIIIENSQTTFLTPVATENQDLK<br>DGGFAFPPTKPLMSPMTLDQMRHFYKDNEYVKNLDELTLCSRHAGNMNP<br>DNDKNSNYKYPAVYDDKDKKCHILYIAAQENNGPRYCNKDESKRNSMFCF<br>RPAKDKSFQNYVYLSKNVVDNWEINCPRKNLENAKFGLWVDGNCEDIPH<br>VNEFSANDLFECNKLVFELSASDQPKQYEQHLTDYEKIKEGFKNKNADMIR<br>SAFLPTGAFKADRYKSHGKGYNWGNYNRKTQKCEIFNVKPTCLINDKSYIA<br>TTALSHPIEVEHNFPCSLYKDEIKKEIERESKRIKLNDNDDEGNKKIIAPRIFI<br>SDDKDSLKCPCDPEIVSQSTCNFFVCKCVEKRAEVTSNNEVVVKEEYKDEYA<br>DIPEHKPTYDKMAAVAMAISQHQCVKKQCPENSGCFRHLDEREECKCLLNY<br>KQEGDKCVENPNPTCNENNGGCDADAKCTEEDSGSNGKKITCECTKPDSYP<br>LFDGIFCSSSN |
| 15 | PfAMA1-<br>DIC02_Rh2 | QNYVVEHPYQKSDVYHPINEHREHPKEYEYPLHQEHTYQQEDSGEDENTLQ<br>HAYPIDHEGAEPAPQEQNLFSSIEIVERSNYMGNPWTEYMAKYDIEEVHGS<br>GIRVDLGEDAEVAGTQYRLPSGKCPVFGKGIIIENSQTTFLKPVATGNQDLK<br>DGGFAFPPTNPLISPMTLNGMRDFYKNNEYVKNLDELTLCSRHAGNMNPD<br>NDENSNYKYPAVYDYNDKKCHILYIAAQENNGPRYCNKDESKRNSMFCFRP<br>AKDKLFENYVYLSKNVVHNWEEVCPRKNLENAKFGLWVDGNCEDIPHVN<br>EFSANDLFECNKLVFELSASDQPKQYEQHLTDYEKIKEGFKNKNADMIRSA<br>FLPTGAFKADRYKSRGKGYNWGNYNRKTQKCEIFNVKPTCLINDKSYIATT<br>ALSHPIEVENNFPCSLYKNEIMKEIERESKRIKLNDNDDEGNKKIIAPRIFISD<br>DKDSLKCPCDPEMVSQSTCRFFVCKCVERRAEVTSNNEVVVKEEYKDEYAD<br>IPEHKPTYDNMAAVAMAKKYETYVDMKTIESKYTTVMTLSEHLLEYAMDV<br>LKANPQKPIDPKANLDSEVVKLQIKINEKSNELDNAASQVKTLIIIMKSFYDII<br>ISEKASMDEMEKKELSLNNYIEKTDY |
| 16 | PfAMA1-<br>DIC03_RIPR7/8 | QNYVVEHPYQKSDVYHPINEHREHPKEYEYPLHQEHTYQQEDSGEDENTLQ<br>HAYPIDHEGAEPAPQEQNLFSSIEIVERSNYMGNPWTEYMAKYDIEEVHGS<br>GIRVDLGEDAEVAGTQYRLPSGKCPVFGKGIIIENSKTTFLTPVATENQDLKD<br>GGFAFPPTEPLMSPMTLDDMRDLYKDNKYVKNLDELTLCSRHAGNMIPDN<br>DKNSNYKYPAVYDYEDKKCHILYIAAQENNGPRYCNKDQSKRNSMFCFRPA<br>KDISFQNYVYLSKNVVDNWEKVCPRKNLQNAKFGLWVDGNCEDIPHVNEF<br>SAIDLFECNKLVFELSASDQPKQYEQHLTDYEKIKEGFKNKNADMIRSAFLP<br>TGAFKADRYKSHGKGYNWGNYNTETQKCEIFNVKPTCLINDKSYIATTALS<br>HPNEVEHNFPCSLYKDEIKKEIERESKRIKLNDNDDEGNKKIIAPRIFISDDID<br>SLKCPCAPEIVSQSTCNFFVCKCVEKRAEVTSNNEVVVKEEYKDEYADIPEH<br>KPTYDKMAAGYCKDINCKENEECSIVNFKPECVCKENLKKNNKGECIAASC<br>LINEGNCPKDSKCIYREYKPHECVCNKQGHVAVNGKCV |
| 17 | PfAMA1-<br>DIC01Δ<br>Propeptide | IEIVERSNYMGNPWTEYMAKYDIEEVHGSGIRVDLGEDAEVAGTQYRLPSG<br>KCPVFGKGIIIENSQTTFLTPVATENQDLKDGGFAFPPTKPLMSPMTLDQM<br>RHFYKDNEYVKNLDELTLCSRHAGNMNPDNDKNSNYKYPAVYDDKDKKC<br>HILYIAAQENNGPRYCNKDESKRNSMFCFRPAKDKSFQNYVYLSKNVVDN<br>WEKVCPRKNLENAKFGLWVDGNCEDIPHVNEFSANDLFECNKLVFELSAS<br>DQPKQYEQHLTDYEKIKEGFKNKNADMIRSAFLPTGAFKADRYKSHGKGY<br>NWGNYNRKTQKCEIFNVKPTCLINDKSYIATTALSHPIEVEHNFPCSLYKDE<br>IKKEIERESKRIKLNDNDDEGNKKIIAPRIFISDDKDSLKCPCDPEIVSQSTCN<br>FFVCKCVEKRAEVTSNNEVVVKEEYKDEYADIPEHKPTYDK |
| 18 | PfAMA1-<br>DIC02Δ<br>Propeptide | IEIVERSNYMGNPWTEYMAKYDIEEVHGSGIRVDLGEDAEVAGTQYRLPSG<br>KCPVFGKGIIIENSQTTFLKPVATGNQDLKDGGFAFPPTNPLISPMTLNGMR<br>DFYKNNEYVKNLDELTLCSRHAGNMNPDNDENSNYKYPAVYDYNDKKCHI<br>LYIAAQENNGPRYCNKDESKRNSMFCFRPAKDKLFENYVYLSKNVVHNW<br>EEVCPRKNLENAKFGLWVDGNCEDIPHVNEFSANDLFECNKLVFELSASDQP<br>KQYEQHLTDYEKIKEGFKNKNADMIRSAFLPTGAFKADRYKSRGKGYNWG<br>NYNRKTQKCEIFNVKPTCLINDKSYIATTALSHPIEVENNFPCSLYKNEIMKE<br>IERESKRIKLNDNDDEGNKKIIAPRIFISDDKDSLKCPCDPEMVSQSTCRFFV<br>CKCVERRAEVTSNNEVVVKEEYKDEYADIPEHKPTYDN |

TABLE 1-continued

Single-stage single or multi-domain proteins for *P. falciparum* vaccines

| SEQ ID | Domain(s) | Sequence |
|---|---|---|
| 19 | PfAMA1-DIC03Δ Propeptide | IEIVERSNYMGNPWTEYMAKYDIEEVHGSGIRVDLGEDAEVAGTQYRLPSG<br>KCPVFGKGIIIENSKTTFLTPVATENQDLKDGGFAFPPTEPLMSPMTLDDM<br>RDLYKDNKYVKNLDELTLCSRHAGNMIPDNDKNSNYKYPAVYDYEDKKCH<br>ILYIAAQENNGPRYCNKDQSKRNSMFCFRPAKDISFQNYVYLSKNVVDNWE<br>KVCPRKNLQNAKFGLWVDGNCEDIPHVNEFSAIDLFECNKLVFELSASDQP<br>KQYEQHLTDYEKIKEGFKNKNADMIRSAFLPTGAFKADRYKSHGKGYNWG<br>NYNTETQKCEIFNVKPTCLINDKSYIATTALSHPNEVEHNFPCSLYKDEIKK<br>EIERESKRIKLNDNDDEGNKKIIAPRIFISDDIDSLKCPCAPEIVSQSTCNFFVC<br>KCVEKRAEVTSNNEVVVKEEYKDEYADIPEHKPTYDK |
| 20 | PfAMA1-DIC01_Msp1-19FUP ΔPropeptide | IEIVERSNYMGNPWTEYMAKYDIEEVHGSGIRVDLGEDAEVAGTQYRLPSG<br>KCPVFGKGIIIENSQTTFLTPVATENQDLKDGGFAFPPTKPLMSPMTLNGMR<br>RHFYKDNEYVKNLDELTLCSRHAGNMNPDNDKNSNYKYPAVYDDKDKKC<br>HILYIAAQENNGPRYCNKDESKRNSMFCFRPAKDKSFQNYVYLSKNVVDN<br>WEKVCPRKNLENAKFGLWVDGNCEDIPHVNEFSANDLFECNKLVFELSAS<br>DQPKQYEQHLTDYEKIKEGFKNKNADMIRSAFLPTGAFKADRYKSHGKGY<br>NWGNYNRKTQKCEIFNVKPTCLINDKSYIATTALSHPIEVEHNFPCSLYKDE<br>IKKEIERESKRIKLNDNDDEGNKKIIAPRIFISDDKDSLKCPCDPEIVSQSTCN<br>FFVCKCVEKRAEVTSNNEVVVKEEYKDEYADIPEHKPTYDKMAAVAMAISQ<br>HQCVKKQCPENSGCFRHLDEREECKCLLNYKQEGDKCVENPNPTCNENNG<br>GCDADAKCTEEDSGSNGKKITCECTKPDSYPLFDGIFCSSSN |
| 21 | PfAMA1-DIC02_Rh2 ΔPropeptide | IEIVERSNYMGNPWTEYMAKYDIEEVHGSGIRVDLGEDAEVAGTQYRLPSG<br>KCPVFGKGIIIENSQTTFLKPVATGNQDLKDGGFAFPPTNPLISPMTLNGMR<br>DFYKNNEYVKNLDELTLCSRHAGNMNPDNDENSNYKYPAVYDYNDKKCHI<br>LYIAAQENNGPRYCNKDESKRNSMFCFRPAKDKLFENYVYLSKNVVHNWE<br>EVCPRKNLENAKFGLWVDGNCEDIPHVNEFSANDLFECNKLVFELSASDQP<br>KQYEQHLTDYEKIKEGFKNKNADMIRSAFLPTGAFKADRYKSRGKGYNWG<br>NYNRKTQKCEIFNVKPTCLINDKSYIATTALSHPIEVENNFPCSLYKNEIMKE<br>IERESKRIKLNDNDDEGNKKIIAPRIFISDDKDSLKCPCDPEMVSQSTCRFFV<br>CKCVERRAEVTSNNEVVVKEEYKDEYADIPEHKPTYDNMAAVAMAKKYET<br>YVDMKTIESKYTTVMTLSEHLLEYAMDVLKANPQKPIDPKANLDSEVVKLQ<br>IKINEKSNELDNAASQVKTLIIIMKSFYDIIISEKASMDEMEKKELSLNNYIEK<br>TDY |
| 22 | PfAMA1-DIC03_RIPR7/8 ΔPropeptide | IEIVERSNYMGNPWTEYMAKYDIEEVHGSGIRVDLGEDAEVAGTQYRLPSG<br>KCPVFGKGIIIENSKTTFLTPVATENQDLKDGGFAFPPTEPLMSPMTLDDM<br>RDLYKDNKYVKNLDELTLCSRHAGNMIPDNDKNSNYKYPAVYDYEDKKCH<br>ILYIAAQENNGPRYCNKDQSKRNSMFCFRPAKDISFQNYVYLSKNVVDNWE<br>KVCPRKNLQNAKFGLWVDGNCEDIPHVNEFSAIDLFECNKLVFELSASDQP<br>KQYEQHLTDYEKIKEGFKNKNADMIRSAFLPTGAFKADRYKSHGKGYNWG<br>NYNTETQKCEIFNVKPTCLINDKSYIATTALSHPNEVEHNFPCSLYKDEIKK<br>EIERESKRIKLNDNDDEGNKKIIAPRIFISDDIDSLKCPCAPEIVSQSTCNFFVC<br>KCVEKRAEVTSNNEVVVKEEYKDEYADIPEHKPTYDKMAAGYCKDINCKE<br>NEECSIVNFKPECVCKENLKKNNKGECIAASCLINEGNCPKDSKCIYREYKP<br>HECVCNKQGHVAVNGKCV |
| 23 | Propeptide-25_230C0 (Propeptide-F0) | QNYWEHPYQKSDVYHPINEHREHPKEYEYPLHQEHTYQQEDSGEDENTLQ<br>HAYPIDHEGAEPAPQEQNLFSSMVTVDTVCKRGFLIQMSGHLECKCENDLV<br>LVNEETCEEKVLKCDEKTVNKPCGDFSKCIKIDGNPVSYACKCNLGYDMVN<br>NVCIPNECKNVACGNGKCILDTSNPVKTGVCSCNIGKVPNVQDQKCSKDGE<br>TKCSLKCLKENEACKAVDGIYKCDCKDGFIIDNEASICTAAVEYVDEKERQG<br>EIYPFGDEEEKDEGGESFTYEKSEVDKTDLFKFIEGGEGDDVYKVDGSKVLL<br>DDDTISRVSKKHTARDGEYGEYGEAVEDGENVIKIIRSVLQSGALPSVGVDEL<br>DKIDLSYETTESGDTAVSEDSYDKYASNN |
| 24 | Propeptide-25_230C0-Rh5a (Propeptide-F0-Rh5a) | QNYWEHPYQKSDVYHPINEHREHPKEYEYPLHQEHTYQQEDSGEDENTLQ<br>HAYPIDHEGAEPAPQEQNLFSSMVTVDTVCKRGFLIQMSGHLECKCENDLV<br>LVNEETCEEKVLKCDEKTVNKPCGDFSKCIKIDGNPVSYACKCNLGYDMVN<br>NVCIPNECKNVACGNGKCILDTSNPVKTGVCSCNIGKVPNVQDQKCSKDGE<br>TKCSLKCLKENEACKAVDGIYKCDCKDGFIIDNEASICTAAVEYVDEKERQG<br>EIYPFGDEEEKDEGGESFTYEKSEVDKTDLFKFIEGGEGDDVYKVDGSKVLL<br>DDDTISRVSKKHTARDGEYGEYGEAVEDGENVIKIIRSVLQSGALPSVGVDEL<br>DKIDLSYETTESGDTAVSEDSYDKYASNNNGIRYHYDEYIH |
| 25 | Propeptide-25_230C0-Rh5b (Propeptide-F0-Rh5b) | QNYWEHPYQKSDVYHPINEHREHPKEYEYPLHQEHTYQQEDSGEDENTLQ<br>HAYPIDHEGAEPAPQEQNLFSSMVTVDTVCKRGFLIQMSGHLECKCENDLV<br>LVNEETCEEKVLKCDEKTVNKPCGDFSKCIKIDGNPVSYACKCNLGYDMVN<br>NVCIPNECKNVACGNGKCILDTSNPVKTGVCSCNIGKVPNVQDQKCSKDGE<br>TKCSLKCLKENEACKAVDGIYKCDCKDGFIIDNEASICTAAVEYVDEKERQG<br>EIYPFGDEEEKDEGGESFTYEKSEVDKTDLFKFIEGGEGDDVYKVDGSKVLL<br>DDDTISRVSKKHTARDGEYGEYGEAVEDGENVIKIIRSVLQSGALPSVGVDEL<br>DKIDLSYETTESGDTAVSEDSYDKYASNNYGKYIAVDAFIKKI |

TABLE 1-continued

Single-stage single or multi-domain proteins for *P. falciparum* vaccines

| SEQ ID | Domain(s) | Sequence |
|---|---|---|
| 26 | 25_230C0 (F0) | VTVDTVCKRGFLIQMSGHLECKCENDLVLVNEETCEEKVLKCDEKTVNKPC GDFSKCIKIDGNPVSYACKCNLGYDMVNNVCIPNECKNVACGNGKCILDTSN PVKTGVCSCNIGKVPNVQDQKCSKDGETKCSLKCLKENEACKAVDGIYKCD CKDGFIIDNEASICTAAVEYVDEKERQGEIYPFGDEEEKDEGGESFTYEKSEV DKTDLFKFIEGGEGDDVYKVDGSKVLLDDDTISRVSKKHTARDGEYGEYGE AVEDGENVIKIIRSVLQSGALPSVGVDELDKIDLSYETTESGDTAVSEDSYDK YASNN |
| 27 | Pfs25, Pfs230_C0_ PfRh5a (F0-Rh5a) | VTVDTVCKRGFLIQMSGHLECKCENDLVLVNEETCEEKVLKCDEKTVNKPC GDFSKCIKIDGNPVSYACKCNLGYDMVNNVCIPNECKNVACGNGKCILDTSN PVKTGVCSCNIGKVPNVQDQKCSKDGETKCSLKCLKENEACKAVDGIYKCD CKDGFIIDNEASICTAAVEYVDEKERQGEIYPFGDEEEKDEGGESFTYEKSEV DKTDLFKFIEGGEGDDVYKVDGSKVLLDDDTISRVSKKHTARDGEYGEYGE AVEDGENVIKIIRSVLQSGALPSVGVDELDKIDLSYETTES GDTAVSEDSYDKYASNNGIRYHYDEYIH |
| 28 | Pfs25, Pfs230_C0_ PfRh5b (F0-Rh5b) | VTVDTVCKRGFLIQMSGHLECKCENDLVLVNEETCEEKVLKCDEKTVNKPC GDFSKCIKIDGNPVSYACKCNLGYDMVNNVCIPNECKNVACGNGKCILDTSN PVKTGVCSCNIGKVPNVQDQKCSKDGETKCSLKCLKENEACKAVDGIYKCD CKDGFIIDNEASICTAAVEYVDEKERQGEIYPFGDEEEKDEGGESFTYEKSEV DKTDLFKFIEGGEGDDVYKVDGSKVLLDDDTISRVSKKHTARDGEYGEYGE AVEDGENVIKIIRSVLQSGALPSVGVDELDKIDLSYETTES GDTAVSEDSYDKYASNNYGKYIAVDAFIKKI |
| 29 | PfCFelTOS_ | FRGNNGHDSSSSLYGGSQFIEQLDNSFTSAFLESQSMNKIGDDLAETISNELV SVLQKNSPTFLESSFDIKSEVKKHAKSMLKELIKVGLPSFENLVAENVKPPK VDPATYGIIVPVLTSLFNKVETAVGAINSDEIWNYNSPDVSESEEESLSDDFF D |
| 30 | PfCSP_TSR | GPSDKHIEQYLKKIQNSLSTEWSPCSVTCGNGIQVRIKPGSANKPKDELDYE NDIEKKICKMEKCSSVFNVVNS |
| 31 | PfTRAP_TSR | EKTASCGVWDEWSPCSVTCGKGTRSRKREILHEGCTSELQEQCEEERCLPK |
| 32 | PfMSP1_19_EGF1 | ISQHQCVKKQCPENSGCFRHLDEREECKCLLNYKQEGDKCV |
| 33 | PfMSP4_EGF | GLEDEDLCKHNNGGCGDDKLCEYVGNRRVKCKCKEGYKLEGIECVELL |
| 34 | PfMSP8_EGF1 | GNNKVCENTKCPLNSNCYVIDDEETCRCLPGFNNIKIDDEMNCVRD |
| 35 | PfMSP8_EGF2 | GDTLDCSRNNGGCDIHAKCSFINKQIVCECKDKFEGDGIYCSYS |
| 36 | PfMSP3_N-Fragment | GKEIVKKYNLNLRNAILNNNSQIENEENVNTTITGNDFSGGEFLWPGYTEEL KAKKASEDAEKAANDAENASKEAEEEAAKEAVNLKESDKSYTKAKEAATAA SKAKKAVETALKAKDDAEKSSKADSISTKTK |
| 37 | PfMSP1_19 | ISQHQCVKKQCPENSGCFRHLDEREECKCLLNYKQEGDKCVENPNPTCNEN NGGCDADAKCTEEDSGSNGKKITCECTKPDSYPLFDGIFCSSSN |
| 38 | PfRh2 | KKYETYVDMKTIESKYTTVMTLSEHLLEYAMDVLKANPQKPIDPKANLDSE VVKLQIKINEKSNELDNAASQVKTLIIIMKSFYDIIISEKASMDEMEKKELSLN NYIEKTDY |
| 39 | PfRIPR7/8 | GYCKDINCKENEECSIVNFKPECVCKENLKKNNKGECIAASCLINEGNCPKD SKCIYREYKPHECVCNKQGHVAVNGKCV |
| 40 | PfRipr_EGF7 | GYCKDINCKENEECSIVNFKPECVCKENLKKNNKGECI |
| 41 | PfRipr_EGF8 | SCLINEGNCPKDSKCIYREYKPHECVCNKQGHVAVNGKCV |
| 42 | PfRh5a (AA353-365) | TNGIRYHYDEYIH |
| 43 | PfRh5b (AA200-213) | YGKYIAVDAFIKKI |
| 44 | Pfs25 | VTVDTVCKRGFLIQMSGHLECKCENDLVLVNEETCEEKVLKCDEKTVNKPC GDFSKCIKIDGNPVSYACKCNLGYDMVNNVCIPNECKNVACGNGKCILDTSN PVKTGVCSCNIGINPNVQDQKCSKDGETKCSLKCLKENEACKAVDGIYKCD CKDGFIIDNEASICT |
| 45 | Pfs230C0 | EYVDEKERQGEIYPFGDEEEKDEGGESFTYEKSEVDKTDLFKFIEGGEGDDV YINDGSKVLLDDDTISRVSKKHTARDGEYGEYGEAVEDGENVIKIIRSVLQS GALPSVGVDELDKIDLSYETTESGDTAVSEDSYDKYASNN |

Further embodiments relates to methods for conjugating the recombinant protein to itself or to other molecules, proteins or carriers, in particular by random ways or by using site-directed coupling methods. In particular, site directed coupling can be accommodated to N-glycosylation site specifically retained within or introduced into the recombinant protein.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation or de-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the properties of the proteins as explored herein.

The term "modification" as used herein, refers for example to substitutions, insertions or deletions of amino acid residues at specific positions in an amino acid sequence as well as the phosphorylation, acetylation like palmitoylation, methylation, sulphation, glycosylation, lipidation like isoprenylation, farnesylation, attachment of a fatty acid moiety, glypiation and/or ubiquitinylation of specific positions on the polypeptide, or combinations thereof.

The term "modifying", as used herein, includes changing one or more amino acids in the antibodies or antigen-binding portions thereof. The change can be produced by adding, substituting or deleting an amino acid at one or more positions. The change can be produced using known techniques, such as PCR mutagenesis.

The term "homologous polypeptide" according to the present disclosure comprises any recombinant protein with a sequence identity of at least 70% or preferably at least 80%, 85%, 90%, 95%, 97% or 99% to the recombinant proteins in the mixtures or vaccine compositions according to the present disclosure.

The term "variant" means a homologous polypeptide to the original non-variant polypeptide and could be recognized by at least one antibody binding to the original non-variant polypeptide, wherein the variant comprises an alteration, i.e., a substitution, insertion, and/or deletion, at one or more (several) positions.

Homology is defined as an analogue or variant of the fusion protein of the present disclosure. The fusion protein is characterised by specific amino acids and is encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". Substitutions are preferably silent substitutions in the codon usage which will not lead to any change in the amino acid sequence, but may be introduced to enhance the expression of the protein. According to Table 4 amino acids in the same block of the second column and preferably in the same line of the fourth column may be substituted for each other. The amino acids in the second and fourth column are indicated in one-letter code.

In another aspect, the present disclosure pertains to An isolated nucleic acid molecule or a plurality of nucleic acid molecules encoding
 a) polypeptides having the sequence of SEQ ID NO. 1, SEQ ID NO. 2, SEQ ID NO. 3 and SEQ ID NO. 4
 b) polypeptides having the sequence of SEQ ID NO. 8, SEQ ID NO. 11, SEQ ID NO. 12, SEQ ID NO. 13 and SEQ ID NO. 26
 c) polypeptides having the sequence of SEQ ID NO. 9, SEQ ID NO. 11, SEQ ID NO. 12, SEQ ID NO. 13 and SEQ ID NO. 28
 d) polypeptides having the sequence of SEQ ID NO. 8, SEQ ID NO. 14, SEQ ID NO. 15, SEQ ID NO. 16 and SEQ ID NO. 26
 e) polypeptides having the sequence of SEQ ID NO. 9, SEQ ID NO. 14, SEQ ID NO. 15, SEQ ID NO. 16 and SEQ ID NO. 28
 f) for a modified form of the polypeptides of a)-i), preferably in which one or more amino acid residues are conservatively substituted
 g) a nucleic acid molecule that is capable of hybridizing to any of the nucleic acid molecules of a)-i) under stringent conditions
 h) a nucleic acid molecule that is capable of hybridizing to the complement of any of the nucleic acid molecules of a)-i) under stringent conditions
 i) a nucleic acid molecule having a sequence identity of at least 85% with any of the nucleic acid molecules of a)-i)
 j) or a complement of any of the nucleic acid molecules of a)-i).

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The terms "conservative mutation", or "conservative substitution", respectively, refer to an amino acid mutation that a person skilled in the art would consider a conservative to a first mutation. "Conservative" in this context means a similar amino acid in terms of the amino acid characteristics. If, for example, a mutation leads at a specific position to a substitution of a non-aliphatic amino acid residue (e.g. Ser) with an aliphatic amino acid residue (e.g. Leu) then a substitution at the same position with a different aliphatic amino acid (e.g. lie or Val) is referred to as a conservative mutation. Further amino acid characteristics include size of the residue, hydrophobicity, polarity, charge, pK-value, and other amino acid characteristics known in the art. Accordingly, a conservative mutation may include substitution such as basic for basic, acidic for acidic, polar for polar etc. The sets of amino acids thus derived are likely to be conserved for structural reasons.

The present disclosure is also directed to vectors comprising a nucleotide molecule of the present disclosure. The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

In advantageous embodiments, the nucleic sequences of the recombinant proteins can be inserted into the plant expression vector pTRAkc as NcoI and NotI fragments. pTRAkc is an example of a plant expression vector, which can be electroporated into agrobacteria and subsequently infiltrated into tobacco plants (Boes, A. et al. 2011). Other protein expression systems are also known in the art and are contemplated herein.

The present disclosure is also directed to host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell which comprises a recombinant vector of the invention may also be referred to as a "recombinant host cell".

The term "host cell(s)" refers to cell(s) which may be used in a process for purifying a recombinant protein in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archeobacteria, bacterial cells, insect cells, yeast, mammal cells, and/or plant cells. Bacteria envisioned as host cells can be either gram-negative or gram-positive, e.g. *Escherichia coli, Erwinia* sp., *Klebsellia* sp., *Lactobacillus* sp. or *Bacillus subtilis*. Typical yeast host cells are selected from the group consisting of *Saccharomyces cerevisiae*, and *Pichia pastoris*.

In advantageous embodiments, the host cell is a *Nicotiana benthamiana* plant cell, *Nicotiana tabacum* plant cell or BY2 cells thereof, if mammalian, it is preferably a CHO, COS, NSO or 293 cell, if yeast, it is preferably *Pichia pastoris*.

Plants for use in accordance with the present disclosure include Angiosperms, Bryophytes (e g, Hepaticae, Musci, etc), Ptepdophytes (e g, ferns, horsetails, lycopods), Gymnosperms (e g, conifers, cycase, Ginko, Gnetales), and Algae (e g, Chlorophyceae, Phaeophyceae, Rhodophyceae, Myxophyceae, Xanthophyceae, and Euglenophyceae). Exemplary plants are members of the family Leguminosae (Fabaceae, e g, pea, alfalfa, soybean), Gramineae (Poaceae, e g, corn, wheat, nee), Solanaceae, particularly of the genus *Lycopersicon* (e g, tomato), Solanium (e g, potato, eggplant), Capsium (e g, pepper), or *Nicotiana* (e g, tobacco), Umbelhferae, particularly of the genus *Daucus* (e g, carrot), *Apium* (e g, celery), or Rutaceae (e g, oranges), Compositae, particularly of the genus *Lactuca* (e g, lettuce), Brassicaceae (Cruciferae), particularly of the genus *Brassica* or *Sinapis* In certain aspects, plants in accordance with the invention maybe species of *Brassica* or *Arabidopsis* Some exemplary Brassicaceae family members include *Brassica campestns, B cannata, B juncea, B napus, B nigra, B oleraceae, B tournifortu, Sinapis alba*, and *Raphanus sativus* Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower etc.

To express a recombinant protein according to the present disclosure, a DNA encoding the fusion protein or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The folded polypeptide (recombinant fusion protein according to this disclosure) may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct recombinant vectors and design protocols for recombinant gene expression. For further details see, for example, Molecular Cloning: a Laboratory Manual: 2nd edition, Sambrook et al, 1989, Cold Spring Harbor Laboratory Press (or later editions of this work) and Current Protocols in Molecular Biology, Second Edition, Ausubel et al. eds., John Wiley & Sons, 1992, which are incorporated herein by reference.

In an advantageous embodiment, the expression vectors may be delivered to plants according to known techniques. For example, vectors themselves may be directly applied to plants (e g, via abrasive inoculations, mechanized spray inoculations, vacuum infiltration, particle bombardment, or electroporation). Alternatively or additionally, virons may be prepared (e g, from already infected plants), and may be applied to other plants according to known techniques. A wide variety of viruses are known that infect various plant species, and can be employed for polynucleotide expression according to the present invention (see, for example, in The Classification and Nomenclature of Viruses, "Sixth Report of the International Committee on Taxonomy of Viruses" (Ed Murphy et al), Springer Verlag New York, 1995, Grierson et al, Plant Molecular Biology, Blackie, London, pp 126-146, 1984, Gluzman er al, Communications in Molecular Biology Viral Vectors, Cold Spring Harbor Laboratory, Cold Spring Harbor, N.Y., pp 172-189, 1988, and Mathew, Plant Viruses Online, all of which are incorporated herein by reference) In certain embodiments, rather than delivering a single viral vector to a plant cell, multiple different vectors are delivered which, together, allow for replication (and, optionally cell-to-cell and/or long distance movement) of viral vector(s) Some or all of the proteins may be encoded by the genome of transgenic plants. In certain aspects, described in further detail herein, these systems include one or more viral vector components.

Further aspects of the disclosure relate to: a method of expressing in a host cell a recombinant protein as described herein from a nucleic acid molecule described herein; a host cell capable of expressing a fusion protein as described herein in appropriate culture conditions for producing said protein; a method of producing a recombinant protein comprising culturing such a host cell under appropriate conditions, which method may further comprise isolating said protein from the cell culture, and which method may further comprise admixing the isolated fusion protein with a suitable further component (which may, for example, be another protein or an excipient or carrier).

As discussed above, in accordance with the present disclosure, the recombinant proteins may be produced in any desirable system. Vector constructs and expression systems are well known in the art and may be adapted to incorporate use of recombinant fusion polypeptides provided herein. For example, transgenic plant production is known and generation of constructs and plant production maybe adapted according to known techniques in the art. In some embodiments, transient expression systems in plants are desirable (see international patent application WO10037063A2).

In general, standard methods known in the art may be used for culturing or growing plants, plant cells, and/or plant tissues in accordance with the disclosure (e.g. clonal plants, clonal plant cells, clonal roots, clonal root lines, sprouts, sprouted seedlings, plants, etc) for production of recombinant polypeptides. A wide variety of culture media and bioreactors have been employed to culture hairy root cells, root cell lines, and plant cells (see for example Rao et al, 2002, Biotechnol Adv, 20 101).

In a certain embodiments, recombinant polypeptides in accordance with the present description may be produced by any known method. In some embodiments, a fusion protein is expressed in a plant or portion thereof. Proteins may be isolated and purified in accordance with conventional conditions and techniques known in the art. These include methods such as extraction, precipitation, chromatography, affinity chromatography, electrophoresis, and the like. The present invention involves purification and affordable scaling up of production of recombinant polypeptide(s) using any of a variety of plant expression systems known in the art and provided herein.

In some embodiments of the present disclosure, it will be desirable to isolate recombinant polypeptide(s) for the vaccine products. Where a protein in accordance with the disclosure is produced from plant tissue(s) or a portion thereof, e g, roots, root cells, plants, plant cells, that express them, methods known in the art may be used for any of partial or complete isolation from plant material. Where it is desirable to isolate the expression product from some or all of plant cells or tissues that express it, any available purification techniques maybe employed. Those of ordinary skill in the art are familiar with a wide range of fractionation and separation procedures (see, for example, Scopes et al, Protein Purification Principles and Practice, 3 rd Ed, Janson et al, 1993, Protein Purification Principles High Resolution Methods, and Applications, Wiley-VCH, 1998, Springer-Verlag, NY, 1993, and Roe, Protein Purification Techniques, Oxford University Press, 2001, each of which is incorporated herein by reference). Those skilled in the art will appreciate that a method of obtaining desired recombinant fusion polypeptide(s) product(s) is by extraction. Plant material (e g, roots, leaves, etc) may be extracted to remove desired products from residual biomass, thereby increasing the concentration and purity of product Plants may be extracted in a buffered solution. For example, plant material may be transferred into an amount of ice-cold water at a ratio of one to one by weight that has been buffered with, e g, phosphate buffer. Protease inhibitors can be added as required. The plant material can be disrupted by vigorous blending or grinding while suspended in buffer solution and extracted biomass removed by filtration or centrifugation. The product earned in solution can be further purified by additional steps or converted to a dry powder by freeze-drying or precipitation. Extraction can be earned out by pressing. Plants or roots can be extracted by pressing in a press or by being crushed as they are passed through closely spaced rollers. Fluids derived from crushed plants or roots are collected and processed according to methods well known in the art. Extraction by pressing allows release of products in a more concentrated form. In some embodiments, polypeptides can be further purified by chromatographic methods including, but not limited to anion exchange chromatography (Q Column) or ultrafiltration. Polypeptides that contain His-tags can be purified using nickel-exchange chromatography according to standard methods. In some embodiments, produced proteins or polypeptides are not isolated from plant tissue but rather are provided in the context of live plants (e g, sprouted seedlings). In some embodiments, where the plant is edible, plant tissue containing expressed protein or polypeptide is provided directly for consumption. Thus, the present disclosure provides edible young plant biomass (e.g. edible sprouted seedlings) containing expressed protein or polypeptide.

Therefore, some advantageous embodiments pertain to methods of producing recombinant fusion proteins according to the present disclosure; the methods comprise the steps of:

a) providing a nucleic acid construct comprising a nucleic acid encoding the fusion protein, b) introducing the nucleic acid construct into a host cell, and c) maintaining the host cell under conditions permitting expression of the fusion protein, Furthermore, the disclosure pertains to a vaccine composition for immunizing human individuals against *Plasmodium falciparum* comprising as an active ingredient a mixture according to the present disclosure and a carrier in a physiologically acceptable medium.

A "vaccine" is a composition of matter comprising a formulation that, when administered to a subject, induces an immune response. Vaccines can comprise polynucleotide molecules, polypeptide molecules, and carbohydrate molecules, as well as derivatives and combinations of each, such as glycoproteins, lipoproteins, carbohydrate-protein conjugates, fusions between two or more polypeptides or polynucleotides, and the like. A vaccine may further comprise a diluent, an adjuvant, a carrier, or combinations thereof, as would be readily understood by those in the art. In one embodiment, the vaccine the composition comprises further an adjuvant.

An effective vaccine, wherein a fusion protein of the disclosure is recognized by the animal, will in an animal model be able to decrease parasite load in blood and target organs, prolong survival times and/or diminish weight loss after challenge with a malarial parasite, compared to non-vaccinated animals.

As mentioned above, the recombinant proteins in the vaccine composition may be coupled to a carbohydrate or a lipid moiety, e.g. a carrier, or a modified in other ways, e.g. being acetylated.

Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFN-gamma, IL-2, IL-12, monophosphoryl lipid A (MPL), Treholose Dimycolate (TDM), Trehalose Dibehenate and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20% solution of a perfluorocarbon (Fluosol-DA) used as a block substitute may also be employed. Other possibilities involve the use of immune modulating substances such as cytokines or synthetic IFN-gamma inducers such as poly I:C in combination with the above-mentioned adjuvants.

Another possibility for achieving adjuvant effect is to employ the technique described in Gosselin et al, 1992. In brief, a relevant antigen such as an antigen of the present invention can be conjugated to an antibody (or antigen binding antibody fragment) against the Fc-receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 micro g to 1000 micro g, such as in the range from about 1 micro g to 300 micro g, and especially in the range from about 10 micro g to 50 micro g. Suitable regimens for initial administration and booster shots are also variable but are typified by an initial administration followed by subsequent inoculations or other administrations. The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5 percent to 10 percent, preferably 1-2 percent. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95 percent of active ingredient, preferably 25-70%.

In many instances, it will be necessary to have multiple administrations of the vaccine. Especially, vaccines can be administered to prevent an infection with malaria and/or to treat established malarial infection. When administered to prevent an infection, the vaccine is given prophylactically, before definitive clinical signs or symptoms of an infection are present.

Due to genetic variation, different individuals may react with immune responses of varying strength to the same protein. Therefore, the vaccine according to the disclosure may comprise several different fusion proteins according to the present disclosure in order to increase the immune response. The vaccine may comprise two or more fusion proteins or immunogenic portions, where all of the proteins are as defined above, or some but not all of the peptides may be derived from *P. falciparum* or other parasites from the genus *Plasmodium*, in the latter example, the polypeptides not necessarily fulfilling the criteria set forth above for polypeptides may either act due to their own immunogenicity or merely act as adjuvants. The vaccine may comprise 1-20, such as 2-20 or even 3-20 different recombinant proteins or fusion proteins, such as 3-10 different proteins or fusion proteins.

In some embodiments, the fusion protein is adsorbed on or covalently bound to said carrier. In another embodiment, the carrier is a carrier protein.

The disclosure pertains also to antibody compositions comprising isolated antibodies or fragments thereof binding to the different recombinant proteins in the mixture according to the present disclosure. According to the present disclosure, the term "antibody" includes, but is not limited to recombinant antibodies, polyclonal antibodies, monoclonal antibodies, single chain antibodies, humanized antibodies, minibodies, diabodies, tribodies as well as antibody fragments, including antigen-binding portion of the antibodies according to the present disclosure, such as Fab', Fab, F(ab')$_2$ and single domain antibodies as mentioned above.

A further aspect of the present disclosure pertains to methods for treating and/or preventing malaria caused by *Plasmodium falciparum* (also called malignantor malaria, *falciparum* malaria or malaria *tropica*) in a patient, which comprises administering a therapeutically effective amount of a mixture of recombinant proteins according to the present disclosure.

The actual dosage amount of a mixture of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

The following methods and examples are offered for illustrative purposes only, and are not intended to limit the scope of the present disclosure in any way.

Methods and Examples

In the following example, materials and methods of the present disclosure are provided. It should be understood that these examples are for illustrative purpose only and are not to be construed as limiting this disclosure in any manner. All publications, patents, and patent applications cited herein are hereby incorporated by reference in their entirety for all purposes.

As example four different recombinant proteins named CCT (a fusion protein featuring PfCelTos (SEQ ID NO. 29). PfCSP_TSR (SEQ ID NO. 30) and PfTRAP_TSR (SEQ ID NO. 31)), gAMA1 (PfAMA1 (SEQ ID NO. 2) corresponding to *Plasmodium falciparum* strain 3D7), NME (a fusion protein featuring the 1$^{st}$ EGF of PfMsp1_19 (SEQ ID NO. 32), the EGF of PfMsp4 (SEQ ID NO. 33), the 1st and 2nd EGF of PfMsp8 (SEQ IDs NO. 34-35), and an N-terminal fragment of PfMsp3 (SEQ ID NO. 36), and 25-230C0 (a fusion protein featuring Pfs25 (SEQ ID NO. 44) and the C0 fragment of Pfs230 (SEQ ID NO. 45)) were produced in *N. benthamiana* plants. After purification the proteins were mixed and used for the immunization of rabbits. Antibody preparations from the obtained immune sera were characterized by different methods to demonstrate the immunogenicity and the inhibitory effect on *Plasmodium falciparum* parasites of different stages.

1. Cloning of Expression Constructs

The antigen fragment sequences listed in Table 1 were optimized for plant expression (GeneArt). The optimized sequences were inserted into the plant expression vector pTRAkc as NcoI and NotI fragments. For the generation of antigen fusion proteins the plant expression vector containing the antigen was linearized by NotI, 5' phosphate groups were removed by calf intestinal alkaline phosphatase (CIP) and the antigen domains were inserted as EagI fragments. All constructs carried a C-terminal His$_6$-tag for purification and a SEKDEL-tag for ER retrieval (Pelham, 1990). A detailed description of the pTRAkc plasmid is reported in Boes et al (Boes et al. 2011). All recombinant gene constructs were verified by sequencing and introduced into *Agrobacterium tumefaciens* strain GV3101 (pMP90RK) by electroporation. The recombinant *Agrobacterium tumefaciens* were cultivated as described previously (Sack et al. 2007; Vaquero et al. 1999). The optical density (OD) of the cultures was determined and expression strains were mixed with the *agrobacterium* strain carrying the silencing suppressor p19 (Plant Bioscience Limited, Norwich, England) at a 5:1 ratio to a final OD of 1.

Figure 2:
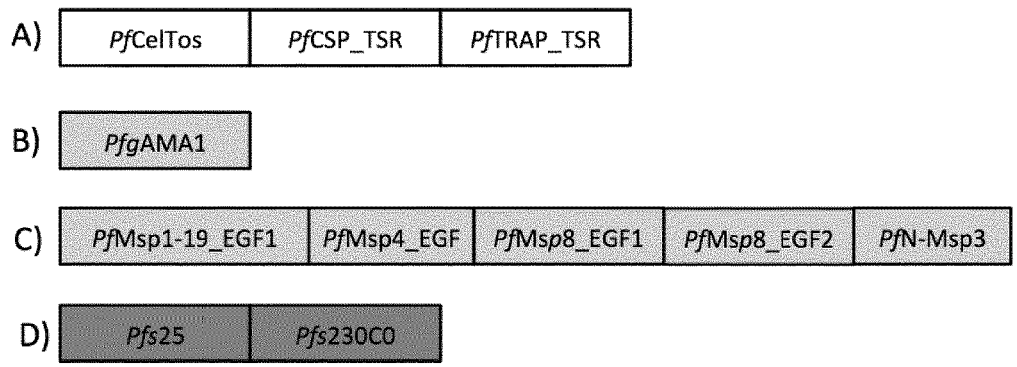
FIG. 2 is a schematic drawing of an embodiment of a mixture according to present disclosure comprising four exemplary fusion proteins (A: CCT-ERH/SEQ ID NO. 1, B: gAMA1-ERH/SEQ ID NO. 2, C: NME-ERH/SEQ ID NO. 3, D: F0-ERH/SEQ ID NO. 4).

FIG. 2 shows a schematic representation of 4 vaccine antigens used in this example:

PfCelTos: *Plasmodium falciparum* Cell traversal protein for ookinetes and sporozoites (CelTos); CSP_TSR: TSR-domain from Circum Sporozoite Protein (CSP) of *P. falciparum*; TRAP_TSR: TSR-domain from Thrombospondin-related adhesive proten (TRAP) of *P. falciparum*; PfgAMA1: *Plasmodium falciparum* Apical membrane antigen (AMA1) extracellular domains 1-3; PfMsp1-19_EGF1: EGF1 from the 19 kDa Fragment of MSP1 of *P. falciparum*; PfMsp4_EGF: EGF from MSP4 of *P. falciparum*; PfMsp8_EGF1: EGF1 from MSP8 *P. falciparum*; PfMsp8_EGF2: EGF2 from MSP8 of *P. falciparum*; Pfs25: Ookinete surface protein 25 of *P. falciparum*; Pfs230C0: C0-Fragment of gamete/gametocyte surface protein 230 of *P. falciparum*.

2. Transient Expression

For each construct the recombinant bacteria containing the respective expression cassette were separately injected manually into 6-8 week old *Nicotiana benthamiana* plants grown in rockwool. Infiltrated *Nicotiana benthamiana* plants were incubated for 5 days at 22° C. with a 16-h photoperiod. Plant leaf tissue was harvested for protein extraction and purification.

3. Protein Extraction

Leaf tissue was ground in liquid nitrogen using mortal and pestle and soluble proteins were extracted with 2 ml extraction buffer per gram of leaf material. For 25-230C0 we used PBS pH 7.4 the other 3 proteins were extracted using PBS pH 7.4 containing 10 mM Sodium disulfide. Insoluble material was removed by centrifugation (16000×g, 20 min, 4° C.) and the clear supernatant was used directly for purification. An additional heat precipitation step to efficiently remove plant host cell proteins was performed for the heat stable fusion proteins CCT and 25-230C0 (incubation of plant extract at 65° C. for 5 min). Afterwards insoluble material was removed by a series of centrifugation and filtration steps.

4. Protein Purification

His-tagged recombinant proteins of interest were purified by immobilized metal ion chromatography (IMAC). Briefly, the pH of the extract was adjusted to pH 8.0 and NaCl was added to a final concentration of 500 mM. The target protein was captured on Chelating sepharose charged with Nickel. After a washing step with PBS adjusted to pH 8.0 the target protein was eluted in a step gradient at 15 mM, 50 mM and 250 mM imidazole dissolved in PBS at pH 8.0.

5. Immunization of Rabbits

The purified proteins (SEQ ID No. 1-4) were mixed (hereinafter called PlasmoMix) in equal amounts to prepare a solution containing 220 µg/ml (total protein concentration 880 µg/ml) of each recombinant protein and sent to Biogenes (Berlin, Germany) for immunization of rabbits according to the "complete and Easy offer" and its corresponding immunization protocol.

6. Protein a Purification of Antibodies from Rabbit Sera

After immunization the antibodies from the rabbit antisera were purified by protein A chromatography. Briefly, serum samples were diluted 1:5 with PBS and filtered through 0.45 µm filter prior purification. The antibodies were bound onto Protein A resin (GE Healthcare) and unbound impurities were removed by a washing step with PBS. The bound antibodies were eluted with 100 mM glycine pH 3.0 and directly neutralized with 1M TRIS pH 8.0. A buffer exchange against RPMI1640 containing 25 mM HEPES and no L-Glutamine (E15-041, PAA) was performed using a HiPrep Desalting column and the antibodies were concentrated by centrifugal concentration devices (VivaSpin 15R 30.000 MWCO, Sartoruis) to a concentration greater than 12 mg/ml and sterile filtered. Antibodies were stored at 4° C.

7. SDS-PAGE and Immunoblot Analysis

Proteins were separated on commercial 4-12% (w/v) gradient gels (Invitrogen) under reducing and/or non-reducing conditions and stained with Coomassie R-250 following the Fairbanks protocol (Wong et al. 2000). Separated proteins were blotted onto a nitrocellulose membrane (Whatman, Dassel, Germany) and blocked with 5% (w/v) skimmed milk dissolved in PBS. Proteins were probed with the Rabbit anti-His6-tag as primary antibody at a 1:5000 dilution. Secondary antibody was Goat anti-Rabbit H+L alkaline phosphatase labeled. Bands were visualized with NBT/BCIP (1 mg·ml-1 in substrate buffer: 150 mM NaCl, 2 mM MgCl2, 50 mM Tris-HCl, pH 9.6). Between the incubation steps the membranes were washed three times with PBS supplemented with 0.05% (v/v) Tween-20.

Figure 3:
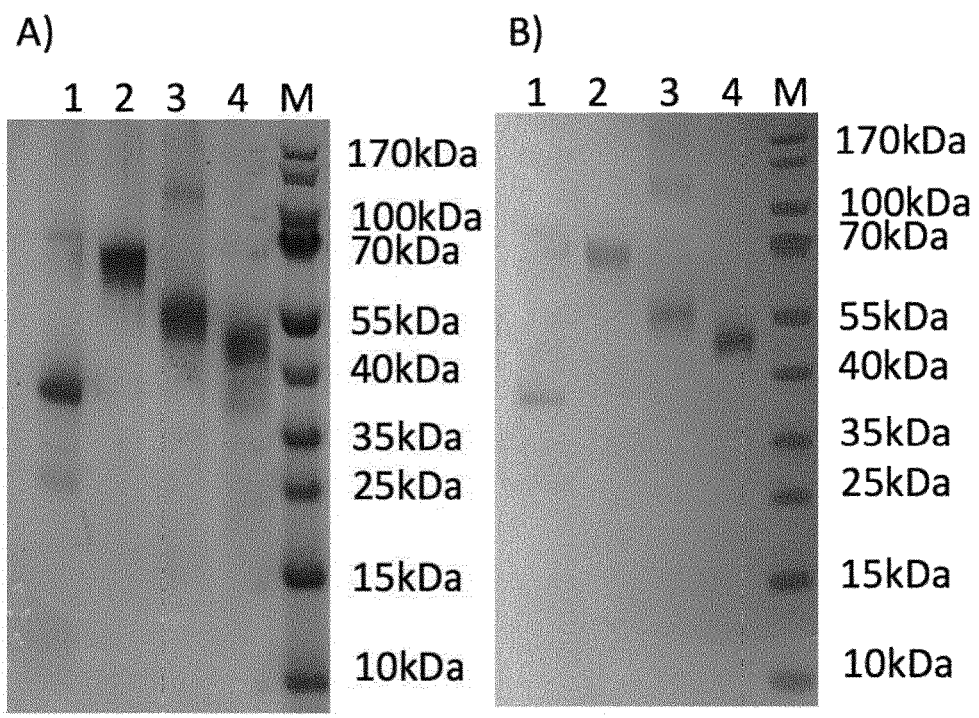
FIG. 3 shows a SDS-PAGE and Western Blot analysis of 4 (1: CCT-ERH/SEQ ID NO. 1, 2: gAMA1-ERH/SEQ ID NO. 2, 3: NME-ERH/SEQ ID NO. 3, 4: F0-ERH/SEQ ID NO. 4) purified exemplary vaccine proteins.

FIG. 3 SDS-PAGE and Western Blot analysis of the different Ni-NTA purified recombinant proteins according to the present example. Proteins were separated under reducing conditions. FIG. 3A shows a Coomassie stained gel; FIG. 3B is an Immunoblot analysis. Recombinant proteins were detected with Rabbit anti-His antibodies followed by goat anti-Rabbit H+L alkaline phosphatase labeled antibodies. Molecular weight standard is indicated at the left site.

The abbreviations in FIG. 3 are:
1: CCT-ERH (SEQ ID NO. 1)
2: gAMA1-ERH (SEQ ID NO.2)
3: NME-ERH (SEQ ID NO. 3)
4: Pfs25_230C0-ERH (SEQ ID NO.4)
M: Molecular weight marker

8. ELISA

The specific antibody (IgG) titer in the serum against the protein used for immunization as well as the reactivity against all subunits/domains was measured by ELISA using high-binding 96 well plates (Greiner bio-one, Frickenhausen, Germany) coated with recombinant proteins s at a concentration of 1 μg/ml. After 1 h of incubation at room temperature. The wells were blocked with 5% (w/v) skimmed milk in PBS and incubated again for 1 h at room temperature. A serial dilution of the serum as well as the pre-immune serum was applied to the 96 well plate and incubated for 1 h at room temperature. The antigen-bound antibodies were probed with HRPO-labeled Goat anti-Rabbit IgG Fc and detected with ABTS substrate at 405 nm after 30 min. Between each step, the plates were washed three times with PBS supplemented with 0.05% (v/v) Tween-20. The specific IgG titer was defined as the dilution which results in an OD 405 nm twice the value of the pre-immune serum.

TABLE 3

Rabbit antibody titers raised against a mixture of four different plant produced antigens (SEQ IDs No. 1-4) listed in Table 1

| Pathogen stages covered by recombinant fusion protein | Assay | Minimal balanced antibody titer against every antigen fragment included in vaccine candidate (SEQ IDs NO. 1-4) |
|---|---|---|
| pre-erythrocytic stage asexual/blood stage sexual stage | ELISA | $1 \times 10^{-4}$ |

9. Immunofluorescence-Assay (IFA)

Figure 4:
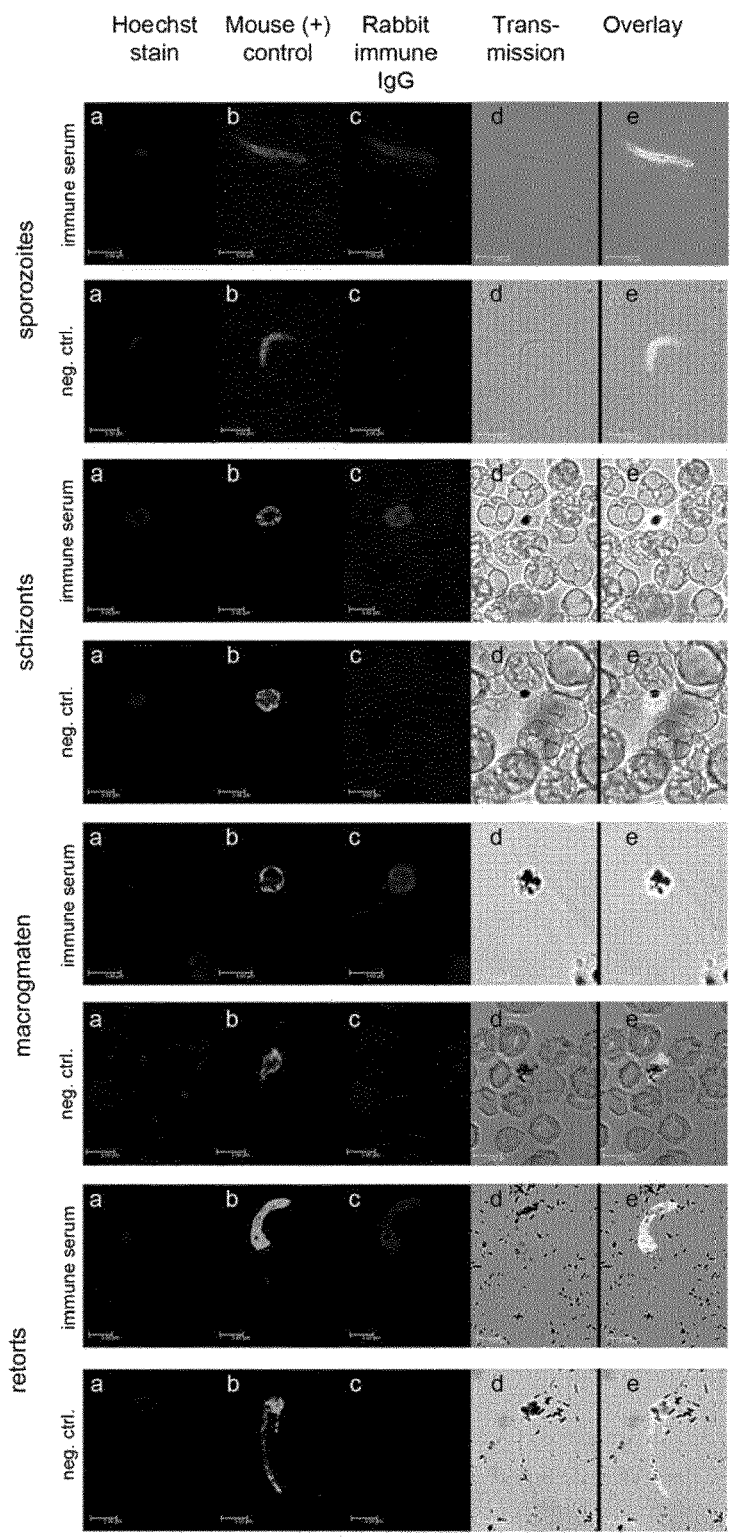
FIG. 4 shows images of Immunofluorescent staining of *Plasmodium falciparum* stages using antibodies derived by immunization with a mixture of the 4 (CCT-ERH: SEQ ID 1, gAMA1-ERH: SEQ ID 2, NME-ERH: SEQ ID 3, F0-ERH: SEQ ID 4) example vaccine proteins.
Figure 5:
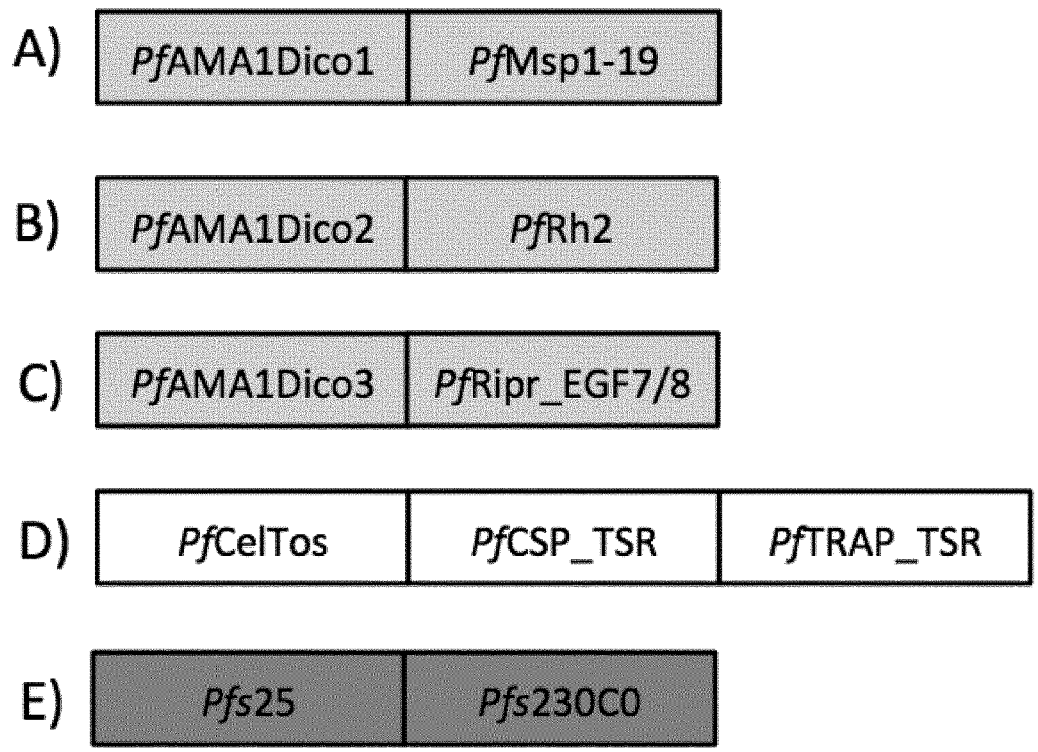
FIG. 5 is a schematic drawing of another embodiment of a mixture according to the present disclosure comprising five exemplary fusion proteins.

To visualize different stages of the *P. falciparum* parasite indirect IFA was performed in the main as described previously (Pradel et al, 2004). Cultivation of asexual stages and gametocytes of *P. falciparum* strain NF54 were performed as described previously (Ifediba and Vanderberg, 1981). Parasite preparations were air dried on 8-well diagnostic slides (Thermo scientific) and fixed with −80° C. methanol for 10 min. To block nonspecific binding and to permeabilize membranes, fixed cells were incubated in 0.5% BSA, 0.01% saponin in PBS for 30 min at RT and subsequently in 0.5% BSA, 0.01% saponin, 1% neutral goat serum in PBS for 30 min at RT. Samples were incubated with the purified antibodies directed against PlasmoMix, diluted in blocking solution without goat serum at 37° C. for 1 h. Purified antibodies were used at a final concentration of 15 μg/ml. For counterstaining of the different *P. falciparum* life cycle stages, mouse antisera directed against single *P. falciparum* antigen fragments from Pf_CSP_TSR (counterstaining of sporozoites), MSP1-19 (counterstaining of schizonts) or Pfs25 (counterstaining of macrogametes and zygotes) were generated by Fraunhofer IME and used in final concentrations of 1/200. Primary antibodies were visualized by incubation of cells with fluorescence-conjugated Alexa Fluor 488 goat-anti-mouse or Alexa Fluor 594 goat-anti-rabbit antibodies (Invitrogen) at a dilution of 1/1000 in blocking solution without goat serum. If no labeling of parasites with Alexa Fluor 594 coupled antibodies occurred, cells were counterstained with 0.05% Evans Blue in PBS. To highlight nuclei, samples were incubated with Hoechst in 0.01% saponin in PBS. Finally, cells were mounted with anti-fading solution AF2 (Citifluor Ltd.) and sealed with nail varnish. Examination of labeled cells and scanning of images was performed using a Leica sp5 confocal microscope. Exemplary immunofluorescence assays of different *Plasmodium falciparum* stages with purified rabbit antibodies raised against PlasmoMix according to the present disclosure are illustrated in FIG. 4. In each section of the Figure a Hoechst nuclear staining is shown on the left, a positive control staining in the second left (murine control pAb, detection with anti-mouse pAb labeled with Alexa488) and a staining with purified rabbit pAb raised against PlasmoMix on the third left (detection with anti-rabbit pAb labeled with Alexa594), neutral rabbit pAb control on the forth left and transmission followed by overlay images on the right.

10. Inhibition of Sporozoite Binding/Invasion (ISI)

To assess the ability of antisera directed against *P. falciparum* antigens to block the attachment and invasion of *P. falciparum* NF54 sporozoites to human liver cells, inhibition of sporozoite binding/invasion assays were performed following the protocols presented in Rathore et al. (2003) and McCormick et al. (2008). HepG2 cells were diluted in RPMI medium containing 10% FBS to a concentration of 60000/ml. 400 μl of this suspension were added to each well of E-C-L cell attachment matrix (Millipore) coated 8-well Lab-Tek permanox chamber slides (Thermo Scientific). Cells were incubated for 48 h at 37° C. and 5% CO2 to form a closed monolayer. On day 2 after seeding of HepG2 cells, *Plasmodium falciparum* NF54 sporozoites were isolated from *Anopheles stephensi* mosquitoes 19-21 days after an artificial infectious blood meal and collected in 0.0001% FBS in PBS. Sporozoites where counted using a neubauer hemocytometer and 20000 sporozoites in 300 μl RPMI/10% FBS where added to each well of HepG2 cells, washed 3 times with RPMI before. Purified polyclonal antibodies from rabbit antisera directed against PlasmoMix dissolved in RPMI where used at concentrations of 600 μg/ml and cells where subsequently incubated for 3 hours at 37° C. and 5% CO2. To distinguish between extracellular and intracellular sporozoites a double labeling was performed following the protocols described previously (Hügel et al. 1996, Pradel and Frevert 2001) with some modifications. To label extracellular sporozoites, HepG2 cells were washed thrice with RPMI medium. Incubation with rabbit-anti-CSP (MRA-24, ATCC) diluted 1/200 in RPMI for 1 h at 37° C. was further followed by three washing steps with RPMI and incubation with alexa 488 conjugated goat-anti-rabbit antibodies (Invitrogen) diluted 1/1000 in RPMI at 37° C. for 1 h. Cells were washed thrice with PBS, air dried and fixed with methanol for 10 min at −80° C. Blocking and permeabilization of cell membranes was performed over night at 4° C. by incubation with 0.5% BSA, 0.01% saponin in PBS. To subsequently label all sporozoites, incubation with rabbit-anti-CSP (MRA-24, ATCC) diluted 1/200 in blocking solution for 1 h at 37° C. was followed by three washing steps with blocking solution and incubation with alexa 594 conjugated goat-anti-rabbit antibodies (Invitrogen) diluted 1/1000 in blocking solution at 37° C. for 1 h. To highlight nuclei, samples were incubated with Hoechst in PBS. Finally, cells were mounted with anti-fading solution AF2 (Citifluor Ltd.) and sealed with nail varnish. Counting of extracellular (red and green fluorescence) and intracellular (only red fluorescence) was performed using a Zeiss LSM510 confocal microscope. The ISI results of purified rabbit antibodies raised against PlasmoMix according to the present disclosure are listed below in Table 4.

11. Growth Inhibition Assay (GIA)

The growth inhibitory potential against *plasmodium* parasites was performed using a standardized protocol. The *P. falciparum* parasite strain 3D7A (provided by MR4) was maintained in culture at parasitemias below 5% at a haematocrit of 4% in RPMI medium supplemented with 10% Albumax II (Invitrogen), 25 mM Hepes, 12 µg/ml gentamicin and 100 µM hypoxanthine at 37° C. and 5% CO2, 5% O2 and 90% N2. The cultures were maintained in a daily routine and parasitemia estimated by Giemsa staining. The erythrocyte used in the assay were mixed from 15 malaria-naïve blood donors and not older than 3 weeks. The erythrocytes were stored in SAG-Mannitol at 4° C. The parasites were synchronized by 10% Sorbitol treatment within a time window of 1-16 hours post invasion. For the assay, only highly synchronous cultures 36 to 40 hours post invasion were used.

Parasites and fresh RBCs and antibodies were mixed in a 96-well plate appropriately in order to have a final parasitemia of 0.1% and a final haematocrit of 2%. For the background control, only RBC without parasites were kept in culture under the same conditions as the parasites. A growth control for the monitoring the parasite growth was performed by culturing the *Plasmodium falciparum* parasite without additions. All samples were measured in triplicates. As negative control, malaria-naïve rabbit and human plasma were derived purified antibodies were tested. For positive control of complete invasion inhibition, EDTA (4 mM final concentration) and BG98 rabbit anti-AMA-1 polyclonal antibodies were used. The plates were incubated at 37° C., 95% humidity, 5% CO2, 5% O2, and 90% N2 for 40 to 44 hours. At harvest, wells were washed once with cold PBS and frozen down. Parasite growth was estimated by a Malstat™ assay32. Absorbance was measured after 30 minutes at a wavelength of 655 nm using a spectrophotometer. Inhibitory capacity was estimated by the following formula:

% inhibition=100%−((*A*655 IgG sample-*A*655 RBC control))/((*A*655 Schizont control-*A*655 RBC control))*100%

As mentioned above, the growth inhibition assay is a standard in vitro assay to evaluate the inhibitory potential of antibodies. The assay simulates the asexual stage/blood stage. The GIA results of purified rabbit antibodies raised against PlasmoMix listed in Table 4.

12. Transmission Blocking Assay (TBA)

To assess the ability of antisera directed against *P. falciparum* antigens to block the transmission of *P. falciparum* NF54 from the human to the mosquito, membrane feeding assays were performed (Bishop and Gilchrist, 1946). Briefly, mature stage V gametocytes were purified from cultures showing substantial exflagellation by percoll density gradient centrifugation (Kariuki et al, 1998) and mixed with an equal amount of fresh A+-erythrocytes. Cells were then mixed with an equal amount of active human A+-serum supplemented with the respective antiserum to test. Unpurified test sera where used up to a concentration of 1/10, purified test sera up to a concentration of 1 mg/ml. Samples were directly fed to 3-5 days old *A. stephensi* mosquitoes through a thin layer of parafilm stretched across the bottom of a glass feeder heated to 38° C. Mosquitoes used for infections were previously fed on a solution of 5% saccharose, 0.05% para-aminobenzoic acid, 40 µg/ml gentamicin soaked on cotton wool pads. Gentamicin was part of the diet to enhance overall infection rates (Beier M S et al, 1994). The mosquitoes were allowed to feed for 20 minutes on the blood meal and were afterwards kept in a secured insectary at 80% humidity and 26° C. On the following days, feeding was done using the above-mentioned solution. To measure the infectivity of the different blood meals for each sample 20 midguts of blood fed mosquitoes were dissected 9-12 days after the infection and stained with 0.2% mercurochrome in PBS to facilitate counting of oocysts. Counting of oocysts was performed at a light microscope using a magnification of 100 fold. The TBA results of purified rabbit antibodies raised against Plasmomix listed in Table 4.

TABLE 4

Exemplary inhibition results of purified rabbit antibodies raised against the components of Plasmomix according to the present disclosure.

| Pathogen stage | Inhibition assay | Inhibition [%] |
| --- | --- | --- |
| pre-erythrocytic stage (CCT-ERH: SEQ ID NO. 1) | inhibition of sporozoite binding/invasion | >30 |
| asexual/blood stage (gAMA1-ERH: SEQ ID NO. 2, NME-ERH: SEQ ID NO. 3) | growth inhibition assay | >80 |
| sexual stage (F0-ERH: SEQ ID NO. 4) | transmission blocking assay | 80-100 |

The results demonstrate the feasibility to produce exemplary antigens according to the present disclosure based on *Plasmodium falciparum* surface proteins or protein domains of three *Plasmodium* life cycle stages. The production was accomplished in *Nicotiana benthamiana* plants. After purification the mixture of the four recombinant proteins elicited a balanced antibody response in animals with a titer greater than $1\times10^{-4}$. Immune fluorescence assays confirmed that the induced antibodies specifically bind to the native *Plasmodium* antigens. Further, functional assays demonstrated specific parasite inhibition in every corresponding *Plasmodium* life cycle stage in a range from 30-100%.

Further examples of vaccine mixtures according to the present disclosure (M1 and M2) were produced and tested.

13. Cloning of Expression Constructs
Already described above.
14. Transient Expression
Already described above.
15. Protein Extraction
Leaf tissue was ground in liquid nitrogen using mortal and pestle and soluble proteins were extracted with 3-7 ml extraction buffer (PBS containing 10 mM Sodium disulfide and 500 mM NaCl, pH 7.4) per gram of leaf material. Tobacco crude extracts were adjusted to pH 8.0 by adding 10% (v/v) of 1 M TRIS pH 8.0. In case of PfCelTOS-PfCSP_TSR-PfTRAP_TSR-PfRh5a (SEQ-ID 33) and Pfs25-Pfs230_C0_PfRh5b (SEQ-ID 36) a heat precipitation was performed to remove plant host cell proteins. Extracts were incubated in a thermomixer (Eppendorf) until the temperature in the extract reached 65° C. Insoluble material was removed by centrifugation (16000×g, 20 min, 4° C.) and the clear supernatant was used directly for purification.

16. Protein Purification

CCT-9AD4 and F0-Q5A were used directly without an additional purification step. The AMA1_DiCo variants (PfAMA1-DiCo1-3 and PfAMA1-DiCo1-Msp1_19FUP, PfAMA1-DiCo2-Rh2 and PfAMA1-DiCo3-RIPR7/8) were purified by immunoaffinity chromatography. Therefore the chimeric monoclonal antibody 4G2 (PfAMA1-specific) was covalently coupled to NHS-activated sepharose (GE healthcare) according to the manufacturer's instruction. Unbound proteins were washed away with PBS and bound proteins were eluted with 100 mM glycine pH 3.0 and immediately neutralized with 10% (v/v) 1 M TRIS pH 8.0.

17. SDS-PAGE and Immunoblot Analysis

Proteins were separated on commercial 4-12% (w/v) gradient gels (Invitrogen) under non-reducing conditions and stained with Coomassie R-250 following the Fairbanks protocol (Wong et al. 2000). Separated proteins were blotted onto a nitrocellulose membrane (Whatman, Dassel, Germany) and blocked with 5% (w/v) skimmed milk dissolved in PBS. PfAMA1 containing proteins were probed with chimeric monoclonal antibody 4G2 as primary antibody at a 1:5000 dilution followed by an alkaline phosphatase labeled goat anti-human antiserum. The protein PfCelTOS-PfCSP_TSR-PfTRAP_TSR-PfRh5a was probed with a PfCSP_TSR-specific monoclonal antibody followed by an alkaline phosphatase labeled goat anti-murine antiserum and the protein Pfs25-Pfs230_C0_PfRh5b was probed using the chimeric monoclonal antibody 4B7 (Pfs25-specific) followed the same secondary antibody used for the detection of the PfAMA1 proteins. Bands were visualized with NBT/BCIP (1 mg·ml-1 in substrate buffer: 150 mM NaCl, 2 mM MgCl2, 50 mM Tris-HCl, pH 9.6). Between the incubation steps the membranes were washed three times with PBS supplemented with 0.05% (v/v) Tween-20.

FIG. 6: SDS-PAGE and Western Blot analysis of the different recombinant proteins used to prepare vaccine mixture M1 and M2 according to the present example. Proteins were separated under non-reducing conditions. FIG. 6A shows a Coomassie stained gel of immunoaffinity chromatography purified PfAMA1-containing recombinant proteins and heat precipitated tobacco crude extract containing either PfCelTOS-PfCSP_TSR-PfTRAP_TSR-PfRh5a (indicated by solid arrow head) or Pfs25-Pfs230_C0-PfRh5b (indicated by open arrow head); FIG. 6B is an immunoblot analysis of PfAMA1-containing proteins purified by immunoaffinity chromatography; FIG. 6C is an immunoblot analysis of heat precipitated tobacco crude extract containing PfCelTOS-PfCSP_TSR-PfTRAP_TSR-PfRh5a; FIG. 6D is an immunoblot analysis of heat precipitated tobacco crude extract containing Pfs25-Pfs230_C0-PfRh5b. The antibodies used for the detection of the recombinant proteins are listed in the SDS-PAGE and immunoblot analysis section. M: Marker PageRuler (Fermentas); 1: PfAMA1-DiCo1 (SEQ-ID NO. 11); 2: PfAMA1-DiCo2 (SEQ-ID NO. 12); 3: PfAMA1-DiCo3 (SEQ-ID NO. 13); 4: Mixture of 1-3; 5: PfAMA1-DiCo1-Msp1_19FUP (SEQ-ID NO. 14); 6: PfAMA1-DiCo2-Rh2 (SEQ-ID NO. 15); 7: PfAMA1-DiCo3-RIPR7/8 (SEQ-ID NO. 16); 8: Mixture of 5-7; 9: heat precipitated wild type tobacco crude extract; 10: heat precipitated tobacco crude extract containing PfCelTOS-PfCSP_TSR-PfTRAP_TSR-PfRh5a (SEQ-ID NO. 9); 11: heat precipitated tobacco crude extract containing Pfs25-Pfs230_C0-PfRh5b (SEQ-ID NO. 28).

18. Rabbit Immunization

For immunization of rabbits two vaccine mixtures M1 and M2 (vaccine cocktails) were prepared and the mixtures are described below.

TABLE 1

Composition of vaccine mixture M1 and M2

| Vaccine mixture 1 (M1) | | Vaccine mixture 2 (M2) | |
|---|---|---|---|
| Component | SEQ-ID NO. | Component | SEQ-ID NO. |
| PfCelTOS-PfCSP_TSR-PfTRAP_TSR-PfRh5a | 9 | PfCelTOS-PfCSP_TSR-PfTRAP_TSR-PfRh5a | 9 |
| PfAMA1-DiCo1 | 11 | PfAMA1-DiCo1-Msp1_19FUP | 14 |
| PfAMA1-DiCo2 | 12 | PfAMA1-DiCo2-Rh2 | 15 |
| PfAMA1-DiCo3 | 13 | PfAMA1-DiCo3-RIPR7/8 | 16 |
| Pfs25-Pfs230_C0-PfRh5b | 28 | Pfs25-Pfs230_C0-PfRh5b | 28 |

Proteins were mixed in equal volumes and the resulting vaccine mixtures M1 and M2 were used for rabbit immunizations (Biogenes, Berlin, Germany).

19. Titer Determination

The specific antibody (IgG) titer in the serum against the vaccine mixtures (M1 and M2) used for immunization was measured by ELISA using high-binding 96 well plates coated with the respective vaccine mixture (10 µg/ml in 50 mM carbonate buffer pH 9.5). After the coating step (room temperature over night) the wells were blocked with 1% (v/v) fetal calf serum in TBS for 30 min at room temperature. A serial dilution of the serum as well as the pre-immune serum was applied to the 96 well plate and incubated for 1 h at room temperature. The antigen-bound antibodies were probed with POD-labeled anti-rabbit IgG antibodies (Sigma A4914) for 1 h at room temperature and detected with TMB One substrate (Kem-En-Tac Diagnostic). The reaction was stopped after 15 min by adding 500 mM sulfuric acid and the absorption of the yellow solution was measured at 450 nm (reference wavelength 630 nm). Between each step, the plates were washed three times with TBS supplemented with 0.05% (v/v) Triton X-100. The specific IgG titer was defined as the dilution that results in an OD 450 nm twice the value of the pre-immune serum.

TABLE 6

Rabbit antibody titers raised against vaccine mixture M1 and M2

| Vaccine mixture 1 (M1) | | Vaccine mixture 2 (M2) | |
|---|---|---|---|
| Titer | $1.0\text{-}1.5 \times 10^{-5}$ | Titer | $2.0 \times 10^{-5}$ |

REFERENCES

The contents of all cited references, including literature references, issued patents, and published patent applications, as cited throughout this application are hereby expressly incorporated by reference.

Altschul, S. F., Gish, W., Miller, W., Myers, E. W. & Lipman, D. J. Basic local alignment search tool. Journal of molecular biology 215, 403-10 (1990).

Ausubel, F. M. et al. Current protocols in molecular biology, edited by M. Ausubel, R. Brent, R. E. Kingston, D. D. Moore, J. G. Seidman, J. A. Smith, and K. Struhl. Volumes 1 and 2. John Wiley & Sons, Inc., Media, Pa., 1988, 165.00. Molecular Reproduction and Development 1, 146-146 (1989).

Beier M S, Pumpuni C B, Beier J C, Davis J R. 1994. Effects of para-aminobenzoic acid, insulin, and gentamicin on *Plasmodium falciparum* development in anopheline mosquitoes (Diptera: Culicidae). J. Med. Entomol. 31(4): 561-565

Bergmann-Leitner E S, Mease R M, De La Vega P, Savranskaya T, Polhemus M, Ockenhouse C, Angov E. 2010. Immunization with pre-erythrocytic antigen CelTOS from *Plasmodium falciparum* elicits cross-species protection against heterologous challenge with *Plasmodium berghei*. PLoS One 5(8):e12294.

Bishop A and Gilchrist B M. 1946. Experiments upon the feeding of *Aedes aegypti* through animal membranes with a view to applying the method to the chemotherapy of malaria. Parasitology. 37: 85-100

Black C G, Wang L, Wu T, Coppel R L. 2003. Apical location of a novel EGF-like domain-containing protein of *Plasmodium falciparum*. Mol Biochem Parasitol 127 (1):59-68.

Black C G, Wu T, Wang L, Hibbs A R, Coppel R L. 2001. Merozoite surface protein 8 of *Plasmodium falciparum* contains two epidermal growth factor-like domains. Mol Biochem Parasitol 114(2):217-26.

Black, C. G., Wang, L., Wu, T. & Coppel, R. L. Apical location of a novel EGF-like domain-containing protein of *Plasmodium falciparum*. Molecular and biochemical parasitology 127, 59-68 (2003).

Black C G, Wu T, Wang L, Hibbs A R, Coppel R L. Merozoite surface protein 8 of *Plasmodium falciparum* contains two epidermal growth factor-like domains. Mol Biochem Parasitol 2001; 114:217-26.

Blackman M J, Ling I T, Nicholls S C, Holder A A. 1991. Proteolytic processing of the *Plasmodium falciparum* merozoite surface protein-1 produces a membrane-bound fragment containing two epidermal growth factor-like domains. Mol Biochem Parasitol 49(1):29-33.

Boes A, Spiegel H, Delbruck H, Fischer R, Schillberg S, Sack M. 2011. Affinity purification of a framework 1 engineered mouse/human chimeric IgA2 antibody from tobacco. Biotechnol Bioeng 108(12):2804-14.

Brochet, X., Lefranc, M.-P. & Giudicelli, V. IMGT/V-QUEST: the highly customized and integrated system for IG and TR standardized V-J and V-D-J sequence analysis. Nucleic acids research 36, W503-8 (2008).

Chen L, Lopaticki S, Riglar D T, Dekiwadia C, Uboldi A D, Tham W H, O'Neill M T, Richard D, Baum J, Ralph S A and others. 2011. An EGF-like protein forms a complex with PfRh5 and is required for invasion of human erythrocytes by *Plasmodium falciparum*. PLoS Pathog 7(9): e1002199.

Dayhoff, M. O. Atlas of Protein Sequence and Structure (Vol 5, Supplement 3). 353-358 (Natl Biomedical Research: 1979).

Epping R J, Goldstone S D, Ingram L T et al. An epitope recognized by inhibitory monoclonal antibodies that react with a 51 kilodalton merozoite surface antigen in *Plasmodium falciparum*. Exp Parasitol 1988; 81:90-6.

Garcia-Basteiro A L, Bassat Q and Alonso P L. 2012. Approaching the Target: the Path Towards an Effective Malaria Vaccine. Mediterr J Hematol Infect Dis. 4(1): e2012015

Geysen, H. M., Meloen, R. H. & Barteling, S. J. Use of peptide synthesis to probe viral antigens for epitopes to a resolution of a single amino acid. Proceedings of the National Academy of Sciences of the United States of America 81, 3998-4002 (1984).

Gosselin, E. J., K. Wardwell, D. R. Gosselin, N. Alter, J. L. Fisher, and P. M. Guyre. 1992. Enhanced antigen presentation using human Fc gamma receptor (monocyte/macrophage)-specific immunogens. J. Immunol. 149:3477-3481.

Hügel F U, Pradel G and Frevert U. 1996. Release of malaria circumsporozoite protein into the host cell cytoplasm and interaction with ribosomes. Mol Biochem Parasitol. 81(2): 151-170

Ifediba T, Vanderberg J P. 1981. Complete in vitro maturation of *Plasmodium falciparum* gametocytes. Nature. 294 (5839): 364-366

Kariuki M M, Kiaira J K, Mulaa F K, Mwangi J K, Wasunna M K and Martin S K. 1998. *Plasmodium falciparum*: Purification of the various gametocyte developmental stages from in vitro-cultivated parasites. Am. J. Trop. Med. Hyg. 59(4): 505-508

Kaslow D C, Quakyi I A, Syin C, Raum M G, Keister D B, Coligan J E, McCutchan T F, Miller L H. 1988. A vaccine candidate from the sexual stage of human malaria that contains EGF-like domains. Nature 333(6168):74-6.

Kusi, K. A. et al. Immunization with different PfAMA1 alleles in sequence induces clonal imprint humoral responses that are similar to responses induced by the same alleles as a vaccine cocktail in rabbits. Malaria journal 10, 40 (2011).

Livingstone, C. D. & Barton, G. J. Protein sequence alignments: a strategy for the hierarchical analysis of residue conservation. Computer applications in the biosciences: CABIOS 9, 745-56 (1993).

Mahajan, B., J. A. Berzofsky, et al. (2010). "Multiple antigen peptide vaccines against *Plasmodium falciparum* malaria." Infect Immun 78(11): 4613-4624.

Makler, M. T. et al. Parasite lactate dehydrogenase as an assay for *Plasmodium falciparum* drug sensitivity. The American journal of tropical medicine and hygiene 48, 739-41 (1993).

Marshall V M, Silva A, Foley M, Cranmer S, Wang L, McColl D J, Kemp D J, Coppel R L. 1997. A second merozoite surface protein (MSP-4) of *Plasmodium falciparum* that contains an epidermal growth factor-like domain. Infect Immun 65(11):4460-7.

Marshall V M, Tieqiao W, Coppel R L. 1998. Close linkage of three merozoite surface protein genes on chromosome 2 of *Plasmodium falciparum*. Mol Biochem Parasitol 94(1):13-25.

Pelham H R. 1990. The retention signal for soluble proteins of the endoplasmic reticulum. Trends Biochem Sci 15(12):483-6.

Marshall V M, Silva A, Foley M et al. A second merozoite surface protein (MSP-4) of *Plasmodium falciparum* that contains an epidermal growth factor-like domain. Infect Immun 1997; 65:4460-7.

McCormick C J, Hollingdale M R and Taylor R. 2008. Sporozoite invasion assay. In: Methods in Malaria Research 5th Edition. K. Moll, I. Ljungström, H. Perlmann, A. Scherf and M. Wahlgren (Eds.). MR4/ATCC Manassas, Va. BioMalPar Paris, France. pp 138-140

Pachebat J A, Ling I T, Grainger M et al. The 22 kDa component of the protein complex on the surface of *Plasmodium falciparum* merozoites is derived from a larger precursor, merozoite surface protein 7. Mol Biochem Parasitol 2001; 117: 83-9.

Patarroyo M E, Amador R, Clavijo P, Moreno A, Guzman F, Romero P, et al. A synthetic vaccine protects humans against challenge with asexual blood stages of *Plasmodium falciparum* malaria Nature. 1988; 332(6160):158-61

Pradel G, Hayton K, Aravind L, Iyer L M, Abrahamsen M S, Bonawitz A, Mejia C, Templeton T J. 2004. A multi-domain adhesion protein family expressed in *Plasmodium falciparum* is essential for transmission to the mosquito. J. Exp. Med. 199(11): 1533-1544

Pradel G and Frevert U. 2001. Malaria sporozoites actively enter and pass through rat Kupffer cells prior to hepatocyte invasion. Hepatology. 33(5): 1154-11654. Chothia, C. et al. Conformations of immunoglobulin hypervariable regions. *Nature* 342, 877-83

Plassmeyer M L, Reiter K, Shimp R L, Jr., Kotova S, Smith P D, Hurt D E, House B, Zou X, Zhang Y, Hickman M and others. 2009. Structure of the *Plasmodium falciparum* circumsporozoite protein, a leading malaria vaccine candidate. J Biol Chem 284(39):26951-63.

Rathore D, Hrstka S C, Sacci J B Jr, De la Vega P, Linhardt R J, Kumar S and McCutchan T F. 2003. Molecular mechanism of host specificity in *Plasmodium falciparum* infection: role of circumsporozoite protein. J Biol Chem. 278(42): 40905-40910

Richards, J. S. and J. G. Beeson (2009). "The future for blood-stage vaccines against malaria" Immunol Cell Biol 87(5): 377-390.

Roestenberg, M. et al. Safety and immunogenicity of a recombinant *Plasmodium falciparum* AMA1 malaria vaccine adjuvanted with Alhydrogel, Montanide ISA 720 or AS02. PloS one 3, e3960 (2008).

Sack M, Paetz A, Kunert R, Bomble M, Hesse F, Stiegler G, Fischer R, Katinger H, Stoeger E, Rademacher T. 2007. Functional analysis of the broadly neutralizing human anti-HIV-1 antibody 2F5 produced in transgenic BY-2 suspension cultures. FASEB J 21(8):1655-64.

Sambrook, J., Fritsch, E. F. & Maniatis, T. Molecular Cloning: A Laboratory Manual, Volume 1 to 3, 2nd edition. Sambrook J E F Fritsch and T Maniatis Molecular Cloning A Laboratory Manual Second Edition Vols 1 2 and 3 Cold Spring Harbor Laboratory Press Cold Spring Harbor N. Y. USA Illus Paper (1989).

Schwartz, L, G. V. Brown, et al. (2012). "A review of malaria vaccine clinical projects based on the WHO rainbow table." Malar J 11: 11.

Smith, T. F. & Waterman, M. S. Comparison of biosequences. Advances in Applied Mathematics 2, 482-489 (1981).

Srinivasan P, Beatty W L, Diouf A, Herrera R, Ambroggio X, Moch J K, Tyler J S, Narum D L, Pierce S K, Boothroyd J C and others. 2011. Binding of *Plasmodium* merozoite proteins RON2 and AMA1 triggers commitment to invasion. Proc Natl Acad Sci USA 108(32): 13275-80.

Tachibana M, Wu Y, Iriko H, Muratova O, MacDonald N J, Sattabongkot J, Takeo S, Otsuki H, Torii M, Tsuboi T. 2011. N-terminal prodomain of Pfs230 synthesized using a cell-free system is sufficient to induce complement-dependent malaria transmission-blocking activity. Clin Vacc Tan K I, Duquette M., Liu J., Dong Y., Zhang R., Joachimiak A., Lawler J., Wang J. 2002. Crystal structure of the TSP-1 type 1 repeats: A novel layered fold and its biological implication. J. Cell Biol. 159: 373-382.

Taylor, W. R. The classification of amino acid conservation. Journal of theoretical biology 119, 205-18 (1986).

Tossavainen H, Pihlajamaa T, Huttunen T K, Raulo E, Rauvala H, Permi P, Kilpelainen I. 2006. The layered fold of the TSR domain of *P. falciparum* TRAP contains a heparin binding site. Protein Sci 15(7):1760-8.

Trucco C, Fernadez-Reyes D, Howell S et al. The merozoite surface protein 6 gene codes for a 36 kDa protein associated with the *Plasmodium falciparum* merozoite surface protein-1 complex. Mol Biochem Parasitol 2001; 112:91-101.

Tucker R. P. 2004. The thrombospondin type 1 repeat family. Int J. Biochem. Cell Biol. 36: 969-974.

Uchime O, Herrera R, Reiter K, Kotova S, Shimp R L, Jr., Miura K, Jones D, Lebowitz J, Ambroggio X, Hurt D E and others. 2012. Analysis of the Conformation and Function of the *Plasmodium falciparum* Merozoite Proteins MTRAP and PTRAMP. Eukaryot Cell 11(5):615-25.

Vaquero C, Sack M, Chandler J, Drossard J, Schuster F, Monecke M, Schillberg S, Fischer R. 1999. Transient expression of a tumor-specific single-chain fragment and a chimeric antibody in tobacco leaves. Proc Natl Acad Sci USA 96(20):11128-33.

Wasmuth, J., Daub, J., Peregrin-Alvarez, J. M., Finney, C. A., Parkinson, J. (2009). "The origins of apicomplexan sequence innovation." Genome Res 19(7): 1202-1213.

Wong C, Sridhara S, Bardwell J C, Jakob U. 2000. Heating greatly speeds Coomassie blue staining and destaining. Biotechniques 28(3):426-8, 430, 432.

What is claimed is:

1. A mixture of recombinant proteins suitable as an immunogenic composition for inducing an immune response in a human against the parasite *Plasmodium falciparum* comprising antigens from *Plasmodium falciparum* surface proteins of the pre-erythrocytic, the blood-, and the sexual-stage of the parasite life cycle, the mixture comprising:
   a) a fusion protein of the pre-erythrocytic antigens PfCelTOS, a TSR-domain of PfCSP (PfCSP_TSR) and a TSR-domain of PfTRAP (PfTRAP_TSR), wherein the fusion protein comprises an amino acid sequence of at least 90% sequence identity to SEQ ID NO. 1;
   b) a blood stage antigen(s) comprising at least one variant of Apical membrane antigen 1 (PfAMA1), or fragments thereof; and
   c) a sexual stage antigen(s) comprising the ookinete antigen Pfs25 and/or the gamete/gametocyte surface protein fragment Pf230C0.

2. The mixture according to claim 1, wherein the fusion protein comprises the amino acid sequence of SEQ ID NO. 1.

3. The mixture according to claim 1, wherein the sexual stage antigen comprises a fusion protein of Pfs25 and Pf230C0.

4. The mixture according to claim 1, wherein the blood stage antigens comprise at least a further *Plasmodium falciparum* blood stage antigen.

5. The mixture according to claim 4, wherein the further *Plasmodium falciparum* blood stage antigen is selected from the group consisting of PfMsp1, PfRIPR, PfRh2, PfMsp4, PfMsp8, PfRh5, and PfMsp3.

6. The mixture according to claim 4, wherein the further *Plasmodium falciparum* blood stage antigen is selected from the group consisting of PfMsp1-19, PfRIPR_EGF7/8, PfRh2, PfRh5a (Peptide), PfRh5b (Peptide), and N-terminal fragment of PfMsp3.

7. The mixture according to claim 1, wherein the blood stage antigens comprise PfAMA1-DICO1, PfAMA1-DICO2, and PfAMA1-DICO3.

8. The mixture according to claim 1, wherein the blood stage antigens comprise:
   i) PfAMA1-DICO1 and PfMsp1-19;
   ii) PfAMA1-DICO2 and PfRh2; and
   iii) PfAMA1-DICO3, PfRIPR_EGF7/8.

9. The mixture according to claim 1, wherein the blood stage antigens comprise PfAMA1-DICO1, PfAMA1-DICO2, and PfAMA1-DICO3, and wherein the sexual stage antigens comprise Pfs25 and Pfs230C0.

10. A mixture of recombinant proteins suitable as an immunogenic composition for inducing an immune response in a human against the parasite *Plasmodium falciparum* comprising antigens from *Plasmodium falciparum* surface proteins of the pre-erythrocytic, the blood-, and the sexual-stage of the parasite life cycle, the mixture comprising:
   a) a fusion protein of the pre-erythrocytic antigens PfCelTOS, a TSR-domain of PfCSP (PfCSP_TSR) and a TSR-domain of PfTRAP (PfTRAP_TSR), wherein the fusion protein comprises the amino acid sequence of SEQ ID NO. 26;
   b) blood stage antigens comprising variants of Apical membrane antigen 1 (PfAMA1), wherein the blood stage antigens comprise a polypeptide comprising the amino acid sequence of SEQ ID NO. 11, a polypeptide comprising the amino acid sequence of SEQ ID NO. 12 and a polypeptide comprising the amino acid sequence of SEQ ID NO. 13; and
   c) sexual stage antigens comprising the ookinete antigen Pfs25 and gamete/gametocyte surface protein fragment Pf230C0, wherein the sexual stage antigens comprise a polypeptide comprising the amino acid sequence of SEQ ID NO. 8.

11. The mixture according to claim 1, wherein the blood stage antigens comprise PfAMA1-DICO1, PfAMA1-DICO2, and PfAMA1-DICO3, and wherein the sexual stage antigens comprise Pfs25, Pfs230C0 and PfRh5b.

12. A mixture of recombinant proteins suitable as an immunogenic composition for inducing an immune response in a human against the parasite *Plasmodium falciparum* comprising antigens from *Plasmodium falciparum* surface proteins of the pre-erythrocytic, the blood-, and the sexual-stage of the parasite life cycle, the mixture comprising:
   a) a fusion protein of the pre-erythrocytic antigens PfCelTOS, a TSR-domain of PfCSP (PfCSP_TSR) and a TSR-domain of PfTRAP (PfTRAP_TSR), wherein the fusion protein comprises the amino acid sequence of SEQ ID NO. 9;
   b) blood stage antigens comprising variants of Apical membrane antigen 1 (PfAMA1), wherein the blood stage antigens comprise a polypeptide comprising the amino acid sequence of SEQ ID NO. 11, a polypeptide comprising the amino acid sequence of SEQ ID NO. 12 and a polypeptide comprising the amino acid sequence of SEQ ID NO. 13; and
   c) the sexual stage antigens comprising the ookinete antigen Pfs25 and gamete/gametocyte surface protein fragment Pf230C0, wherein the sexual stage antigens comprise a polypeptide comprising the amino acid sequence of SEQ ID NO. 28.

13. An immunogenic composition for inducing an immune response in human individuals against *Plasmodium falciparum* comprising as an active ingredient the mixture of claim 1 and a carrier in a physiologically acceptable medium.

14. The immunogenic composition according to claim 13, wherein the composition further comprises an adjuvant in an amount sufficient to enhance an immune response.

* * * * *